(12) United States Patent
Weaver et al.

(10) Patent No.: US 8,343,489 B2
(45) Date of Patent: Jan. 1, 2013

(54) METHODS FOR HUMANIZING ANTIBODIES AND HUMANIZED ANTIBODIES MADE THEREBY

(76) Inventors: David T. Weaver, Chestnut Hill, MA (US); Michael Rynkiewicz, Boston, MA (US)

( * ) Notice: Subject to any disclaimer, the term of this patent is extended or adjusted under 35 U.S.C. 154(b) by 693 days.

(21) Appl. No.: 12/293,926

(22) PCT Filed: Mar. 21, 2007

(86) PCT No.: PCT/US2007/064558
§ 371 (c)(1),
(2), (4) Date: Oct. 14, 2008

(87) PCT Pub. No.: WO2007/109742
PCT Pub. Date: Sep. 27, 2007

(65) Prior Publication Data
US 2009/0130102 A1  May 21, 2009

Related U.S. Application Data

(60) Provisional application No. 60/784,231, filed on Mar. 21, 2006, provisional application No. 60/848,201, filed on Sep. 29, 2006.

(51) Int. Cl.
*A61K 39/395* (2006.01)
*C07K 16/00* (2006.01)

(52) U.S. Cl. .................. 424/133.1; 435/69.6; 530/387.3; 530/388.1

(58) Field of Classification Search .............. 424/133.1; 435/69.6; 530/387.3, 388.1
See application file for complete search history.

(56) References Cited

OTHER PUBLICATIONS

ATCC search output for "2FD6" antibody (p. 1; Feb. 8, 2012).*
Padlan, Eduardo A., et al. "Identification of specificity-determining residues in antibodies." FASEB J.,9:133-9 (1995).
Tamura, Midori, et al., "Structural Correlates of an Anticarcinoma Antibody: Identification of Specificity-Determining Residues (SDRs) and Development of a Minimally Immunogenic Antibody Variant by Retention of SDRs Only." J. of Immun., 164:1432-41 (2000).
Form PCT/ISA/220—Notification of Transmittal of the International Search Report and the Written Opinion of the International Searching Authority, or the Declaration, dated Oct. 6, 2008, for International Application No. PCT/US07/064558.
Form PCT/ISA/210—International Search Report, dated Oct. 6, 2008 for International Application No. PCT/US07/064558.
Form PCT/ISA/237—Written Opinion of the International Searching Authority, dated Oct. 6, 2008 for International Application No. PCT/US07/064558.

* cited by examiner

*Primary Examiner* — Lynn Bristol
(74) *Attorney, Agent, or Firm* — Milstein Zhang & Wu LLC

(57) ABSTRACT

Disclosed herein is the use of three-dimensional structure information to guide the process of modifying antibodies with amino acids from one or more templates or surrogates such that the antigen binding properties of the parent antibody are maintained and the immunogenicity potential is reduced when administered as a therapeutic in humans.

18 Claims, 18 Drawing Sheets

Figure 1. Structure Grafting Method of the Invention as a Flow Chart

```
Light chain
1UZ8-1   1     DIVMTQA-AF SNPVTLGTSA SISCRSSKSL LYSNGITYLY WYLQKPGQSP
1DEE-Fv  1     DIQMTQSPSS L-SASVGDRV TITCRTSQSI S-----SYLN WYQQKPGKAP
1NL0-Fv  1     QSVLTQP-PS V-SAAPGQKV TISCSGSTSN I---GNNYVS WYQQHPGKAP
8FAB-Fv  3        ELTQP-PS VS-VSPGQTA RITCSA-NAL PN----QYAY WYQQKPGRAP
               .**.  .     . *      *.*. .         *     ** * ** .*

1UZ8-1   45    QLLIYQMSNL ASGVPDRFSS SGSGTDFTLR ISRVEAEDVG VYYCAQNLE-
1DEE-Fv  45    KLLIYAASSL QSGVPSRFSG SGSGTDFTLT ISSLQPEDFA TYYCQQSYS-
1NL0-Fv  45    KLMIYDVSKR PSGVPDRFSG SKSGNSASLD ISGLQSEDEA DYYCAAWDDS
8FAB-Fv  44    VMVIYKDTQR PSGIPQRFSS STSGTTVTLT ISGVQAEDEA DYYCQAWD--
               ..**  .    **.* ***. * **    .*  **  ..**  .  ***

1UZ8-1   94    -VPWTFGGGT KLEIKR---  [SEQ ID No. 45]
1DEE-Fv  94    -APRTFGQGT KVEIK----  [SEQ ID No. 46]
1NL0-Fv  95    LSEFLFGTGT KLTVLGQPK  [SEQ ID No. 47]
8FAB-Fv  92    NSASIFGGGT KLTVLGQPK  [SEQ ID No. 48]
                    **  ** *. .

Heavy Chain
1UZ8-1   1     EVKLLESGGG LVQPGGSQKL SCAASGFDFS GYWMSWVRQA PGKGLEWIGE
1DEE-Fv  1     QVQLVESGGG VVQPGKSLRL SCAASGFTFS GYGMHWVRQA PGKGLEWVAL
1NL0-Fv  1     GVQLVESGGG VVQPGRSLRL SCAASGFTFS TYAMHWVRQA PGKGLEWVAI
8FAB-Fv  1     AVKLVQAGGG VVQPGRSLRL SCIASGFTFS NYGMHWVRQA PGKGLEWVAV
               * *...*** .****  * .*  ** **** **  *  ***** ******* ..

1UZ8-1   51    INPDSSTINY TPSLKDKFIIS RDNAKNTLY LQMSKVRSED TALYYCARET
1DEE-Fv  551   ISYDESNKYY ADSVKGRFTIS RDNSKNTLY LQMNSLRAED TAVYYCAKVK
1NL0-Fv  51    ISYDGSKKYY ADSVKGRFTIS RDNSKNTLY LQMNSLRAED TAVYYCARAS
8FAB-Fv  51    IWYNGSRTYY GDSVKGRFTIS RDNSKRTLY MQMNSLRTED TAVYYCARDP
               *  . *  *   *.* .* **  ***.* ***  .**. .*.** **.****.

1UZ8-1   81    GT----RFDY WGQGTTLTVSS  [SEQ ID No. 49]
1DEE-Fv  582   FYDPTAPNDY WGQGTLVTVS   [SEQ ID No. 50]
1NL0-Fv  81    IAA-ARVLDY WGRGTMVTVSS  [SEQ ID No. 51]
8FAB-Fv  82    DILTAFSFDY WGQGVLVTVSS  [SEQ ID No. 52]
                    ** **.*  .***
```

Figure 3

| Loop | Residue Number | Source PDB | Amino Acid | Calculated Energy (kJ/mol) |
|---|---|---|---|---|
| CDR-L1 | 27B | Parent | L | -44.584 |
|  | L27bI | 1dee | I | -30.008 |
|  | 27C | Parent | L | -28.228 |
|  | L27cS | 1dee | S | -34.289 |
|  |  | 1nl0 | I | 16.778 |
|  | 31 | Parent | T | -46.598 |
|  | T31S | 1dee | S | -37.134 |
|  | 33 | Parent | L | -64.551 |
|  |  | 1nl0 | V | 53.886 |
|  | L33A | 8fab | A | -44.977 |
| CDR-L2 | 52 | Parent | S | 9.883 |
|  | S52T | 8fab | T | -23.837 |
|  | 53 | Parent | N | -200.95 |
|  | N53S | 1dee | S | -11.582 |
|  | N53K | 1nl0 | K | -41.155 |
|  | N53Q | 8fab | Q | -199.597 |
|  | 54 | Parent | L | -20.917 |
|  | L54R | 1nl0, 8fab | R | -277.295 |
| CDR-L3 | 90 | Parent | Q | -239.882 |
|  | Q90A | 1nl0, 8fab | A | -37.414 |
| CDR-H2 | 52 | Parent | N | -191.022 |
|  | N52S | 1dee, 1nl0 | S | -30.487 |
|  | 54 | Parent | S | -27.784 |
|  | S54E | 1dee | E | -13.277 |
|  |  | 1nl0, 8fab | G | 19.348 |
|  | 56 | Parent | T | -44.631 |
|  | T56N | 1dee | N | -202.322 |
|  | T56K | 1nl0 | K | -39.623 |
|  | T56R | 8fab | R | -290.73 |
|  | 57 | Parent | I | -10.023 |
|  | I57K | 1dee, 1nl0 | K | -34.821 |
|  | I57T | 8fab | T | -22.042 |
|  | 63 | Parent | L | -27.443 |
|  | L63V | 1dee, 1nl0, 8fab | V | -24.146 |
|  | 65 | Parent | D | -7.129 |
|  |  | 1dee, 1nl0, 8fab | G | 35.078 |
|  | 66 | Parent | K | -27.611 |
|  | K66R | 1dee, 1nl0, 8fab | R | -291.046 |

Figure 5

| Loop | Residue # | Source PDB | Amino Acid | Energy (kJ/mol) |
|---|---|---|---|---|
| CDR-L1 | 30 | parent | V | -30.798 |
| | | HuFR1, HuFR2 | I | -13.181 |
| CDR-L2 | 49 | parent | F | -57.543 |
| | | HuFR1, HuFR2, HuFR3, HuFR4 | Y | -105.605 |
| | 51 | parent | I | -20.925 |
| | | HuFR1, HuFR2, HuFR4 | A | -21.205 |
| | | HuFR3 | D | -26.652 |
| CDR-L3 | 90 | parent, HuFR2, HuFR1 | Q | -223.364 |
| CDR-H1 | 29 | parent, HuFR2 | F | -45.135 |
| | 30 | parent, HuFR4 | T | -39.749 |
| | | HuFR2 | S | -33.582 |
| | 31 | parent | N | -175.243 |
| | | HuFR2 | D | -27.805 |
| | 32 | parent, HuFR2 | F | -47.985 |
| | | HuFR4 | L | -12.731 |
| | 34 | parent, HuFR1, HuFR3 | I | -42.707 |
| | | HuFR2 | M | -61.085 |
| | | HuFR4 | V | -45.171 |
| CDR-H2 | 51 | parent, HuFR1, HuFR2, HuFR3 | I | -34.072 |
| | | HuFR4 | F | -18.956 |
| | 52a | parent | H | 7.203 |
| | 53 | parent | G | 12.527 |
| | 54 | parent | S | -29.574 |
| | 61 | parent, HuFR2 | E | -14.107 |
| | | HuFR1, HuFR3 | Q | -171.157 |
| CDR-H3 | 96 | parent | G | 48.448 |
| | 100 | parent | Y | -111.611 |
| | | HuFR2 | A | -34.025 |
| | 100a | parent, HuFR1, HuFR2, HuFR4 | F | -59.609 |
| | | HuFR3 | K | -62.522 |

Figure 9

Figure 10. EPU Method of the Invention as a Flow Chart
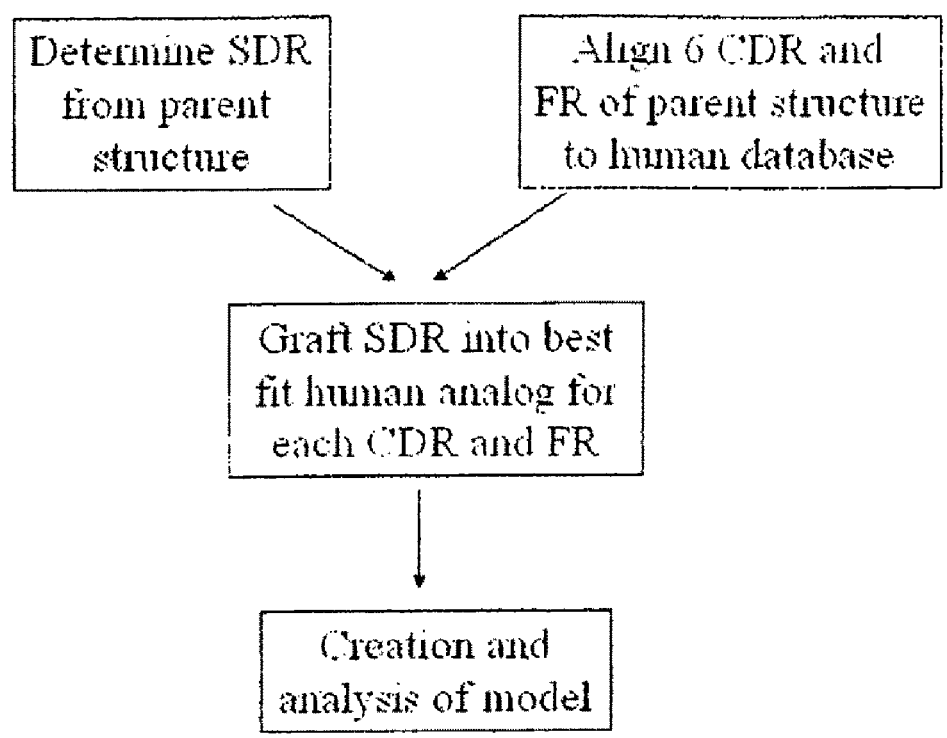

Figure 11. EPU Method of the Invention in an Outline

1) Determine SDR of parent structure
   a) Residues within 5 Å of hapten in cocrystal structure if available
   b) Residues making contribution to binding surface as determined by visual inspection with Deep View
   c) Residues making key structural contributions to loops as determined by inspection of structure
      i) Key side chain interactions (salt bridge, hydrogen bonds, van der Waal's)
      ii) Small side chains (G or A or S) where required
2) Align 6 CDR and FR of parent structure to human database
   a) Extract 6 CDR loops and variable region FR (Fv less the CDR loops) from the parent structure
   b) Overlay with library of human CDR and FR structures with Magic Fit in Deep View
   c) Score by number of backbone atoms fit and rmsd for CDR loops
   d) Score by rmsd for > 90% of alpha carbons fit for FR
3) Graft SDR into best fit human analog for each CDR and FR
   a) Replace residues in human structures with parental SDR
   b) Use structures that require minimal changes
   c) Single mutations/grafting multiple residues of parental structures
4) Model creation and analysis
   a) Insert modified CDR structures into chosen modified FR
   b) Initial energy calculations suggest changes to relieve poor contacts in model
   c) Energy minimization of final model A. Alignment of CDRL1

| Antibody | Sequence | | RMSD | % Backbone atoms aligned |
|---|---|---|---|---|
| Parent | CSASSSV*S*YMHW | [SEQ ID No. 53] | - | - |
| HUMAN1* | CRASSSVT̲YIHW | [SEQ ID No. 54] | 0.36 | 100 |
| Consensus | * *****.*.** | | | |

B. Alignment of CDRL2

| Antibody | Sequence | | RMSD | % Backbone atoms aligned |
|---|---|---|---|---|
| Parent | F*E*ISKLASG | [SEQ ID No. 55] | - | - |
| HUMAN1* | YATSNLASG | [SEQ ID No. 56] | 0.18 | 100 |
| HUMAN5 | YAASSLQSG | [SEQ ID No. 57] | 0.21 | 100 |
| HUMAN7* | YDASSRATG | [SEQ ID No. 58] | 0.21 | 100 |
| HUMAN15 | YGASTRATG | [SEQ ID No. 59] | 0.22 | 100 |
| Consensus | . * .* | | | |

C. Alignment of CDRH1

| Antibody | Sequence | | RMSD | % Backbone atoms aligned |
|---|---|---|---|---|
| Parent | GYSFTNFYI*H*W | [SEQ ID No. 60] | - | - |
| HUMAN18* | SGYRFSNFVIHW | [SEQ ID No. 61] | 0.22 | 100 |
| HUMAN16 | SGYNFTSYW̲INW | [SEQ ID No. 62] | 0.25 | 100 |
| HUMAN2* | SGYTFTDYYIN̲W | [SEQ ID No. 63] | 0.28 | 100 |
| HUMAN26 | SGYTFSDFYMY̲W | [SEQ ID No. 64] | 0.31 | 100 |
| HUMAN1 | GFTFTDYYMNWV | [SEQ ID No. 65] | 0.32 | 100 |
| HUMAN36 | SGYSFTSYGLHW | [SEQ ID No. 66] | 0.34 | 100 |
| Consensus | *. *.... * | | | |

D. Alignment of CDRH2

| Antibody | Sequence | | RMSD | % Backbone atoms aligned |
|---|---|---|---|---|
| Parent | W*I*FHGS*DNTE*Y*N*EKFKDKAT | [SEQ ID No. 67] | - | - |
| HUMAN33 | GGVIPLLTITNYAPRFQGRIT | [SEQ ID No. 68] | 0.95 | 90 |
| HUMAN8 | AVISSDGGNKYYTDSVKGRFTI | [SEQ ID No. 69] | 0.99 | 90 |
| HUMAN14* | SGVFGSGGNTDYA̲DAVKGRFTI | [SEQ ID No. 70] | 0.99 | 90 |
| HUMAN16* | GD̲IYPGSGITN̲YNEKFKSKATL | [SEQ ID No. 71] | 0.48 | 85 |
| Consensus | . * . * | | | |

Figure 12

E. Alignment of CDRH3

| Antibody | Sequence | | RMSD | % Backbone atoms aligned |
|---|---|---|---|---|
| Parent | CARWGP------------HWY-FDVW | [SEQ ID No. 72] | | |
| HUMAN26 | CAADP----W-------ELNA-FNVW | [SEQ ID No. 73] | 1.16 | 93 |
| HUMAN23 | CTTDGFIMIRG-VSEDYYYY-MDVW | [SEQ ID No. 74] | 0.96 | 86 |
| HUMAN43 | CAHRRGPTTLAAAAAAGPVNAMDVW | [SEQ ID No. 75] | 0.99 | 86 |
| HUMAN6 | CVKGRDYYDS----GGYFTVA-FDIW | [SEQ ID No. 76] | 0.70 | 78 |
| HUMAN20* | CARKGSDR-------LSDNDP-FDAW | [SEQ ID No. 77] | 0.73 | 71 |
| Consensus | * | . * | | |

F. Alignment of framework regions

| Source Structure | RMSD | % CA aligned |
|---|---|---|
| HUMAN29 | 0.76 | 97 |
| HUMAN26 | 0.88 | 96 |
| HUMAN15 | 0.88 | 95 |
| HUMAN8 | 0.91 | 96 |
| HUMAN46 | 0.94 | 91 |
| HUMAN34 | 0.96 | 96 |
| HUMAN2 | 1.00 | 96 |
| HUMAN33 | 1.01 | 97 |
| HUMAN42 | 1.02 | 93 |
| HUMAN24 | 1.02 | 95 |
| HUMAN30 | 1.04 | 94 |
| HUMAN7 | 1.04 | 94 |
| HUMAN43 | 1.05 | 95 |
| HUMAN17 | 1.05 | 46 |
| HUMAN36 | 1.08 | 96 |
| HUMAN37 | 1.10 | 96 |

Figure 12 (continued)

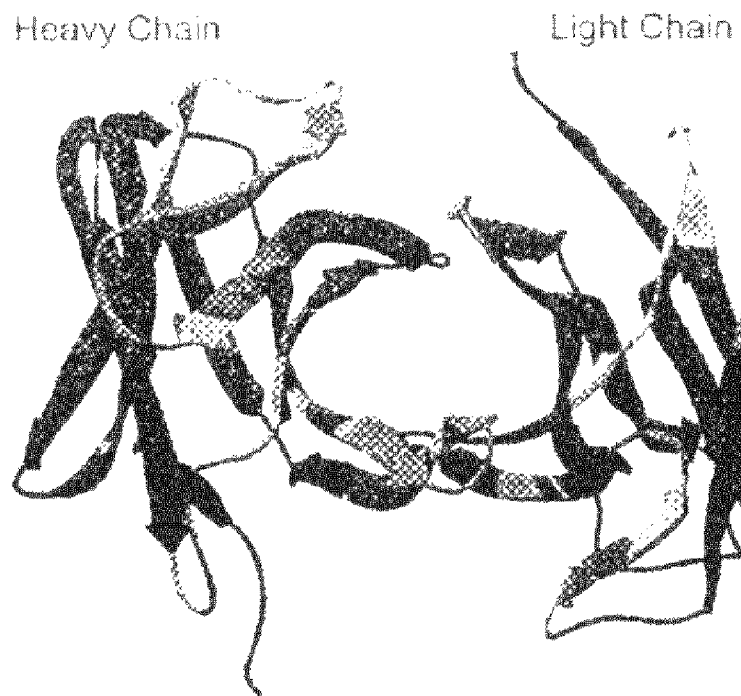
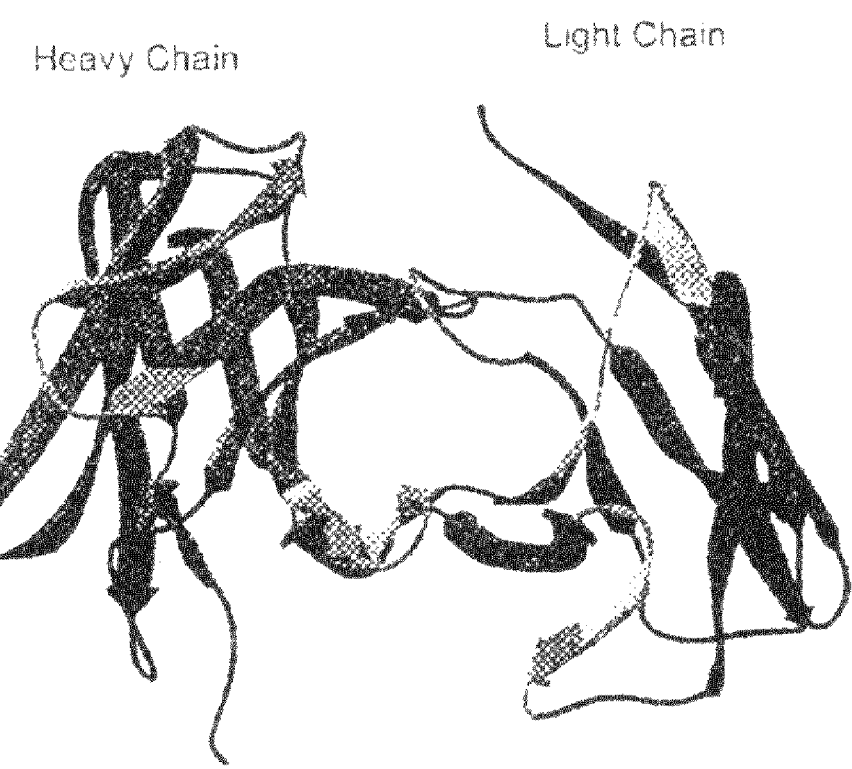
Figure 13

Light chain
Construct1  DIQMTQSPSTLSASVGDRVTITCRASSSVSYIHWYQQKPGRAPKPL
Construct2  DIQMTQSPSTLSASVGDRVTITCRASSSVSYIHWYQQKPGRAPKPL
Construct3  DIQMTQSPSTLSASVGDRVTITCRASSSVSYIHWYQQKPGRAPKPL
Construct4  DIQMTQSPSTLSASVGDRVTITCRASSSVSYIHWYQQKPGRAPKPL
Construct5  DIQMTQSPSTLSASVGDRVTITCRASSSVSYIHWYQQKPGRAPKPL
Construct6  DIQMTQSPSTLSASVGDRVTITCRASSSVSYIHWYQQKPGRAPKPL
Construct7  DIQMTQSPSTLSASVGDRVTITCRASSSVSYIHWYQQKPGRAPKPL
Construct8  DIQMTQSPSTLSASVGDRVTITCRASSSVSYIHWYQQKPGRAPKPL Construct1  MYEASSRATGVPSRFSGSGSGTEYTLTISSLQSDDFATYYCQQWNY
Construct2  MYEASSRATGVPSRFSGSGSGTEYTLTISSLQSDDFATYYCQQWNY
Construct3  MYEASSRATGVPSRFSGSGSGTEYTLTISSLQSDDFATYYCQQWNY
Construct4  MYETSNLASGVPSRFSGSGSGTEYTLTISSLQSDDFATYYCQQWNY
Construct5  MYETSNLASGVPSRFSGSGSGTEYTLTISSLQSDDFATYYCQQWNY
Construct6  MYETSNLASGVPSRFSGSGSGTEYTLTISSLQSDDFATYYCQQWNY
Construct7  MYETSNLASGVPSRFSGSGSGTEYTLTISSLQSDDFATYYCQQWNY
Construct8  MYEASSRATGVPSRFSGSGSGTEYTLTISSLQSDDFATYYCQQWNY Construct1  PFTFGQGTKLEIK  [SEQ ID No. 78]
Construct2  PFTFGQGTKLEIK  [SEQ ID No. 79]
Construct3  PFTFGQGTKLEIK  [SEQ ID No. 80]
Construct4  PFTFGQGTKLEIK  [SEQ ID No. 81]
Construct5  PFTFGQGTKLEIK  [SEQ ID No. 82]
Construct6  PFTFGQGTKLEIK  [SEQ ID No. 83]
Construct7  PFTFGQGTKLEIK  [SEQ ID No. 84]
Construct8  PFTFGQGTKLEIK  [SEQ ID No. 85]

Figure 15

Heavy chain

```
Construct1  EVQLVQSGAEVKKPGSSVKVSCKASGYTFTDYYIHWVRQAPGQGLE
Construct2  EVQLVQSGAEVKKPGSSVKVSCKASGYTFTDYYIHWVRQAPGQGLE
Construct3  EVQLVQSGAEVKKPGSSVKVSCKASGYRFSNFYIHWVRQAPGQGLE
Construct4  EVQLVQSGAEVKKPGSSVKVSCKASGYTFTDYYIHWVRQAPGQGLE
Construct5  EVQLVQSGAEVKKPGSSVKVSCKASGYTFTDYYIHWVRQAPGQGLE
Construct6  EVQLVQSGAEVKKPGSSVKVSCKASGYRFSNFYIHWVRQAPGQGLE
Construct7  EVQLVQSGAEVKKPGSSVKVSCKASGYRFSNFYIHWVRQAPGQGLE
Construct8  EVQLVQSGAEVKKPGSSVKVSCKASGYRFSNFYIHWVRQAPGQGLE Construct1  WIGWIFHGSDNTEYNDAVKGRFSITADESTSTAYMELSSLRSEDTA
Construct2  WIGWIFHGSDNTEYNEKFKSKATITADESTSTAYMELSSLRSEDTA
Construct3  WIGWIFHGSDNTEYNEKFKSKATITADESTSTAYMELSSLRSEDTA
Construct4  WIGWIFHGSDNTEYNDAVKGRFSITADESTSTAYMELSSLRSEDTA
Construct5  WIGWIFHGSDNTEYNEKFKSKATITADESTSTAYMELSSLRSEDTA
Construct6  WIGWIFHGSDNTEYNDAVKGRFSITADESTSTAYMELSSLRSEDTA
Construct7  WIGWIFHGSDNTEYNEKFKSKATITADESTSTAYMELSSLRSEDTA
Construct8  WIGWIFHGSDNTEYNDAVKGRFSITADESTSTAYMELSSLRSEDTA Construct1  VFYCARWGPHWYFDAWGRGTLVTVS  [SEQ ID No. 86]
Construct2  VFYCARWGPHWYFDAWGRGTLVTVS  [SEQ ID No. 87]
Construct3  VFYCARWGPHWYFDAWGRGTLVTVS  [SEQ ID No. 88]
Construct4  VFYCARWGPHWYFDAWGRGTLVTVS  [SEQ ID No. 89]
Construct5  VFYCARWGPHWYFDAWGRGTLVTVS  [SEQ ID No. 90]
Construct6  VFYCARWGPHWYFDAWGRGTLVTVS  [SEQ ID No. 91]
Construct7  VFYCARWGPHWYFDAWGRGTLVTVS  [SEQ ID No. 92]
Construct8  VFYCARWGPHWYFDAWGRGTLVTVS  [SEQ ID No. 93]
```

Figure 15 (continued)

SEQUENCE LISTING

```
<160> NUMBER OF SEQ ID NOS: 93

<210> SEQ ID NO 1
<211> LENGTH: 105
<212> TYPE: PRT
<213> ORGANISM: Homo sapiens

<400> SEQUENCE: 1

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Ser Tyr Ile
            20                  25                  30

His Trp Tyr Gln Gln Lys Pro Gly Arg Ala Pro Lys Pro Leu Met Tyr
        35                  40                  45

Glu Ala Ser Ser Arg Ala Thr Gly Val Pro Ser Arg Phe Ser Gly Ser
    50                  55                  60

Gly Ser Gly Thr Glu Tyr Thr Leu Thr Ile Ser Ser Leu Gln Ser Asp
65                  70                  75                  80

Asp Phe Ala Thr Tyr Tyr Cys Gln Gln Trp Asn Tyr Pro Phe Thr Phe
                85                  90                  95

Gly Gln Gly Thr Lys Leu Glu Ile Lys
            100                 105

<210> SEQ ID NO 2
<211> LENGTH: 117
<212> TYPE: PRT
<213> ORGANISM: Homo sapiens

<400> SEQUENCE: 2

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Ile
        35                  40                  45

Gly Trp Ile Phe His Gly Ser Asp Asn Thr Glu Tyr Asn Asp Ala Val
    50                  55                  60

Lys Gly Arg Phe Ser Ile Thr Ala Asp Glu Ser Thr Ser Thr Ala Tyr
65                  70                  75                  80

Met Glu Leu Ser Ser Leu Arg Ser Glu Asp Thr Ala Val Phe Tyr Cys
                85                  90                  95

Ala Arg Trp Gly Pro His Trp Tyr Phe Asp Ala Trp Gly Arg Gly Thr
            100                 105                 110

Leu Val Thr Val Ser
```

```
                    115

<210> SEQ ID NO 3
<211> LENGTH: 117
<212> TYPE: PRT
<213> ORGANISM: Homo sapiens

<400> SEQUENCE: 3

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Ile
            35                  40                  45

Gly Trp Ile Phe His Gly Ser Asp Asn Thr Glu Tyr Asn Glu Lys Phe
    50                  55                  60

Lys Ser Lys Ala Thr Ile Thr Ala Asp Glu Ser Thr Ser Thr Ala Tyr
65                  70                  75                  80

Met Glu Leu Ser Ser Leu Arg Ser Glu Asp Thr Ala Val Phe Tyr Cys
                85                  90                  95

Ala Arg Trp Gly Pro His Trp Tyr Phe Asp Ala Trp Gly Arg Gly Thr
            100                 105                 110

Leu Val Thr Val Ser
        115

<210> SEQ ID NO 4
<211> LENGTH: 105
<212> TYPE: PRT
<213> ORGANISM: Homo sapiens

<400> SEQUENCE: 4

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Arg Phe Ser Asn Phe
                20                  25                  30

Tyr Ile His Trp Val Arg Gln Ala Pro Gly Gln Gly Leu Glu Trp Ile
            35                  40                  45

Gly Trp Ile Phe His Gly Ser Asp Asn Thr Glu Tyr Asn Glu Lys Phe
    50                  55                  60

Lys Ser Lys Ala Thr Ile Thr Ala Asp Glu Ser Thr Ser Thr Ala Tyr
65                  70                  75                  80

Met Glu Leu Ser Ser Leu Arg Ser Glu Asp Thr Ala Pro Phe Thr Phe
                85                  90                  95

Gly Gln Gly Thr Lys Leu Glu Ile Lys
            100                 105

<210> SEQ ID NO 5
<211> LENGTH: 105
<212> TYPE: PRT
<213> ORGANISM: Homo sapiens

<400> SEQUENCE: 5

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Ser Tyr Ile
                20                  25                  30

His Trp Tyr Gln Gln Lys Pro Gly Arg Ala Pro Lys Pro Leu Met Tyr
            35                  40                  45
```

Glu Thr Ser Asn Leu Ala Ser Gly Val Pro Ser Arg Phe Ser Gly Ser
            50                  55                  60

Gly Ser Gly Thr Glu Tyr Thr Leu Thr Ile Ser Ser Leu Gln Ser Asp
65                  70                  75                  80

Asp Phe Ala Thr Tyr Tyr Cys Gln Gln Trp Asn Tyr Pro Phe Thr Phe
                85                  90                  95

Gly Gln Gly Thr Lys Leu Glu Ile Lys
            100                 105

<210> SEQ ID NO 6
<211> LENGTH: 117
<212> TYPE: PRT
<213> ORGANISM: Homo sapiens

<400> SEQUENCE: 6

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Ile
        35                  40                  45

Gly Trp Ile Phe His Gly Ser Asp Asn Thr Glu Tyr Asn Asp Ala Val
50                  55                  60

Lys Gly Arg Phe Ser Ile Thr Ala Asp Glu Ser Thr Ser Thr Ala Tyr
65                  70                  75                  80

Met Glu Leu Ser Ser Leu Arg Ser Glu Asp Thr Ala Val Phe Tyr Cys
                85                  90                  95

Ala Arg Trp Gly Pro His Trp Tyr Phe Asp Ala Trp Gly Arg Gly Thr
            100                 105                 110

Leu Val Thr Val Ser
            115

<210> SEQ ID NO 7
<211> LENGTH: 112
<212> TYPE: PRT
<213> ORGANISM: Homo sapiens

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Thr Ser Lys Ser Leu Leu Tyr Ser
            20                  25                  30

Asn Gly Ile Thr Tyr Leu Tyr Trp Tyr Gln Gln Lys Pro Gly Lys Ala
        35                  40                  45

Pro Lys Leu Leu Ile Tyr Gln Met Ser Asn Leu Ala Ser Gly Val Pro
    50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Val Pro Trp Thr Phe Gly Gln Gly Thr Lys Val Glu Ile Lys
            100                 105                 110

<210> SEQ ID NO 8
<211> LENGTH: 117
<212> TYPE: PRT
<213> ORGANISM: Homo sapiens

<400> SEQUENCE: 8

Gln Val Gln Leu Val Glu Ser Gly Gly Gly Val Val Gln Pro Gly Lys
1               5                   10                  15

Ser Leu Arg Leu Ser Cys Ala Ala Ser Gly Phe Thr Phe Ser Gly Tyr
            20                  25                  30

Trp Met Ser Trp Val Arg Gln Ala Pro Gly Lys Gly Leu Glu Trp Val
        35                  40                  45

Ala Glu Ile Asn Pro Asp Ser Ser Thr Ile Asn Tyr Thr Pro Ser Leu
    50                  55                  60

Lys Asp Lys Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Lys Glu Thr Gly Thr Arg Phe Asp Tyr Trp Gly Gln Gly Thr Leu
            100                 105                 110

Val Thr Val Ser Ser
        115

<210> SEQ ID NO 9
<211> LENGTH: 115
<212> TYPE: PRT
<213> ORGANISM: Homo sapiens

<400> SEQUENCE: 9

Gln Ser Val Leu Thr Gln Pro Pro Ser Val Ser Ala Ala Pro Gly Gln
1               5                   10                  15

Lys Val Thr Ile Ser Cys Ser Ser Lys Ser Leu Leu Tyr Ser Asn
            20                  25                  30

Gly Ile Thr Tyr Leu Tyr Trp Tyr Gln Gln His Pro Gly Lys Ala Pro
        35                  40                  45

Lys Leu Met Ile Tyr Gln Met Ser Asn Leu Ala Ser Gly Val Pro Asp
    50                  55                  60

Arg Phe Ser Ser Ser Gly Ser Gly Thr Asp Phe Thr Leu Asp Ile Ser
65              70                  75                  80

Gly Leu Gln Ser Glu Asp Glu Ala Asp Tyr Tyr Cys Ala Gln Asn Leu
                85                  90                  95

Glu Val Pro Trp Leu Phe Gly Thr Gly Thr Lys Leu Thr Val Leu Gly
            100                 105                 110

Gln Pro Lys
        115

<210> SEQ ID NO 10
<211> LENGTH: 117
<212> TYPE: PRT
<213> ORGANISM: Homo sapiens

<400> SEQUENCE: 10

Gly Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Arg Phe Thr Ile Ser Arg Asp Asn Ser Lys Asn Thr Leu Tyr
65              70                  75                  80

```
Leu Gln Met Asn Ser Leu Arg Ala Glu Asp Thr Ala Val Tyr Tyr Cys
                85                  90                  95

Ala Arg Glu Thr Gly Thr Arg Phe Asp Tyr Trp Gly Arg Gly Thr Met
            100                 105                 110

Val Thr Val Ser Ser
        115

<210> SEQ ID NO 11
<211> LENGTH: 113
<212> TYPE: PRT
<213> ORGANISM: Homo sapiens

<400> SEQUENCE: 11

Glu Leu Thr Gln Pro Pro Ser Val Ser Val Ser Pro Gly Gln Thr Ala
1               5                   10                  15

Arg Ile Thr Cys Ser Ser Ser Lys Ser Leu Leu Tyr Ser Asn Gly Ile
            20                  25                  30

Thr Tyr Ala Tyr Trp Tyr Gln Gln Lys Pro Gly Arg Ala Pro Val Met
        35                  40                  45

Val Ile Tyr Gln Met Ser Asn Leu Ala Ser Gly Ile Pro Gln Arg Phe
    50                  55                  60

Ser Ser Ser Thr Ser Gly Thr Thr Val Thr Leu Thr Ile Ser Gly Val
65                  70                  75                  80

Gln Ala Glu Asp Glu Ala Asp Tyr Tyr Cys Ala Gln Asn Leu Glu Val
                85                  90                  95

Pro Trp Ile Phe Gly Gly Gly Thr Lys Leu Thr Val Leu Gly Gln Pro
            100                 105                 110

Lys

<210> SEQ ID NO 12
<211> LENGTH: 117
<212> TYPE: PRT
<213> ORGANISM: Homo sapiens

<400> SEQUENCE: 12

Ala Val Lys Leu Val Gln Ala Gly Gly Gly Val Val Gln Pro Gly Arg
1               5                   10                  15

Ser Leu Arg Leu Ser Cys Ile Ala Ser Gly Phe Thr Phe Ser Asn Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Arg Phe Thr Ile Ser Arg Asp Asn Ser Lys Arg Thr Leu Tyr
65                  70                  75                  80

Met Gln Met Asn Ser Leu Arg Thr Glu Asp Thr Ala Val Tyr Tyr Cys
                85                  90                  95

Ala Arg Glu Thr Gly Thr Arg Phe Asp Tyr Trp Gly Gln Gly Val Leu
            100                 105                 110

Val Thr Val Ser Ser
        115

<210> SEQ ID NO 13
<211> LENGTH: 105
<212> TYPE: PRT
<213> ORGANISM: Homo sapiens

<400> SEQUENCE: 13
```

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Ser Tyr Leu
            20                  25                  30

Ala Trp Tyr Gln Gln Lys Pro Gly Arg Ala Pro Lys Pro Leu Met Phe
        35                  40                  45

Glu Ile Ser Ser Leu Lys Ser Gly Val Pro Ser Arg Phe Ser Gly Ser
    50                  55                  60

Gly Ser Gly Thr Glu Tyr Thr Leu Thr Ile Ser Ser Leu Gln Ser Asp
65                  70                  75                  80

Asp Phe Ala Thr Tyr Tyr Cys Gln Gln Trp Asn Tyr Pro Phe Thr Phe
                85                  90                  95

Gly Gln Gly Thr Lys Leu Glu Ile Lys
            100                 105

<210> SEQ ID NO 14
<211> LENGTH: 117
<212> TYPE: PRT
<213> ORGANISM: Homo sapiens

<400> SEQUENCE: 14

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Asn Phe
            20                  25                  30

Tyr Ile His Trp Val Arg Gln Ala Pro Gly Gln Gly Leu Glu Trp Met
        35                  40                  45

Gly Trp Ile Phe His Gly Ser Asp Asn Thr Glu Tyr Asn Glu Arg Phe
    50                  55                  60

Gln Gly Arg Val Ser Ile Thr Ala Asp Glu Ser Thr Ser Thr Ala Tyr
65                  70                  75                  80

Met Glu Leu Ser Ser Leu Arg Ser Glu Asp Thr Ala Val Phe Tyr Cys
                85                  90                  95

Ala Arg Trp Gly Pro His Trp Tyr Phe Asp Leu Trp Gly Arg Gly Thr
            100                 105                 110

Leu Val Thr Val Ser
        115

<210> SEQ ID NO 15
<211> LENGTH: 104
<212> TYPE: PRT
<213> ORGANISM: Homo sapiens

<400> SEQUENCE: 15

Ile Ala Leu Thr Gln Ser Pro Gly Thr Leu Ser Leu Ser Pro Gly Glu
1               5                   10                  15

Arg Ala Thr Leu Ser Cys Arg Ala Ser Ser Ser Val Ser Tyr Met Ala
            20                  25                  30

Trp Tyr Gln Gln Lys Pro Gly Gln Ala Pro Arg Leu Leu Ile Phe Glu
        35                  40                  45

Ile Ser Thr Arg Ala Thr Gly Ile Pro Asp Arg Phe Ser Gly Ser Gly
    50                  55                  60

Ser Gly Thr Asp Tyr Thr Leu Thr Ile Ser Arg Leu Glu Pro Glu Asp
65                  70                  75                  80

Phe Ala Val Tyr Tyr Cys Gln Gln Trp Asn Tyr Pro Phe Thr Phe Gly
                85                  90                  95

Gln Gly Thr Arg Leu Glu Ile Lys
            100

<210> SEQ ID NO 16
<211> LENGTH: 118
<212> TYPE: PRT
<213> ORGANISM: Homo sapiens

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Tyr Ile His Trp Val Arg Gln Ala Pro Gly Lys Gly Leu Glu Trp Val
        35                  40                  45

Gly Trp Ile Phe His Gly Ser Asp Asn Thr Glu Tyr Asn Glu Lys Phe
    50                  55                  60

Gln Gly Ser Val Thr Met Thr Ala Asp Thr Ser Thr Asn Ile Ala Tyr
65                  70                  75                  80

Met Glu Leu Ser Ser Leu Arg Ser Asp Asp Thr Ala Val Tyr Tyr Cys
                85                  90                  95

Ala Arg Trp Gly Pro His Trp Tyr Phe Asp Val Trp Gly Gln Gly Thr
            100                 105                 110

Met Val Thr Val Ser Ser
        115

<210> SEQ ID NO 17
<211> LENGTH: 108
<212> TYPE: PRT
<213> ORGANISM: Homo sapiens

<400> SEQUENCE: 17

Ser Ile Glu Leu Thr Gln Pro Pro Ser Val Ser Val Ala Pro Gly Lys
1               5                   10                  15

Thr Ala Arg Ile Thr Cys Gly Ala Ser Ser Ser Val Ser Tyr Met His
            20                  25                  30

Trp Tyr Gln Gln Lys Pro Gly Gln Ala Pro Val Pro Val Tyr Glu
        35                  40                  45

Asp Ser Asp Arg Pro Ser Gly Ile Pro Glu Arg Phe Ser Gly Ser Gly
    50                  55                  60

Ser Gly Asn Thr Tyr Thr Leu Thr Ile Ser Arg Val Glu Ala Gly Asp
65                  70                  75                  80

Glu Ala Asp Tyr Tyr Cys Gln Gln Trp Asn Tyr Pro Phe Val Phe Gly
                85                  90                  95

Thr Gly Thr Lys Val Thr Val Leu Gly Gln Pro Lys
            100                 105

<210> SEQ ID NO 18
<211> LENGTH: 118
<212> TYPE: PRT
<213> ORGANISM: Homo sapiens

<400> SEQUENCE: 18

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Phe
            20                  25                  30

Tyr Ile His Trp Val Arg Gln Ala Pro Gly Gln Gly Leu Glu Trp Met
        35                  40                  45

Gly Trp Ile Phe His Gly Ser Asp Asn Thr Glu Tyr Asn Gln Lys Phe
            50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Pro His Trp Tyr Phe Asp Val Trp Gly Gln Gly Thr
            100                 105                 110

Thr Val Thr Val Ser Ser
            115

<210> SEQ ID NO 19
<211> LENGTH: 104
<212> TYPE: PRT
<213> ORGANISM: Homo sapiens

<400> SEQUENCE: 19

Ile Gln Met Thr Gln Ser Pro Ser Ser Val Ser Ala Ser Val Gly Asp
1               5                   10                  15

Arg Val Thr Ile Thr Cys Arg Ala Ser Gln Asp Val Ser Tyr Met Ala
            20                  25                  30

Trp Tyr Gln Gln Lys Pro Gly Lys Ala Pro Lys Pro Trp Ile Phe Glu
        35                  40                  45

Ile Ser Thr Leu Gln Ser Gly Val Pro Ser Arg Phe Ser Gly Ser Gly
    50                  55                  60

Ser Gly Thr Asp Tyr Ser Leu Thr Ile Asn Ser Leu Gln Pro Glu Asp
65                  70                  75                  80

Phe Ala Thr Tyr Tyr Cys Gln Gln Trp Asn Tyr Pro Phe Thr Phe Gly
                85                  90                  95

Gly Gly Thr Lys Val Glu Ile Lys
            100

<210> SEQ ID NO 20
<211> LENGTH: 118
<212> TYPE: PRT
<213> ORGANISM: Homo sapiens

<400> SEQUENCE: 20

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Phe
            20                  25                  30

Tyr Ile His Trp Val Arg Gln Ala Pro Gly Lys Gly Leu Glu Trp Met
        35                  40                  45

Gly Trp Ile Phe His Gly Ser Asp Asn Thr Glu Tyr Asn Glu Lys Phe
    50                  55                  60

Arg Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Arg Trp Gly Pro His Trp Tyr Phe Asp Val Trp Gly Gln Gly Thr
            100                 105                 110

Leu Val Ser Val Ser Ser
            115

<210> SEQ ID NO 21
<211> LENGTH: 16
<212> TYPE: PRT

<213> ORGANISM: Homo sapiens
<220> FEATURE:
<221> NAME/KEY: misc_feature
<223> OTHER INFORMATION: X is L or I
<220> FEATURE:
<221> NAME/KEY: misc_feature
<222> LOCATION: (6)..(6)
<223> OTHER INFORMATION: Xaa can be any naturally occurring amino acid

<400> SEQUENCE: 21

Arg Thr Ser Lys Ser Xaa Leu Tyr Ser Asn Gly Ile Thr Tyr Leu Tyr
1               5                   10                  15

<210> SEQ ID NO 22
<211> LENGTH: 16
<212> TYPE: PRT
<213> ORGANISM: Homo sapiens
<220> FEATURE:
<221> NAME/KEY: misc_feature
<223> OTHER INFORMATION: X is L or S
<220> FEATURE:
<221> NAME/KEY: misc_feature
<222> LOCATION: (7)..(7)
<223> OTHER INFORMATION: Xaa can be any naturally occurring amino acid

<400> SEQUENCE: 22

Arg Thr Ser Lys Ser Leu Xaa Tyr Ser Asn Gly Ile Thr Tyr Leu Tyr
1               5                   10                  15

<210> SEQ ID NO 23
<211> LENGTH: 16
<212> TYPE: PRT
<213> ORGANISM: Homo sapiens
<220> FEATURE:
<221> NAME/KEY: misc_feature
<223> OTHER INFORMATION: X is T or S
<220> FEATURE:
<221> NAME/KEY: misc_feature
<222> LOCATION: (13)..(13)
<223> OTHER INFORMATION: Xaa can be any naturally occurring amino acid

<400> SEQUENCE: 23

Arg Thr Ser Lys Ser Leu Leu Tyr Ser Asn Gly Ile Xaa Tyr Leu Tyr
1               5                   10                  15

<210> SEQ ID NO 24
<211> LENGTH: 16
<212> TYPE: PRT
<213> ORGANISM: Homo sapiens
<220> FEATURE:
<221> NAME/KEY: misc_feature
<223> OTHER INFORMATION: X is L or A
<220> FEATURE:
<221> NAME/KEY: misc_feature
<222> LOCATION: (15)..(15)
<223> OTHER INFORMATION: Xaa can be any naturally occurring amino acid

<400> SEQUENCE: 24

Arg Thr Ser Lys Ser Leu Leu Tyr Ser Asn Gly Ile Thr Tyr Xaa Tyr
1               5                   10                  15

<210> SEQ ID NO 25
<211> LENGTH: 7
<212> TYPE: PRT
<213> ORGANISM: Homo sapiens
<220> FEATURE:
<221> NAME/KEY: misc_feature
<223> OTHER INFORMATION: X is S or T
<220> FEATURE:
<221> NAME/KEY: misc_feature
<222> LOCATION: (3)..(3)
<223> OTHER INFORMATION: Xaa can be any naturally occurring amino acid

```
<400> SEQUENCE: 25

Gln Met Xaa Asn Leu Ala Ser
1               5

<210> SEQ ID NO 26
<211> LENGTH: 7
<212> TYPE: PRT
<213> ORGANISM: Homo sapiens
<220> FEATURE:
<221> NAME/KEY: misc_feature
<223> OTHER INFORMATION: X is N, S, K, or Q
<220> FEATURE:
<221> NAME/KEY: misc_feature
<222> LOCATION: (4)..(4)
<223> OTHER INFORMATION: Xaa can be any naturally occurring amino acid

<400> SEQUENCE: 26

Gln Met Ser Xaa Leu Ala Ser
1               5

<210> SEQ ID NO 27
<211> LENGTH: 7
<212> TYPE: PRT
<213> ORGANISM: Homo sapiens
<220> FEATURE:
<221> NAME/KEY: misc_feature
<223> OTHER INFORMATION: X is L or R
<220> FEATURE:
<221> NAME/KEY: misc_feature
<222> LOCATION: (5)..(5)
<223> OTHER INFORMATION: Xaa can be any naturally occurring amino acid

<400> SEQUENCE: 27

Gln Met Ser Asn Xaa Ala Ser
1               5

<210> SEQ ID NO 28
<211> LENGTH: 8
<212> TYPE: PRT
<213> ORGANISM: Homo sapiens
<220> FEATURE:
<221> NAME/KEY: misc_feature
<223> OTHER INFORMATION: X is Q or A
<220> FEATURE:
<221> NAME/KEY: misc_feature
<222> LOCATION: (2)..(2)
<223> OTHER INFORMATION: Xaa can be any naturally occurring amino acid

<400> SEQUENCE: 28

Ala Xaa Asn Leu Glu Val Pro Trp
1               5

<210> SEQ ID NO 29
<211> LENGTH: 17
<212> TYPE: PRT
<213> ORGANISM: Homo sapiens
<220> FEATURE:
<221> NAME/KEY: misc_feature
<223> OTHER INFORMATION: X is N or S
<220> FEATURE:
<221> NAME/KEY: misc_feature
<222> LOCATION: (2)..(2)
<223> OTHER INFORMATION: Xaa can be any naturally occurring amino acid

<400> SEQUENCE: 29

Ile Xaa Pro Asp Ser Ser Thr Ile Asn Tyr Thr Pro Ser Leu Lys Asp
1               5                   10                  15

Lys
```

```
<210> SEQ ID NO 30
<211> LENGTH: 17
<212> TYPE: PRT
<213> ORGANISM: Homo sapiens
<220> FEATURE:
<221> NAME/KEY: misc_feature
<223> OTHER INFORMATION: X is S or E
<220> FEATURE:
<221> NAME/KEY: misc_feature
<222> LOCATION: (5)..(5)
<223> OTHER INFORMATION: Xaa can be any naturally occurring amino acid

<400> SEQUENCE: 30

Ile Asn Pro Asp Xaa Ser Thr Ile Asn Tyr Thr Pro Ser Leu Lys Asp
1               5                   10                  15

Lys

<210> SEQ ID NO 31
<211> LENGTH: 17
<212> TYPE: PRT
<213> ORGANISM: Homo sapiens
<220> FEATURE:
<221> NAME/KEY: misc_feature
<223> OTHER INFORMATION: X is T, N, K, or R
<220> FEATURE:
<221> NAME/KEY: misc_feature
<222> LOCATION: (7)..(7)
<223> OTHER INFORMATION: Xaa can be any naturally occurring amino acid

<400> SEQUENCE: 31

Ile Asn Pro Asp Ser Ser Xaa Ile Asn Tyr Thr Pro Ser Leu Lys Asp
1               5                   10                  15

Lys

<210> SEQ ID NO 32
<211> LENGTH: 17
<212> TYPE: PRT
<213> ORGANISM: Homo sapiens
<220> FEATURE:
<221> NAME/KEY: misc_feature
<223> OTHER INFORMATION: X is I, K or T
<220> FEATURE:
<221> NAME/KEY: misc_feature
<222> LOCATION: (8)..(8)
<223> OTHER INFORMATION: Xaa can be any naturally occurring amino acid

<400> SEQUENCE: 32

Ile Asn Pro Asp Ser Ser Thr Xaa Asn Tyr Thr Pro Ser Leu Lys Asp
1               5                   10                  15

Lys

<210> SEQ ID NO 33
<211> LENGTH: 17
<212> TYPE: PRT
<213> ORGANISM: Homo sapiens
<220> FEATURE:
<221> NAME/KEY: misc_feature
<223> OTHER INFORMATION: X is L or V
<220> FEATURE:
<221> NAME/KEY: misc_feature
<222> LOCATION: (14)..(14)
<223> OTHER INFORMATION: Xaa can be any naturally occurring amino acid

<400> SEQUENCE: 33

Ile Asn Pro Asp Ser Ser Thr Ile Asn Tyr Thr Pro Ser Xaa Lys Asp
1               5                   10                  15

Lys
```

```
<210> SEQ ID NO 34
<211> LENGTH: 17
<212> TYPE: PRT
<213> ORGANISM: Homo sapiens
<220> FEATURE:
<221> NAME/KEY: misc_feature
<223> OTHER INFORMATION: X is K or R
<220> FEATURE:
<221> NAME/KEY: misc_feature
<222> LOCATION: (17)..(17)
<223> OTHER INFORMATION: Xaa can be any naturally occurring amino acid

<400> SEQUENCE: 34

Ile Asn Pro Asp Ser Ser Thr Ile Asn Tyr Thr Pro Ser Leu Lys Asp
 1               5                  10                  15

Xaa

<210> SEQ ID NO 35
<211> LENGTH: 8
<212> TYPE: PRT
<213> ORGANISM: Homo sapiens
<220> FEATURE:
<221> NAME/KEY: misc_feature
<223> OTHER INFORMATION: X is F or Y
<220> FEATURE:
<221> NAME/KEY: misc_feature
<222> LOCATION: (1)..(1)
<223> OTHER INFORMATION: Xaa can be any naturally occurring amino acid

<400> SEQUENCE: 35

Xaa Glu Ile Ser Ser Leu Lys Ser
 1               5

<210> SEQ ID NO 36
<211> LENGTH: 8
<212> TYPE: PRT
<213> ORGANISM: Homo sapiens
<220> FEATURE:
<221> NAME/KEY: misc_feature
<223> OTHER INFORMATION: X is I, A or D
<220> FEATURE:
<221> NAME/KEY: misc_feature
<222> LOCATION: (3)..(3)
<223> OTHER INFORMATION: Xaa can be any naturally occurring amino acid

<400> SEQUENCE: 36

Phe Glu Xaa Ser Ser Leu Lys Ser
 1               5

<210> SEQ ID NO 37
<211> LENGTH: 7
<212> TYPE: PRT
<213> ORGANISM: Homo sapiens
<220> FEATURE:
<221> NAME/KEY: misc_feature
<223> OTHER INFORMATION: X is T or S
<220> FEATURE:
<221> NAME/KEY: misc_feature
<222> LOCATION: (2)..(2)
<223> OTHER INFORMATION: Xaa can be any naturally occurring amino acid

<400> SEQUENCE: 37

Phe Xaa Asn Phe Tyr Ile His
 1               5

<210> SEQ ID NO 38
<211> LENGTH: 7
<212> TYPE: PRT
<213> ORGANISM: Homo sapiens
<220> FEATURE:
```

```
<221> NAME/KEY: misc_feature
<223> OTHER INFORMATION: X is N or D
<220> FEATURE:
<221> NAME/KEY: misc_feature
<222> LOCATION: (3)..(3)
<223> OTHER INFORMATION: Xaa can be any naturally occurring amino acid

<400> SEQUENCE: 38

Phe Thr Xaa Phe Tyr Ile His
1               5

<210> SEQ ID NO 39
<211> LENGTH: 7
<212> TYPE: PRT
<213> ORGANISM: Homo sapiens
<220> FEATURE:
<221> NAME/KEY: misc_feature
<223> OTHER INFORMATION: X is F or L
<220> FEATURE:
<221> NAME/KEY: misc_feature
<222> LOCATION: (4)..(4)
<223> OTHER INFORMATION: Xaa can be any naturally occurring amino acid

<400> SEQUENCE: 39

Phe Thr Asn Xaa Tyr Ile His
1               5

<210> SEQ ID NO 40
<211> LENGTH: 7
<212> TYPE: PRT
<213> ORGANISM: Homo sapiens
<220> FEATURE:
<221> NAME/KEY: misc_feature
<223> OTHER INFORMATION: X is I, M or V
<220> FEATURE:
<221> NAME/KEY: misc_feature
<222> LOCATION: (6)..(6)
<223> OTHER INFORMATION: Xaa can be any naturally occurring amino acid

<400> SEQUENCE: 40

Phe Thr Asn Phe Tyr Xaa His
1               5

<210> SEQ ID NO 41
<211> LENGTH: 13
<212> TYPE: PRT
<213> ORGANISM: Homo sapiens
<220> FEATURE:
<221> NAME/KEY: misc_feature
<223> OTHER INFORMATION: X is I or F
<220> FEATURE:
<221> NAME/KEY: misc_feature
<222> LOCATION: (2)..(2)
<223> OTHER INFORMATION: Xaa can be any naturally occurring amino acid

<400> SEQUENCE: 41

Trp Xaa Phe His Gly Ser Asp Asn Thr Glu Tyr Asn Glu
1               5                   10

<210> SEQ ID NO 42
<211> LENGTH: 13
<212> TYPE: PRT
<213> ORGANISM: Homo sapiens
<220> FEATURE:
<221> NAME/KEY: misc_feature
<223> OTHER INFORMATION: X is E or Q
<220> FEATURE:
<221> NAME/KEY: misc_feature
<222> LOCATION: (13)..(13)
<223> OTHER INFORMATION: Xaa can be any naturally occurring amino acid

<400> SEQUENCE: 42
```

```
Trp Ile Phe His Gly Ser Asp Asn Thr Glu Tyr Asn Xaa
1               5                   10
```

```
<210> SEQ ID NO 43
<211> LENGTH: 9
<212> TYPE: PRT
<213> ORGANISM: Homo sapiens
<220> FEATURE:
<221> NAME/KEY: misc_feature
<223> OTHER INFORMATION: X is Y or A
<220> FEATURE:
<221> NAME/KEY: misc_feature
<222> LOCATION: (7)..(7)
<223> OTHER INFORMATION: Xaa can be any naturally occurring amino acid

<400> SEQUENCE: 43

Arg Trp Gly Pro His Trp Xaa Phe Asp
1               5
```

```
<210> SEQ ID NO 44
<211> LENGTH: 9
<212> TYPE: PRT
<213> ORGANISM: Homo sapiens
<220> FEATURE:
<221> NAME/KEY: misc_feature
<223> OTHER INFORMATION: X if F or K
<220> FEATURE:
<221> NAME/KEY: misc_feature
<222> LOCATION: (8)..(8)
<223> OTHER INFORMATION: Xaa can be any naturally occurring amino acid

<400> SEQUENCE: 44

Arg Trp Gly Pro His Trp Tyr Xaa Asp
1               5
```

```
<210> SEQ ID NO 45
<211> LENGTH: 113
<212> TYPE: PRT
<213> ORGANISM: Homo sapiens

<400> SEQUENCE: 45

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu Tyr Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Val Pro Trp Thr Phe Gly Gly Gly Thr Lys Leu Glu Ile Lys
            100                 105                 110

Arg
```

```
<210> SEQ ID NO 46
<211> LENGTH: 107
<212> TYPE: PRT
<213> ORGANISM: Homo sapiens

<400> SEQUENCE: 46

Asp Ile Gln Met Thr Gln Ser Pro Ser Ser Leu Ser Ala Ser Val Gly
```

```
                1               5                  10                 15
Asp Arg Val Thr Ile Thr Cys Arg Thr Ser Gln Ser Ile Ser Ser Tyr
                20                 25                 30

Leu Asn Trp Tyr Gln Gln Lys Pro Gly Lys Ala Pro Lys Leu Leu Ile
            35                 40                 45

Tyr Ala Ala Ser Ser Leu Gln Ser Gly Val Pro Ser Arg Phe Ser Gly
    50                 55                 60

Ser Gly Ser Gly Thr Asp Phe Thr Leu Thr Ile Ser Ser Leu Gln Pro
65                 70                 75                 80

Glu Asp Phe Ala Thr Tyr Tyr Cys Gln Gln Ser Tyr Ser Ala Pro Arg
                85                 90                 95

Thr Phe Gly Gln Gly Thr Lys Val Glu Ile Lys
                100                105

<210> SEQ ID NO 47
<211> LENGTH: 114
<212> TYPE: PRT
<213> ORGANISM: Homo sapiens

<400> SEQUENCE: 47

Gln Ser Val Leu Thr Gln Pro Pro Ser Val Ser Ala Ala Pro Gly Gln
1               5                  10                 15

Lys Val Thr Ile Ser Cys Ser Gly Ser Thr Ser Asn Ile Gly Asn Asn
                20                 25                 30

Tyr Val Ser Trp Tyr Gln Gln His Pro Gly Lys Ala Pro Lys Leu Met
            35                 40                 45

Ile Tyr Asp Val Ser Lys Arg Pro Ser Gly Val Pro Asp Arg Phe Ser
    50                 55                 60

Gly Ser Lys Ser Gly Asn Ser Ala Ser Leu Asp Ile Ser Gly Leu Gln
65                 70                 75                 80

Ser Glu Asp Glu Ala Asp Tyr Tyr Cys Ala Ala Trp Asp Asp Ser Leu
                85                 90                 95

Ser Glu Phe Leu Phe Gly Thr Gly Thr Lys Leu Thr Val Leu Gly Gln
                100                105                110

Pro Lys

<210> SEQ ID NO 48
<211> LENGTH: 108
<212> TYPE: PRT
<213> ORGANISM: Homo sapiens

<400> SEQUENCE: 48

Glu Leu Thr Gln Pro Pro Ser Val Ser Val Ser Pro Gly Gln Thr Ala
1               5                  10                 15

Arg Ile Thr Cys Ser Ala Asn Ala Leu Pro Asn Gln Tyr Ala Tyr Trp
                20                 25                 30

Tyr Gln Gln Lys Pro Gly Arg Ala Pro Val Met Val Ile Tyr Lys Asp
            35                 40                 45

Thr Gln Arg Pro Ser Gly Ile Pro Gln Arg Phe Ser Ser Ser Thr Ser
    50                 55                 60

Gly Thr Thr Val Thr Leu Thr Ile Ser Gly Val Gln Ala Glu Asp Glu
65                 70                 75                 80

Ala Asp Tyr Tyr Cys Gln Ala Trp Asp Asn Ser Ala Ser Ile Phe Gly
                85                 90                 95

Gly Gly Thr Lys Leu Thr Val Leu Gly Gln Pro Lys
                100                105
```

<210> SEQ ID NO 49
<211> LENGTH: 117
<212> TYPE: PRT
<213> ORGANISM: Homo sapiens

<400> SEQUENCE: 49

```
Glu Val Lys Leu Leu Glu Ser Gly Gly Gly Leu Val Gln Pro Gly Gly
1               5                   10                  15

Ser Gln Lys Leu Ser Cys Ala Ala Ser Gly Phe Asp Phe Ser Gly Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Glu Thr Gly Thr Arg Phe Asp Tyr Trp Gly Gln Gly Thr Thr
            100                 105                 110

Leu Thr Val Ser Ser
        115
```

<210> SEQ ID NO 50
<211> LENGTH: 120
<212> TYPE: PRT
<213> ORGANISM: Homo sapiens

<400> SEQUENCE: 50

```
Gln Val Gln Leu Val Glu Ser Gly Gly Gly Val Val Gln Pro Gly Lys
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Leu Ile Ser Tyr Asp Glu Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Lys Phe Tyr Asp Pro Thr Ala Pro Asn Asp Tyr Trp Gly
            100                 105                 110

Gln Gly Thr Leu Val Thr Val Ser
        115                 120
```

<210> SEQ ID NO 51
<211> LENGTH: 120
<212> TYPE: PRT
<213> ORGANISM: Homo sapiens

<400> SEQUENCE: 51

```
Gly Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45
```

```
Ala Ile Ile Ser Tyr Asp Gly Ser Lys Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ser Ile Ala Ala Ala Arg Val Leu Asp Tyr Trp Gly Arg
            100                 105                 110

Gly Thr Met Val Thr Val Ser Ser
            115                 120

<210> SEQ ID NO 52
<211> LENGTH: 121
<212> TYPE: PRT
<213> ORGANISM: Homo sapiens

<400> SEQUENCE: 52

Ala Val Lys Leu Val Gln Ala Gly Gly Val Val Gln Pro Gly Arg
1               5                   10                  15

Ser Leu Arg Leu Ser Cys Ile Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asn Gly Ser Arg Thr Tyr Tyr Gly Asp Ser Val
    50                  55                  60

Lys Gly Arg Phe Thr Ile Ser Arg Asp Asn Ser Lys Arg Thr Leu Tyr
65                  70                  75                  80

Met Gln Met Asn Ser Leu Arg Thr Glu Asp Thr Ala Val Tyr Tyr Cys
                85                  90                  95

Ala Arg Asp Pro Asp Ile Leu Thr Ala Phe Ser Phe Asp Tyr Trp Gly
            100                 105                 110

Gln Gly Val Leu Val Thr Val Ser Ser
            115                 120

<210> SEQ ID NO 53
<211> LENGTH: 12
<212> TYPE: PRT
<213> ORGANISM: Homo sapiens

<400> SEQUENCE: 53

Cys Ser Ala Ser Ser Ser Val Ser Tyr Met His Trp
1               5                   10

<210> SEQ ID NO 54
<211> LENGTH: 12
<212> TYPE: PRT
<213> ORGANISM: Homo sapiens

<400> SEQUENCE: 54

Cys Arg Ala Ser Ser Ser Val Thr Tyr Ile His Trp
1               5                   10

<210> SEQ ID NO 55
<211> LENGTH: 9
<212> TYPE: PRT
<213> ORGANISM: Homo sapiens

<400> SEQUENCE: 55

Phe Glu Ile Ser Lys Leu Ala Ser Gly
1               5
```

```
<210> SEQ ID NO 56
<211> LENGTH: 9
<212> TYPE: PRT
<213> ORGANISM: Homo sapiens

<400> SEQUENCE: 56

Tyr Ala Thr Ser Asn Leu Ala Ser Gly
1               5

<210> SEQ ID NO 57
<211> LENGTH: 9
<212> TYPE: PRT
<213> ORGANISM: Homo sapiens

<400> SEQUENCE: 57

Tyr Ala Ala Ser Ser Leu Gln Ser Gly
1               5

<210> SEQ ID NO 58
<211> LENGTH: 9
<212> TYPE: PRT
<213> ORGANISM: Homo sapiens

<400> SEQUENCE: 58

Tyr Asp Ala Ser Ser Arg Ala Thr Gly
1               5

<210> SEQ ID NO 59
<211> LENGTH: 9
<212> TYPE: PRT
<213> ORGANISM: Homo sapiens

<400> SEQUENCE: 59

Tyr Gly Ala Ser Thr Arg Ala Thr Gly
1               5

<210> SEQ ID NO 60
<211> LENGTH: 11
<212> TYPE: PRT
<213> ORGANISM: Homo sapiens

<400> SEQUENCE: 60

Gly Tyr Ser Phe Thr Asn Phe Tyr Ile His Trp
1               5                   10

<210> SEQ ID NO 61
<211> LENGTH: 12
<212> TYPE: PRT
<213> ORGANISM: Homo sapiens

<400> SEQUENCE: 61

Ser Gly Tyr Arg Phe Ser Asn Phe Val Ile His Trp
1               5                   10

<210> SEQ ID NO 62
<211> LENGTH: 12
<212> TYPE: PRT
<213> ORGANISM: Homo sapiens

<400> SEQUENCE: 62

Ser Gly Tyr Asn Phe Thr Ser Tyr Trp Ile Asn Trp
1               5                   10

<210> SEQ ID NO 63
```

```
<211> LENGTH: 12
<212> TYPE: PRT
<213> ORGANISM: Homo sapiens

<400> SEQUENCE: 63

Ser Gly Tyr Thr Phe Thr Asp Tyr Tyr Ile Asn Trp
1               5                   10

<210> SEQ ID NO 64
<211> LENGTH: 12
<212> TYPE: PRT
<213> ORGANISM: Homo sapiens

<400> SEQUENCE: 64

Ser Gly Tyr Thr Phe Ser Asp Phe Tyr Met Tyr Trp
1               5                   10

<210> SEQ ID NO 65
<211> LENGTH: 12
<212> TYPE: PRT
<213> ORGANISM: Homo sapiens

<400> SEQUENCE: 65

Gly Phe Thr Phe Thr Asp Tyr Tyr Met Asn Trp Val
1               5                   10

<210> SEQ ID NO 66
<211> LENGTH: 12
<212> TYPE: PRT
<213> ORGANISM: Homo sapiens

<400> SEQUENCE: 66

Ser Gly Tyr Ser Phe Thr Ser Tyr Gly Leu His Trp
1               5                   10

<210> SEQ ID NO 67
<211> LENGTH: 20
<212> TYPE: PRT
<213> ORGANISM: Homo sapiens

<400> SEQUENCE: 67

Trp Ile Phe His Gly Ser Asp Asn Thr Glu Tyr Asn Glu Lys Phe Lys
1               5                   10                  15

Asp Lys Ala Thr
            20

<210> SEQ ID NO 68
<211> LENGTH: 21
<212> TYPE: PRT
<213> ORGANISM: Homo sapiens

<400> SEQUENCE: 68

Gly Gly Val Ile Pro Leu Leu Thr Ile Thr Asn Tyr Ala Pro Arg Phe
1               5                   10                  15

Gln Gly Arg Ile Thr
            20

<210> SEQ ID NO 69
<211> LENGTH: 22
<212> TYPE: PRT
<213> ORGANISM: Homo sapiens

<400> SEQUENCE: 69

Ala Val Ile Ser Ser Asp Gly Gly Asn Lys Tyr Tyr Thr Asp Ser Val
1               5                   10                  15
```

```
Lys Gly Arg Phe Thr Ile
            20

<210> SEQ ID NO 70
<211> LENGTH: 22
<212> TYPE: PRT
<213> ORGANISM: Homo sapiens

<400> SEQUENCE: 70

Ser Gly Val Phe Gly Ser Gly Asn Thr Asp Tyr Ala Asp Ala Val
1               5                   10                  15

Lys Gly Arg Phe Thr Ile
            20

<210> SEQ ID NO 71
<211> LENGTH: 22
<212> TYPE: PRT
<213> ORGANISM: Homo sapiens

<400> SEQUENCE: 71

Gly Asp Ile Tyr Pro Gly Ser Gly Ile Thr Asn Tyr Asn Glu Lys Phe
1               5                   10                  15

Lys Ser Lys Ala Thr Leu
            20

<210> SEQ ID NO 72
<211> LENGTH: 13
<212> TYPE: PRT
<213> ORGANISM: Homo sapiens

<400> SEQUENCE: 72

Cys Ala Arg Trp Gly Pro His Trp Tyr Phe Asp Val Trp
1               5                   10

<210> SEQ ID NO 73
<211> LENGTH: 14
<212> TYPE: PRT
<213> ORGANISM: Homo sapiens

<400> SEQUENCE: 73

Cys Ala Ala Asp Pro Trp Glu Leu Asn Ala Phe Asn Val Trp
1               5                   10

<210> SEQ ID NO 74
<211> LENGTH: 24
<212> TYPE: PRT
<213> ORGANISM: Homo sapiens

<400> SEQUENCE: 74

Cys Thr Thr Asp Gly Phe Ile Met Ile Arg Gly Val Ser Glu Asp Tyr
1               5                   10                  15

Tyr Tyr Tyr Tyr Met Asp Val Trp
            20

<210> SEQ ID NO 75
<211> LENGTH: 26
<212> TYPE: PRT
<213> ORGANISM: Homo sapiens

<400> SEQUENCE: 75

Cys Ala His Arg Arg Gly Pro Thr Thr Leu Ala Ala Ala Ala Ala Ala
1               5                   10                  15

Ala Gly Pro Val Asn Ala Met Asp Val Trp
```

<210> SEQ ID NO 76
<211> LENGTH: 21
<212> TYPE: PRT
<213> ORGANISM: Homo sapiens

<400> SEQUENCE: 76

Cys Val Lys Gly Arg Asp Tyr Tyr Asp Ser Gly Gly Tyr Phe Thr Val
1               5                   10                  15

Ala Phe Asp Ile Trp
            20

<210> SEQ ID NO 77
<211> LENGTH: 18
<212> TYPE: PRT
<213> ORGANISM: Homo sapiens

<400> SEQUENCE: 77

Cys Ala Arg Lys Gly Ser Asp Arg Leu Ser Asp Asn Asp Pro Phe Asp
1               5                   10                  15

Ala Trp

<210> SEQ ID NO 78
<211> LENGTH: 105
<212> TYPE: PRT
<213> ORGANISM: Homo sapiens

<400> SEQUENCE: 78

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Ser Tyr Ile
            20                  25                  30

His Trp Tyr Gln Gln Lys Pro Gly Arg Ala Pro Lys Pro Leu Met Tyr
        35                  40                  45

Glu Ala Ser Ser Arg Ala Thr Gly Val Pro Ser Arg Phe Ser Gly Ser
    50                  55                  60

Gly Ser Gly Thr Glu Tyr Thr Leu Thr Ile Ser Ser Leu Gln Ser Asp
65                  70                  75                  80

Asp Phe Ala Thr Tyr Tyr Cys Gln Gln Trp Asn Tyr Pro Phe Thr Phe
                85                  90                  95

Gly Gln Gly Thr Lys Leu Glu Ile Lys
            100                 105

<210> SEQ ID NO 79
<211> LENGTH: 105
<212> TYPE: PRT
<213> ORGANISM: Homo sapiens

<400> SEQUENCE: 79

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Ser Tyr Ile
            20                  25                  30

His Trp Tyr Gln Gln Lys Pro Gly Arg Ala Pro Lys Pro Leu Met Tyr
        35                  40                  45

Glu Ala Ser Ser Arg Ala Thr Gly Val Pro Ser Arg Phe Ser Gly Ser
    50                  55                  60

Gly Ser Gly Thr Glu Tyr Thr Leu Thr Ile Ser Ser Leu Gln Ser Asp
65                  70                  75                  80

Asp Phe Ala Thr Tyr Tyr Cys Gln Gln Trp Asn Tyr Pro Phe Thr Phe
                85                  90                  95

Gly Gln Gly Thr Lys Leu Glu Ile Lys
            100                 105

<210> SEQ ID NO 80
<211> LENGTH: 105
<212> TYPE: PRT
<213> ORGANISM: Homo sapiens

<400> SEQUENCE: 80

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Ser Tyr Ile
                20                  25                  30

His Trp Tyr Gln Gln Lys Pro Gly Arg Ala Pro Lys Pro Leu Met Tyr
            35                  40                  45

Glu Ala Ser Ser Arg Ala Thr Gly Val Pro Ser Arg Phe Ser Gly Ser
        50                  55                  60

Gly Ser Gly Thr Glu Tyr Thr Leu Thr Ile Ser Ser Leu Gln Ser Asp
65                  70                  75                  80

Asp Phe Ala Thr Tyr Tyr Cys Gln Gln Trp Asn Tyr Pro Phe Thr Phe
                85                  90                  95

Gly Gln Gly Thr Lys Leu Glu Ile Lys
            100                 105

<210> SEQ ID NO 81
<211> LENGTH: 105
<212> TYPE: PRT
<213> ORGANISM: Homo sapiens

<400> SEQUENCE: 81

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Ser Tyr Ile
                20                  25                  30

His Trp Tyr Gln Gln Lys Pro Gly Arg Ala Pro Lys Pro Leu Met Tyr
            35                  40                  45

Glu Thr Ser Asn Leu Ala Ser Gly Val Pro Ser Arg Phe Ser Gly Ser
        50                  55                  60

Gly Ser Gly Thr Glu Tyr Thr Leu Thr Ile Ser Ser Leu Gln Ser Asp
65                  70                  75                  80

Asp Phe Ala Thr Tyr Tyr Cys Gln Gln Trp Asn Tyr Pro Phe Thr Phe
                85                  90                  95

Gly Gln Gly Thr Lys Leu Glu Ile Lys
            100                 105

<210> SEQ ID NO 82
<211> LENGTH: 105
<212> TYPE: PRT
<213> ORGANISM: Homo sapiens

<400> SEQUENCE: 82

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Ser Tyr Ile
                20                  25                  30

His Trp Tyr Gln Gln Lys Pro Gly Arg Ala Pro Lys Pro Leu Met Tyr

```
                 35                  40                  45
Glu Thr Ser Asn Leu Ala Ser Gly Val Pro Ser Arg Phe Ser Gly Ser
 50                  55                  60
Gly Ser Gly Thr Glu Tyr Thr Leu Thr Ile Ser Ser Leu Gln Ser Asp
 65                  70                  75                  80
Asp Phe Ala Thr Tyr Tyr Cys Gln Gln Trp Asn Tyr Pro Phe Thr Phe
                 85                  90                  95
Gly Gln Gly Thr Lys Leu Glu Ile Lys
            100                 105

<210> SEQ ID NO 83
<211> LENGTH: 105
<212> TYPE: PRT
<213> ORGANISM: Homo sapiens

<400> SEQUENCE: 83

Asp Ile Gln Met Thr Gln Ser Pro Ser Thr Leu Ser Ala Ser Val Gly
  1               5                  10                  15
Asp Arg Val Thr Ile Thr Cys Arg Ala Ser Ser Ser Val Ser Tyr Ile
                 20                  25                  30
His Trp Tyr Gln Gln Lys Pro Gly Arg Ala Pro Lys Pro Leu Met Tyr
                 35                  40                  45
Glu Thr Ser Asn Leu Ala Ser Gly Val Pro Ser Arg Phe Ser Gly Ser
 50                  55                  60
Gly Ser Gly Thr Glu Tyr Thr Leu Thr Ile Ser Ser Leu Gln Ser Asp
 65                  70                  75                  80
Asp Phe Ala Thr Tyr Tyr Cys Gln Gln Trp Asn Tyr Pro Phe Thr Phe
                 85                  90                  95
Gly Gln Gly Thr Lys Leu Glu Ile Lys
            100                 105

<210> SEQ ID NO 84
<211> LENGTH: 105
<212> TYPE: PRT
<213> ORGANISM: Homo sapiens

<400> SEQUENCE: 84

Asp Ile Gln Met Thr Gln Ser Pro Ser Thr Leu Ser Ala Ser Val Gly
  1               5                  10                  15
Asp Arg Val Thr Ile Thr Cys Arg Ala Ser Ser Ser Val Ser Tyr Ile
                 20                  25                  30
His Trp Tyr Gln Gln Lys Pro Gly Arg Ala Pro Lys Pro Leu Met Tyr
                 35                  40                  45
Glu Thr Ser Asn Leu Ala Ser Gly Val Pro Ser Arg Phe Ser Gly Ser
 50                  55                  60
Gly Ser Gly Thr Glu Tyr Thr Leu Thr Ile Ser Ser Leu Gln Ser Asp
 65                  70                  75                  80
Asp Phe Ala Thr Tyr Tyr Cys Gln Gln Trp Asn Tyr Pro Phe Thr Phe
                 85                  90                  95
Gly Gln Gly Thr Lys Leu Glu Ile Lys
            100                 105

<210> SEQ ID NO 85
<211> LENGTH: 105
<212> TYPE: PRT
<213> ORGANISM: Homo sapiens

<400> SEQUENCE: 85
```

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Ser Tyr Ile
            20                  25                  30

His Trp Tyr Gln Gln Lys Pro Gly Arg Ala Pro Lys Pro Leu Met Tyr
        35                  40                  45

Glu Ala Ser Ser Arg Ala Thr Gly Val Pro Ser Arg Phe Ser Gly Ser
    50                  55                  60

Gly Ser Gly Thr Glu Tyr Thr Leu Thr Ile Ser Ser Leu Gln Ser Asp
65              70                  75                  80

Asp Phe Ala Thr Tyr Tyr Cys Gln Gln Trp Asn Tyr Pro Phe Thr Phe
            85                  90                  95

Gly Gln Gly Thr Lys Leu Glu Ile Lys
            100                 105

<210> SEQ ID NO 86
<211> LENGTH: 117
<212> TYPE: PRT
<213> ORGANISM: Homo sapiens

<400> SEQUENCE: 86

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Ile
        35                  40                  45

Gly Trp Ile Phe His Gly Ser Asp Asn Thr Glu Tyr Asn Asp Ala Val
    50                  55                  60

Lys Gly Arg Phe Ser Ile Thr Ala Asp Glu Ser Thr Ser Thr Ala Tyr
65              70                  75                  80

Met Glu Leu Ser Ser Leu Arg Ser Glu Asp Thr Ala Val Phe Tyr Cys
            85                  90                  95

Ala Arg Trp Gly Pro His Trp Tyr Phe Asp Ala Trp Gly Arg Gly Thr
        100                 105                 110

Leu Val Thr Val Ser
        115

<210> SEQ ID NO 87
<211> LENGTH: 117
<212> TYPE: PRT
<213> ORGANISM: Homo sapiens

<400> SEQUENCE: 87

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Ile
        35                  40                  45

Gly Trp Ile Phe His Gly Ser Asp Asn Thr Glu Tyr Asn Glu Lys Phe
    50                  55                  60

Lys Ser Lys Ala Thr Ile Thr Ala Asp Glu Ser Thr Ser Thr Ala Tyr
65              70                  75                  80

Met Glu Leu Ser Ser Leu Arg Ser Glu Asp Thr Ala Val Phe Tyr Cys
            85                  90                  95

Ala Arg Trp Gly Pro His Trp Tyr Phe Asp Ala Trp Gly Arg Gly Thr

Leu Val Thr Val Ser
        115

<210> SEQ ID NO 88
<211> LENGTH: 117
<212> TYPE: PRT
<213> ORGANISM: Homo sapiens

<400> SEQUENCE: 88

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Arg Phe Ser Asn Phe
            20                  25                  30

Tyr Ile His Trp Val Arg Gln Ala Pro Gly Gln Gly Leu Glu Trp Ile
        35                  40                  45

Gly Trp Ile Phe His Gly Ser Asp Asn Thr Glu Tyr Asn Glu Lys Phe
    50                  55                  60

Lys Ser Lys Ala Thr Ile Thr Ala Asp Glu Ser Thr Ser Thr Ala Tyr
65                  70                  75                  80

Met Glu Leu Ser Ser Leu Arg Ser Glu Asp Thr Ala Val Phe Tyr Cys
                85                  90                  95

Ala Arg Trp Gly Pro His Trp Tyr Phe Asp Ala Trp Gly Arg Gly Thr
            100                 105                 110

Leu Val Thr Val Ser
        115

<210> SEQ ID NO 89
<211> LENGTH: 117
<212> TYPE: PRT
<213> ORGANISM: Homo sapiens

<400> SEQUENCE: 89

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Ile
        35                  40                  45

Gly Trp Ile Phe His Gly Ser Asp Asn Thr Glu Tyr Asn Asp Ala Val
    50                  55                  60

Lys Gly Arg Phe Ser Ile Thr Ala Asp Glu Ser Thr Ser Thr Ala Tyr
65                  70                  75                  80

Met Glu Leu Ser Ser Leu Arg Ser Glu Asp Thr Ala Val Phe Tyr Cys
                85                  90                  95

Ala Arg Trp Gly Pro His Trp Tyr Phe Asp Ala Trp Gly Arg Gly Thr
            100                 105                 110

Leu Val Thr Val Ser
        115

<210> SEQ ID NO 90
<211> LENGTH: 117
<212> TYPE: PRT
<213> ORGANISM: Homo sapiens

<400> SEQUENCE: 90

Glu Val Gln Leu Val Gln Ser Gly Ala Glu Val Lys Lys Pro Gly Ser
1               5                   10                  15

```
Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Ile
        35                  40                  45

Gly Trp Ile Phe His Gly Ser Asp Asn Thr Glu Tyr Asn Glu Lys Phe
 50                  55                  60

Lys Ser Lys Ala Thr Ile Thr Ala Asp Glu Ser Thr Ser Thr Ala Tyr
 65                  70                  75                  80

Met Glu Leu Ser Ser Leu Arg Ser Glu Asp Thr Ala Val Phe Tyr Cys
                85                  90                  95

Ala Arg Trp Gly Pro His Trp Tyr Phe Asp Ala Trp Gly Arg Gly Thr
            100                 105                 110

Leu Val Thr Val Ser
        115

<210> SEQ ID NO 91
<211> LENGTH: 117
<212> TYPE: PRT
<213> ORGANISM: Homo sapiens

<400> SEQUENCE: 91

Glu Val Gln Leu Val Gln Ser Gly Ala Glu Val Lys Lys Pro Gly Ser
 1               5                  10                  15

Ser Val Lys Val Ser Cys Lys Ala Ser Gly Tyr Arg Phe Ser Asn Phe
            20                  25                  30

Tyr Ile His Trp Val Arg Gln Ala Pro Gly Gln Gly Leu Glu Trp Ile
        35                  40                  45

Gly Trp Ile Phe His Gly Ser Asp Asn Thr Glu Tyr Asn Asp Ala Val
 50                  55                  60

Lys Gly Arg Phe Ser Ile Thr Ala Asp Glu Ser Thr Ser Thr Ala Tyr
 65                  70                  75                  80

Met Glu Leu Ser Ser Leu Arg Ser Glu Asp Thr Ala Val Phe Tyr Cys
                85                  90                  95

Ala Arg Trp Gly Pro His Trp Tyr Phe Asp Ala Trp Gly Arg Gly Thr
            100                 105                 110

Leu Val Thr Val Ser
        115

<210> SEQ ID NO 92
<211> LENGTH: 117
<212> TYPE: PRT
<213> ORGANISM: Homo sapiens

<400> SEQUENCE: 92

Glu Val Gln Leu Val Gln Ser Gly Ala Glu Val Lys Lys Pro Gly Ser
 1               5                  10                  15

Ser Val Lys Val Ser Cys Lys Ala Ser Gly Tyr Arg Phe Ser Asn Phe
            20                  25                  30

Tyr Ile His Trp Val Arg Gln Ala Pro Gly Gln Gly Leu Glu Trp Ile
        35                  40                  45

Gly Trp Ile Phe His Gly Ser Asp Asn Thr Glu Tyr Asn Glu Lys Phe
 50                  55                  60

Lys Ser Lys Ala Thr Ile Thr Ala Asp Glu Ser Thr Ser Thr Ala Tyr
 65                  70                  75                  80

Met Glu Leu Ser Ser Leu Arg Ser Glu Asp Thr Ala Val Phe Tyr Cys
                85                  90                  95

Ala Arg Trp Gly Pro His Trp Tyr Phe Asp Ala Trp Gly Arg Gly Thr
```

```
                     100              105              110
Leu Val Thr Val Ser
            115

<210> SEQ ID NO 93
<211> LENGTH: 117
<212> TYPE: PRT
<213> ORGANISM: Homo sapiens

<400> SEQUENCE: 93

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Arg Phe Ser Asn Phe
            20                  25                  30

Tyr Ile His Trp Val Arg Gln Ala Pro Gly Gln Gly Leu Glu Trp Ile
            35                  40                  45

Gly Trp Ile Phe His Gly Ser Asp Asn Thr Glu Tyr Asn Asp Ala Val
        50                  55                  60

Lys Gly Arg Phe Ser Ile Thr Ala Asp Glu Ser Thr Ser Thr Ala Tyr
65                  70                  75                  80

Met Glu Leu Ser Ser Leu Arg Ser Glu Asp Thr Ala Val Phe Tyr Cys
                85                  90                  95

Ala Arg Trp Gly Pro His Trp Tyr Phe Asp Ala Trp Gly Arg Gly Thr
            100                 105                 110

Leu Val Thr Val Ser
            115
```

METHODS FOR HUMANIZING ANTIBODIES AND HUMANIZED ANTIBODIES MADE THEREBY

FIELD OF THE INVENTION

The present invention relates to compositions and methods for modifying antibodies. In particular, the invention relates to the use of three-dimensional structure information to guide the process of modifying antibodies with amino acids from one or more templates or surrogates such that the antigen binding properties of the parent antibody are maintained and the immunogenicity potential is reduced when administered as a therapeutic in humans.

BACKGROUND OF THE INVENTION

Antibodies in therapeutic use are being developed so they have an increased proportion of 'human' or 'humanized' features. Antibodies are composed of heterodimers of an immunoglobulin light chain and heavy chain. The two chains in combination dictate the antigen recognition properties of the antibody directed by the 'variable' regions of each chain. The antibody preserves the combinatorial recognition features to the antigen, yet may be delivered therapeutically as an altered, engineered, processed, or fragment polypeptide molecule, such as an antibody tetramer, Fab or (Fab)$_2$, or as an immunoconjugate or fusion protein with other polypeptide and chemical entities providing additional properties.

Fully human antibodies are important therapeutic proteins. In these examples, human antibodies have been formed from a number of screening methods. These features have been created by generating new human antibodies as described in the examination of phage display library screening, and the use of immunization of transgenic mouse strains with embedded human antibody genes in place of the mouse antibody genes. These methods focus on the new derivation of human antibodies with similar antigen-binding properties to the non-human antibody. In cases where comparative analysis is possible between non-human antibodies directed against an antigen with those generated by either of the above methods, it is apparent that antigen binding affinity is ordinarily reduced. In addition these methods are limited by the utilization of incomplete human repertoire and antibody maturation capacity. Therefore, these methods suffer from requirements for continued refinements by recombinant engineering methods once a functional, but unsatisfactory human antibody is identified. Furthermore, these methods make no accommodation for the acquisition of immunogenic features of the new antibodies.

Methods are also in use to transform non-human monoclonal antibodies into therapeutic proteins without derivation of a new antibody. Humanized antibodies have been described that have improved properties indicating a reduced immunoreactivity in patients, and thereby making those reagents more useful for therapy, especially in prolonged exposure to the patient. Changes to the composition of the antibody that have been utilized are 'CDR grafting', a procedure where mouse or rat monoclonal antibodies are converted to another form where human framework substitutions are combined with the rodent CDR regions by molecular engineering approaches. A refinement of this strategy involves the recruitment of human variable gene sequences. U.S. Pat. No. 6,180,370 (the entire teaching of which is incorporated herein by reference) describes humanization strategies based on DNA sequence alignment between a parent antibody and similar human variable chains as an approach to replicate the antigen binding properties of a parent non-human antibody. This method does not specify the computational techniques necessary to evaluate the atomic coordinates of the antibody subfeatures, nor does it comment on the means to influence immunogenicity of component parts of the antigen-recognition features.

Since the source of the immunogenicity of non-human antibodies in human therapeutics is recognition by the human immune system of foreign protein sequences in the antibody polypeptides, an approach to reduce immunogenicity would be to reduce the amount of non-human protein sequence in a modified antibody while retaining those protein sequences that are essential for the antigen binding specificity of the parent antibody. The first of these alterations to antibodies to be employed were termed chimeric antibodies. The modifications consisted of replacement of the constant region domains of the parent antibody chains with human constant region domains, thus reducing the amount of non-human sequence by approximately half. However, these antibodies were shown to still have significant immune liabilities in the clinic (Hwang and Foote, 2005, Methods Vol. 36, p 3-10 and references therein, the entire teachings of which are incorporated herein by reference).

Other methods were subsequently developed to remove even more of the non-human sequence from the resultant modified antibody. These antibodies were termed humanized antibodies. In the method of complementarity determining region (CDR) grafting (U.S. Pat. No. 5,225,539 and Jones et al., 1986; Nature 321:522-525, the entire teachings of which are incorporated herein by reference), only those protein sequences of the parent antibody predicted to be essential for antigen binding are retained. The identity of these CDR sequences is first predicted from biochemical and x-ray crystal structure analyses of many antibodies, mostly derived from a mouse source (Al-Lazikani et al., 1997; Journal of Molecular Biology 273:927-948, the entire teaching of which is incorporated herein by reference). There are three CDR sequences in each chain of the antibody heavy and light chains. These six CDR sequences are grafted into equivalent sequence environments in a human antibody framework. This modified humanized antibody therefore only contains parental sequence in approximately 75 amino acid residues, which is a greater reduction of non-human sequence than the chimeric antibodies. Limitations of this method were revealed because the human framework chosen in humanization of a particular antibody may not be compatible with proper folding of the parent CDR sequences. An additional problem associated with these methods is that there are significant differences between mouse and human CDR, particularly in the heavy chain CDR3 (Zemlin et al., 2003; Journal of Molecular Biology 334:733-749, the entire teaching of which is incorporated herein by reference).

The method of Queen et al. (U.S. Pat. No. 6,180,370) further refines the process of CDR grafting. In this method, the human framework antibody is chosen by sequence homology to the parent antibody. In this way, the chances of proper folding are increased in the modified construct since the residues contacting the parent CDR sequences (Vernier residues) are more likely to be the same. Other contacting residues can be identified for modification in the framework region by identification of non-conserved residues in the sequence alignment of the parent antibody and the framework antibody as well as homology modeling of the parent and framework antibodies.

An even further reduction in the amount of parent antibody sequence can be achieved by using a method called specificity determining residue (SDR) grafting (Tamura et al., 2000; J.

Immunol. 164:1432-1441, the entire teaching of which is incorporated herein by reference). In this method, CDR residues of a CDR-grafted, humanized antibody are systematically mutated and then analyzed for both ligand affinity and reactivity to sensitized sera samples. Once identified, the SDR residues important for binding are maintained, while those that are immunogenic are mutated. This method suffers from the need to experimentally identify the SDR residues.

An alternate method of reducing immunogenicity in the humanized antibody is modification of residues in the non-human antibody sequence that are predicted to be immunogenic but not critical for antigen binding based on solvent-exposed sites or folds (U.S. Pat. No. 5,869,619, the entire teaching of which is incorporated herein by reference). Others have mapped the solvent-accessible surfaces of antibodies by computer-instructed modeling (Zhang et al., 2005; Molecular Immunology 42:1445-1451, the entire teaching of which is incorporated herein by reference). These approaches have been utilized in combination with immunogenicity computer methods to delineate residues for recombinant engineering purposes.

In an alternative approach, a method (U.S. Pat. No. 6,881,557, the entire teaching of which is incorporated herein by reference) is used where the CDRs of the parent antibody are compared in amino acid sequence to candidate human CDRs to identify antibodies with most closely matched CDR loops. The residues in the human CDR region are then substituted with residues from the parent CDRs based on the linear alignments. This method is limited by the ability to match CDR epitopes without consideration of the framework residues, and does not incorporate three dimensional configurations of the CDRs.

The CDR grafting methods described above all rely on amino acid sequence information to determine which non-human residues should be grafted into the specific human acceptor antibody. Success of this technique resulting in a modified antibody with the desired antigen binding properties requires that the parental sequences are able to fold in three dimensions such that the spatial relationship of the key antigen binding residues is conserved between the parent and the modified structures. This being the case, utilizing information from the structure of the parent and potential human template antibodies should enable better decisions about which sequences from the parent antibody should be modified in the final antibody.

For instance, in the method described in U.S. Patent application 20040133357 (the entire teaching of which is incorporated herein by reference), the protein structure information of the parent antibody is solely used to guide assignment of an alignment of amino acid sequences of human antibodies. From these alignments, the amino acid variation at each position in the sequence is tabulated. Through modeling and energy minimization, the list of variants is filtered to include those variants that constitute a combinatorial library of antibody sequences. The method relies on screening for desired properties since the combinatorial libraries formed are large. Also, no structural criteria are elaborated and there is no computational refinement of this sequences based on additional protein structure considerations.

Another method utilizes homology models of the parent and human antibodies ( Luo et al., 2003: Journal of Immunological Methods 275:31-40, the entire teaching of which is incorporated herein by reference). In this method, a model was created of the murine parent as well as a human framework based on a consensus sequence used as a framework. The CDR structures in the human model were replaced by the corresponding murine model CDR structures. Through energy minimization calculations, residues important for CDR folding that were not optimized in the human framework were indicated. These residues were then altered in the model and then in the sequence to murine equivalents to improve the antigen binding properties of the modified antibody.

The structure can be even more informative if it is used to determine the exact human antibody frameworks with the best chance for successful grafting of parent CDR sequences. Yazaki et al. (Yazaki et al., 2004, Protein Engineering, Design & Selection, vol. 17, pp. 481-489, the entire teaching of which is incorporated herein by reference) outlined a structure-guided method for humanization of antibodies. Human or humanized antibody heavy chain or light chain structures that superposed well with the parental framework and CDR structures, were used as scaffolds for CDR grafting. A second filter of sequence identity was used to refine the selection, and energy minimization calculations identified residues for changes to alleviate unfavorable contacts. This method has the critical limitation of only aligning single protein chains to other single protein chains without consideration of quaternary structure. Importantly, the antigen binding site is made up from correct spatial arrangement of six CDR sequences from both the heavy and light chains. However, the structural information was not used to guide potential further reductions in the non-human sequence content of the grafted CDR.

The need for protein structure in humanization of antibodies is now evident for several reasons. Analysis of the amino acid sequences does not predict the folded protein state adequately, because small changes in the structure of the antigen binding site may result in large losses in affinity. Also, residues that are predicted to be solvent exposed may well be buried or critical for folding. It is evident that the most homologous human framework antibody by sequence alignment may not be the best scaffold for humanization. Although CDR loops superpose well in various structures when considered individually, the superposition is poor when evaluating the entire antibody chain (Bajorath et al. 1995; Journal of Biological Chemistry 270:22081-22084, the entire teaching of which is incorporated herein by reference). Further, large movements of the CDR positions arise from small changes in the junctional regions of the antibody. It is difficult to anticipate appropriate junctional residues and side chains based on sequence homology/alignment and evolutionary relatedness alone. Therefore, methods that incorporate the analysis of the three dimensional positioning of atoms in antibody variable regions will be the best representations and provide the most effective template for changes in antibody engineering. A method is needed to find the best three dimensional scaffold on which to build the antigen binding site, regardless of sequence variation.

Whereas protein structural information is a key advancement in the humanization process, improvements to the current methods are clearly necessary. A method is required that extends the current analysis in CDR grafting such that the two domains of the modified antibody are correctly oriented with respect to one another. In this way, the best human scaffold in terms of structure can be chosen for the CDR grafts, which should result in better conservation of the folded state of the CDR sequences after grafting, and improved affinity and specificity of the humanized antibody. A unifying method is needed for the consideration of the quaternary structure in the modification method in order to conserve the similarity to parent antibodies while improving the desired properties in the modified antibody. The overall folding of the modified antibody can be assumed to occur as independent elements for the framework and six CDR regions. Since the CDR fold locally into distinct classes, small changes between structurally similar loops are unlikely to disrupt the local folding of the loop. Thus, the structure can also be used to guide incorporation of a minimal amount of parent sequence into a human CDR sequence or framework region while maintaining the correct local folding of the loop as well as the affinity and selectivity for the antigen. The modified loops and framework may properly orient themselves with respect to one another, forming a binding site whose structure is conserved from the parent antibody, once fully assembled into a final structure containing elements from as many as seven human and one non-human structure. Additionally, structural information can be utilized to guide selection of residues for conservation of the binding properties of the modified antibody as well as guiding the selection of residues that can be mutated to form a library of potential humanized constructs that may have improved properties over the initial construct.

SUMMARY OF THE INVENTION

The present invention relates to compositions and methods for modifying antibodies. In particular, the invention relates to the use of three-dimensional structure information to guide the process of modifying antibodies with amino acids from one or more templates or surrogates such that the antigen binding properties of the parent antibody are maintained and the immunogenicity potential of the antibody is reduced when administered as a therapeutic in humans.

This invention relates to a protein structure-based method of specifying an antibody that maintains the antigen binding specificity and affinity of the parent antibody, based on equating the atomic coordinates of antibody heavy and light chain variable region heterodimers. The parent antibody protein structure is used to guide the selection of one or more human or humanized antibody templates and the amino acid residues of the parent antibody that are to be modified to selectively refine the properties of the human template antibody. The method guides improvements in antibodies to reduce immunogenicity. The invention identifies the composition of a family of new human antibodies that are derived from a parent non-human antibody, or modifies a humanized version of an antibody. The invention applies to antibodies that would be a therapeutic for human diseases such as cancer, immune and inflammatory disorders, cardiovascular and metabolic diseases, neurological and neurodegenerative diseases, pain treatment, as well as treatment of drug abuse and disorders. The invention also pertains to the creation of an antibody therapeutic that would neutralize the effects of pathologic bacterial, protozoa, and/or viral-induced disease states in the human body.

One embodiment of the present invention is directed to the application of a series of computational steps used to define features of a new antibody. The method of developing a modified antibody to a form that is therapeutically acceptable in humans (hereafter referred to as 'humanization' or as 'humanizing a mouse antibody') comprises multiple computational steps. In essence, the method uses the three dimensional structure of the antibody heterodimer of variable region light and heavy chains. This involves the determination of the three dimensional structure of a parental antibody variable region segment comprising a light and heavy chain. The method of the present invention then provides a computational approach to superimpose the three dimensional structure of the variable region of the parent antibody onto a defined database of three dimensional structures of other antibodies. The method delineates the antibodies of the database, and a method to evaluate the database. The antibody database is evaluated in the present invention by means of inspection of the closest structural neighbors of the parent antibody.

The present invention also relates to the use of three-dimensional structure information to guide the process of modifying antibodies with amino acids from one or more templates or surrogates such that the antigen binding properties of the parent antibody are maintained and the immunogenicity potential is reduced when administered as a therapeutic in humans.

In one embodiment, the methods disclosed herein can be used to modify one or more monoclonal antibodies, such as murine monoclonal antibody ATN-615, that bind to, e.g., uPAR which has a therapeutic benefit against cancer, cardiovascular, and inflammatory diseases.

One embodiment is directed to monoclonal antibodies that bind to urokinase plasminogen activator receptor and comprise a light chain variable region having the amino acid sequence:

```
                                           (SEQ ID NO. 1)
DIQMTQSPSTLSASVGDRVTITCRASSSVSYIHWYQQKPGRAPKPLMYEA

SSRATGVPSRFSGSGSGTEYTLTISSLQSDDFATYYCQQWNYPFTFGQGT

KLEIK
``` and a heavy chain variable region comprising the amino acid sequence:

```
                                           (SEQ ID NO. 2)
EVQLVQSGAEVKKPGSSVKVSCKASGYTFTDYYIHWVRQAPGQGLEWIGW

IFHGSDNTEYNDAVKGRFSITADESTSTAYMELSSLRSEDTAVFYCARWG

PHWYFDAWGRGTLVTVS.
```

Another embodiment is directed to monoclonal antibody that binds to urokinase plasminogen activator receptor and comprises a light chain variable region having the amino acid sequence:

```
                                           (SEQ ID NO. 1)
DIQMTQSPSTLSASVGDRVTITCRASSSVSYIHWYQQKPGRAPKPLMYEA

SSRATGVPSRFSGSGSGTEYTLTISSLQSDDFATYYCQQWNYPFTFGQGT

KLEIK
``` and a heavy chain variable region comprising the amino acid sequence:

```
                                           (SEQ ID NO. 3)
EVQLVQSGAEVKKPGSSVKVSCKASGYTFTDYYIHWVRQAPGQGLEWIGW

IFHGSDNTEYNEKFKSKATITADESTSTAYMELSSLRSEDTAVFYCARWG

PHWYFDAWGRGTLVTVS.
```

Another embodiment is directed to monoclonal antibody that binds to urokinase plasminogen activator receptor and comprises a light chain variable region having the amino acid sequence:

(SEQ ID NO. 1)
DIQMTQSPSTLSASVGDRVTITCRASSSVSYIHWYQQKPGRAPKPLMYEA

SSRATGVPSRFSGSGSGTEYTLTISSLQSDDFATYYCQQWNYPFTFGQGT

KLEIK and a heavy chain variable region comprising the amino acid sequence:

(SEQ ID NO. 4)
EVQLVQSGAEVKKPGSSVKVSCKASGYRFSNFYIHWVRQAPGQGLEWIGW

IFHGSDNTEYNEKFKSKATITADESTSTAYMELSSLRSEDTAPFTFGQGT

KLEIK.

Another embodiment is directed to monoclonal antibody that binds to urokinase plasminogen activator receptor and comprises a light chain variable region having the amino acid sequence:

(SEQ ID NO. 5)
DIQMTQSPSTLSASVGDRVTITCRASSSVSYIHWYQQKPGRAPKPLMYET

SNLASGVPSRFSGSGSGTEYTLTISSLQSDDFATYYCQQWNYPFTFGQGT

KLEIK and a heavy chain variable region comprising the amino acid sequence:

(SEQ ID NO. 2)
EVQLVQSGAEVKKPGSSVKVSCKASGYTFTDYYIHWVRQAPGQGLEWIGW

IFHGSDNTEYNDAVKGRFSITADESTSTAYMELSSLRSEDTAPFTFGQGT

KLEIK.

Another embodiment is directed to monoclonal antibody that binds to urokinase plasminogen activator receptor and comprises a light chain variable region having the amino acid sequence:

(SEQ ID NO. 5)
DIQMTQSPSTLSASVGDRVTITCRASSSVSYIHWYQQKPGRAPKPLMYET

SNLASGVPSRFSGSGSGTEYTLTISSLQSDDFATYYCQQWNYPFTFGQGT

KLEIK and a heavy chain variable region comprising the amino acid sequence:

(SEQ ID NO. 3)
EVQLVQSGAEVKKPGSSVKVSCKASGYTFTDYYIHWVRQAPGQGLEWIGW

IFHGSDNTEYNEKFKSKATITADESTSTAYMELSSLRSEDTAVFYCARWG

PHWYFDAWGRGTLVTVS.

Another embodiment is directed to monoclonal antibody that binds to urokinase plasminogen activator receptor and comprises a light chain variable region having the amino acid sequence:

(SEQ ID NO. 5)
DIQMTQSPSTLSASVGDRVTITCRASSSVSYIHWYQQKPGRAPKPLMYET

SNLASGVPSRFSGSGSGTEYTLTISSLQSDDFATYYCQQWNYPFTFGQGT

KLEIK and a heavy chain variable region comprising the amino acid sequence:

(SEQ ID NO. 6)
EVQLVQSGAEVKKPGSSVKVSCKASGYTFTDYYIHWVRQAPGQGLEWIGW

IFHGSDNTEYNDAVKGFRSITADESTSTAYMELSSLRSEDTAVFYCARWG

PHWYFDAWGRGTLVTVS.

Another embodiment is directed to monoclonal antibody that binds to urokinase plasminogen activator receptor and comprises a light chain variable region having the amino acid sequence:

(SEQ ID NO. 5)
DIQMTQSPSTLSASVGDRVTITCRASSSVSYIHWYQQKPGRAPKPLMYET

SNLASGVPSRFSGSGSGTEYTLTISSLQSDDFATYYCQQWNYPFTFGQGT

KLEIK and a heavy chain variable region comprising the amino acid sequence:

(SEQ ID NO. 4)
EVQLVQSGAEVKKPGSSVKVSCKASGYRFSNFYIHWVRQAPGQGLEWIGW

IFHGSDNTEYNEKFKSKATITADESTSTAYMELSSLRSEDTAVFYCARWG

PHWYFDAWGRGTLVTVS.

Another embodiment is directed toward a monoclonal antibody that binds to urokinase plasminogen activator receptor and comprises a light chain variable region having the amino acid sequence:

(SEQ ID NO. 1)
DIQMTQSPSTLSASVGDRVTITCRASSSVSYIHWYQQKPGRAPKPLMYEA

SSRATGVPSRFSGSGSGTEYTLTISSLQSDDFATYYCQQWNYPFTFGQGT

KLEIK and a heavy chain variable region comprising the amino acid sequence:

(SEQ ID NO. 6)
EVQLVQSGAEVKKPGSSVKVSCKASGYRFSNFYIHWVRQAPGQGLEWIGW

IFHGSDNTEYNDAVKGRFSITADESTSTAYMELSSLRSEDTAVFYCARWG

PHWYFDAWGRGTLVTVS.

Yet other embodiments are directed toward anti-Lewis X monoclonal antibodies that are a modified antibody 1UZ8 using 1DEE as an acceptor comprising a light chain variable region having the amino acid sequence:

(SEQ ID NO: 7)
DIQMTQSPSSLSASVGDRVTITCRTSKSLLYSNGITYLYWYQQKPGKAPK

LLIYQMSNLASGVPSRFSSSGSGTDFTLTISSLQPEDFATYYCAQNLEVP

WTFGQGTKVEIK and a heavy chain variable region having the amino acid sequence:

(SEQ ID NO: 8)
QVQLVESGGGVVQPGKSLRLSCAASGFTFSGYWMSWVRQAPGKGLEWVAE

INPDSSTINYTPSLKDKFTISRDNSKNTLYLQMNSLRAEDTAVYYCAKET

GTRFDYWGQGTLVTVSS.

Other embodiments are directed to anti-Lewis X monoclonal antibodies that are a modified antibody 1UZ8 using 1NL0 as an acceptor comprising a light chain variable region having the amino acid sequence:

(SEQ ID NO: 9)
QSVLTQPPSVSAAPGQKVTISCSSSKSLLYSNGITYLYWYQQHPGKAPKL

MIYQMSNLASGVPDRFSSSGSGTDFTLDISGLQSEDEADYYCAQNLEVPW

LFGTGTKLTVLGQPK and a heavy chain variable region having the amino acid sequence:

(SEQ ID NO: 10)
GVQLVESGGGVVQPGRSLRLSCAASGFTFSTYWMSWVRQAPGKGLEWIGE

INPDSSTINYTPSLKDRFTISRDNSKNTLYLQMNSLRAEDTAVYYCARET

GTRFDYWGRGTMVTVSS.

Still other embodiments are directed to anti-Lewis X monoclonal antibodies that are a modified antibody 1UZ8 using 8FAB as an acceptor comprising a light chain variable region having the amino acid sequence:

(SEQ ID NO: 11)
ELTQPPSVSVSPGQTARITCSSSKSLLYSNGITYAYWYQQKPGRAPVMVI

YQMSNLASGIPQRFSSSTSGTTVTLTISGVQAEDEADYYCAQNLEVPWIF

GGGTKLTVLGQPK and a heavy chain variable region having the amino acid sequence:

(SEQ ID NO: 12)
AVKLVQAGGGVVQPGRSLRLSCIASGFTFSNYWMSWVRQAPGKGLEWIGE

INPDSSTINYTPSLKDRFTISRDNSKRTLYMQMNSLRTEDTAVYYCARET

GTRFDYWGQGVLVTVSS.

Another embodiment is directed toward a monoclonal antibody that binds to urokinase plasminogen activator receptor and comprises a light chain variable region having the amino acid sequence:

(SEQ ID NO: 13)
DIQMTQSPSTLSASVGDRVTITCRASQSVSYLAWYQQKPGRAPKPLMFEI

SSLKSGVPSRFSGSGSGTEYTLTISSLQSDDFATYYCQQWNYPFTFGQGT

KLEIK and a heavy chain variable region having the amino acid sequence:

(SEQ ID NO: 14)
EVQLVQSGAEVKKPGSSVKVSCKASGGTFTNFYIHWVRQAPGQGLEWMGW

IFHGSDNTEYNERFQGRVSITADESTSTAYMELSSLRSEDTAVFYCARWG

PHWYFDLWGRGTLVTVS.

Another embodiment is directed toward a monoclonal antibody that binds to urokinase plasminogen activator receptor and comprises a light chain variable region having the amino acid sequence:

(SEQ ID NO: 15)
IALTQSPGTLSLSPGERATLSCRASSSVSYMAWYQQKPGQAPRLLIFEIS

TRATGIPDRFSGSGSGTDYTLTISRLEPEDFAVYYCQQWNYPFTFGQGTR

LEIK and a heavy chain variable region having the amino acid sequence:

(SEQ ID NO: 16)
QVQLVQSGAEVKKPGASVKVSCKVSGYTLTELYIHWVRQAPGKGLEWVGW

IFHGSDNTEYNEKFQGSVTMTADTSTNIAYMELSSLRSDDTAVYYCARWG

PHWYFDVWGQGTMVTVSS.

Another embodiment is directed toward a monoclonal antibody that binds to urokinase plasminogen activator receptor and comprises a light chain variable region having the amino acid sequence:

(SEQ ID NO: 17)
SIELTQPPSVSVAPGKTARITCGASSSVSYMHWYQQKPGQAPVPVVYEDS

DRPSGIPERFSGSGSGNTYTLISRVEAGDEADYYCQQWNYPFVFGTGTKV

TVLGQPK and a heavy chain variable region having the amino acid sequence:

(SEQ ID NO: 18)
QVQLQQSGAEVKKPGSSVKVSCKASGGTFSSFYIHWVRQAPGQGLEWMGW

IFHGSDNTEYNQKFQGRVTITTDESTSTAYMELSSLRSEDTAVYYCARWG

PHWYFDVWGQGTTVTVSS.

Another embodiment is directed toward a monoclonal antibody that binds to urokinase plasminogen activator receptor and comprises a light chain variable region having the amino acid sequence:

(SEQ ID NO: 19)
IQMTQSPSSVSASVGDRVTITCRASQDVSYMAWYQQKPGKAPKPWIFEIS

TLQSGVPSRFSGSGSGTDYSLTINSLQPEDFATYYCQQWNYPFTFGGGTK

VEIK and a heavy chain variable region having the amino acid sequence:

(SEQ ID NO: 20)
EVQLVQSGAEVKKPGATVKISCKASGYTFSDFYIHWVRQAPGKGLEWMGW

IFHGSDNTEYNEKFRGRVTITADTSTDTGYLELSSLRSEDTAVYYCARWG

PHWYFDVWGQGTLVSVSS.

Yet other embodiments are directed toward anti-Lewis X monoclonal antibodies that are a modified antibody 1UZ8 that have a variable region light chain complementarity determining region 1 of amino acid sequence RTSKSXLYSNGI-TYLY (SEQ ID NO: 21), where X is L or I; RTSKSLXYS-NGITYLY (SEQ ID NO: 22), where X is L or S; RTSKSLLYSNGIXYLY (SEQ ID NO: 23), where X is T or S; or RTSKSLLYSNGITYXY (SEQ ID NO: 24), where X is L or A.

Yet other embodiments are directed toward anti-Lewis X monoclonal antibodies that are a modified antibody 1UZ8 that have a variable region light chain complementarity determining region 2 of amino acid sequence QMXNLAS (SEQ ID NO: 25), where X is S or T; QMSXLAS (SEQ ID NO: 26), where X is N, S, K, or Q; or QMSNXAS (SEQ ID NO: 27), where X is L or R.

Yet other embodiments are directed toward anti-Lewis X monoclonal antibodies that are a modified antibody 1UZ8 that have a variable region light chain complementarity determining region 3 of amino acid sequence AXNLEVPW (SEQ ID NO: 28), where X is Q or A.

Yet other embodiments are directed toward anti-Lewis X monoclonal antibodies that are a modified antibody 1UZ8 that have a variable region heavy chain complementarity determining region 2 of amino acid sequence IXPDSSTINY-TPSLKDK (SEQ ID NO: 29), where X is N or S; INPDX-STINYTPSLKDK (SEQ ID NO: 30), where X is S or E; INPDSSXINYTPSLKDK (SEQ ID NO: 31), where X is T, N, K, or R; INPDSSTXNYTPSLKDK (SEQ ID NO: 32), where X is I, K or T; INPDSSTINYTPSXKDK (SEQ ID NO: 33), where X is L or V; or INPDSSTINYTPSLKDX (SEQ ID NO: 34), where X is K or R.

Yet other embodiments are directed toward anti-urokinase plasminogen activator receptor antibodies that are a modified antibody 2FD6 that have a variable region light chain complementarity determining region 2 of amino acid sequence XEISSLKS (SEQ ID NO: 35), where X is F or Y or FEXSS-LKS (SEQ ID NO: 36), where X is I, A, or D.

Yet other embodiments are directed toward anti-urokinase plasminogen activator receptor antibodies that are a modified antibody 2FD6 that have a variable region heavy chain complementarity determining region 1 of amino acid sequence FXNFYIH (SEQ ID NO: 37), where X is T or S; FTXFYIH (SEQ ID NO: 38), where X is N or D; FTNXYIH (SEQ ID NO: 39), where X is F or L; or FTNFYXH (SEQ ID NO: 40), where X is I, M, or V.

Yet other embodiments are directed toward anti-urokinase plasminogen activator receptor antibodies that are a modified antibody 2FD6 that have a variable region heavy chain complementarity determining region 2 of amino acid sequence WXFHGSDNTEYNE (SEQ ID NO: 41), where X is I or F or WIFHGSDN-TEYNX (SEQ ID NO: 42), where X is E or Q.

Yet other embodiments are directed toward anti-urokinase plasminogen activator receptor antibodies that are a modified antibody 2FD6 that have a variable region heavy chain complementarity determining region 3 of amino acid sequence RWGPHWXFD (SEQ ID NO: 43), where X is Y or A or RWGPHWYXD (SEQ ID NO: 44), where X is F or K.

The antibodies described above comprising CDRs with amino acid substitutions can be combined to make a plurality of constructs with activity similar to or identical to the parent antibody, but with less immunogenicity since the substitutions replace parent amino acids with human amino acids.

For a better understanding of the present invention, together with other and further objects thereof, reference is made to the accompanying drawings and detailed description.

DESCRIPTION OF THE DRAWINGS

FIG. 3 depicts the structure based amino acid sequence alignment. A structural overlay of the parent and acceptor antibodies is conducted by the method, creating a residue-by-residue alignment for structurally equivalent residues along both heavy and light chains. Shown are the top scoring scaffolds and the parent structure 1UZ8. Highlighted by underline are sequences used for grafting. Residues that were changed as suggested by the method are highlighted in italics. Residues defined as SDR are highlighted in bold and italics (SEQ ID NOS: 45-52);

FIG. 5 depicts the generated combinatorial library of sequences in the CDR regions. Indicated residues were compared to the structural superpositions summarized in FIG. 3. Structurally similar residues are listed below with the parent antibody structure labeled as "Parent". The modification was modeled and subjected to energy minimization, the final energy for the modified residue is tabulated;

FIG. 9. Generation of the combinatorial library of sequences in the CDR regions. Indicated residues were compared to the structural superpositions summarized in FIG. 7. Structurally similar residues are listed below with the parent antibody structure labeled as "Parent". The modification was modeled and subjected to energy minimization, the final energy for the modified residue is tabulated;

FIG. 10 is a flow chart of the EPU Method of the Invention;

FIG. 11 is an outline of the EPU Method of the Invention;

FIG. 12 is a structure based sequence alignment of top scoring CDR from the alignment of the parent structure to the corresponding human structure database. The defined SDR for the loop are highlighted in bold and italics. Single mutations and grafting of segments of parental structure of the human structure to introduce SDR into the human structures are underlined. The conservation of residues is shown on the line below the alignment, where an asterisk represents a conserved residue and a point represents high similarity. The alignments shown are for CDRL1 (A), CDRL2 (B), CDRH1 (C), CDRH2 (D), and CDRH3 (E). There was no close structural analog in the database to the CDRL3 loop of the parent structure. Also shown is the rmsd score and the percentage of backbone atoms aligned from the output of IMF in DeepView. In (F), the results of the alignment of the framework regions is shown in terms of rmsd and percentage of alpha carbons aligned from the IMF calculation;

FIG. 13 is a ribbon diagram of two final, minimized models colored by the source of the structure. The structure is made up from residues from the parent (red) and human structures #29 (blue), #1 (yellow), #7 (orange), #2 (green), #14 (cyan), #18 (black), #16 (dark green) and #20 (gray). Despite the variation in the source of the structures used, the binding sites are very similar (SEQ ID NOS: 53-77);

FIG. 14 is an overlay of the parent structure (black) and the final, minimized structures (dark and light gray) from FIG. 13. The side chains displayed are those of the SDR. The figure shows excellent conservation of the antigen binding site in the modified construct; and FIG. 15 are sequences of constructs created by the EPU method highlighted according to the source of the sequence from the parent (bold and italics) and human structures #29 (normal text), #1 (double underline), #7 (underline), #2 (dotted underline), #14 (dashed underline), #18 (dotted and dashed underline), #16 (serrated underline) and #20 (double wavy underline) (SEQ ID NOS: 78-93).

DETAILED DESCRIPTION OF THE INVENTION

The present invention relates the use of three-dimensional structure information to guide the process of modifying antibodies with amino acids from one or more templates or surrogates such that the antigen binding properties of the parent antibody are maintained and the immunogenicity potential is reduced when administered as a therapeutic in humans.

Methods are disclosed herein for the creation of a new antibody. The methods involve the definition of an antibody, in particular the determination of an antibody variable region amino acid sequence. The invention includes a group of computational steps to convert an antibody, termed the "parent antibody", to a new antibody composition comprising a delineated amino acid composition of each antibody chain. The new antibody can comprise a single second antibody, or a structurally related family of second antibodies. The method is a means to utilize protein structural information in the form of a listing of the atomic coordinates of the parent antibody as a tool to evolve features of newly formed antibodies of the invention. The invention creates a cluster of highly related antibodies that vary based on the three-dimensional structural features of the antibody. The variation in members of the antibody cluster comprise alterations in the antibody folding properties concentrated in the variable domain of the antibody. The variation has utility in providing antibodies of the invention that are capable of binding the target hapten with different levels of binding affinity. The antibody cluster variation has the further utility of revealing protein epitopes that are either contiguous or non-contiguous. The computational steps of the invention provide a means to identify and prioritize antibody variation relevant to the two key features: antigen binding specificity and affinity, and the preponderance of region-specific epitopes of the antibody to create immunogenic properties.

1. Overview of the Invention by Steps

The invention is the application of a series of computational steps to define the features of a new antibody. The invention comprises two distinct methods, each of which will be outlined. Each method of developing a modified antibody to a form that is therapeutically acceptable in humans (hereafter referred to as 'humanization' or as 'humanizing a mouse antibody' comprises four main computational steps. In essence, the methods use the three dimensional structure of the antibody heterodimer of variable region light and heavy chains. The first step in both methods involves the determination of the three dimensional structure of the parental antibody variable region segment consisting of a light and heavy chain. In particular, the methods utilize the three-dimensional structure of the parent antibody variable domain consisting of the variable region light and heavy chain components. These methods will be obvious in their execution to one skilled in the art. The parent antibody protein structure may be acquired by experimental determination from the full antibody, Fv, Fab $(Fab)_2$, and other forms, or may be as issued from a database, such as the Protein Data Base.

The invention then provides computational approaches to superimpose the three dimensional structure of the variable region of the parent antibody onto a defined database of three dimensional structures of other antibodies. The Structure Grafting method is outlined in Sections 2.-6. The EPU method is outlined in Sections 7.-11. Sections 12 and 13 describe the features of the models created and their potential to reduce immunogenicity. A description of the antibodies that may be generated by the methods follows in Section 14 and 15. A description of the technologies to examine these antibodies follows in Sections 16 and 17. Therapeutic utilities of these antibodies follow in Section 18.

2. Determination of Best-Fitting Human Antibody Structures ('Acceptor Structures')

In essence, the methodological step of the Structure Grafting method of the invention uses, the three dimensional representation of the Fv mouse antibody structure as elucidated from its atomic coordinates, and then superposes these coordinates onto a database of the human antibody Fv region structures. The invention delineates the antibodies of the database, and a method to evaluate the database. The antibody database is evaluated in the invention by means of inspection of the closest structural neighbors of the parent antibody. The evaluation includes a means for ranking and prioritization of the structurally related proteins. The method utilizes a numeric convention for the comparison of protein structures that is in practice for one skilled in the art. The invention pertains to the use of computational tools, such as the root mean square deviation (rmsd) of structurally equivalent atoms. The invention specifies the atoms for the comparison in the database generation and in the execution of the invention. Such an approach is exemplified by the usage of a computational method, the Iterative Magic Fit command (IMF), as implemented in DeepView/Swiss-PDBViewer, as will be apparent according to one skilled in the art.

Figure 1:
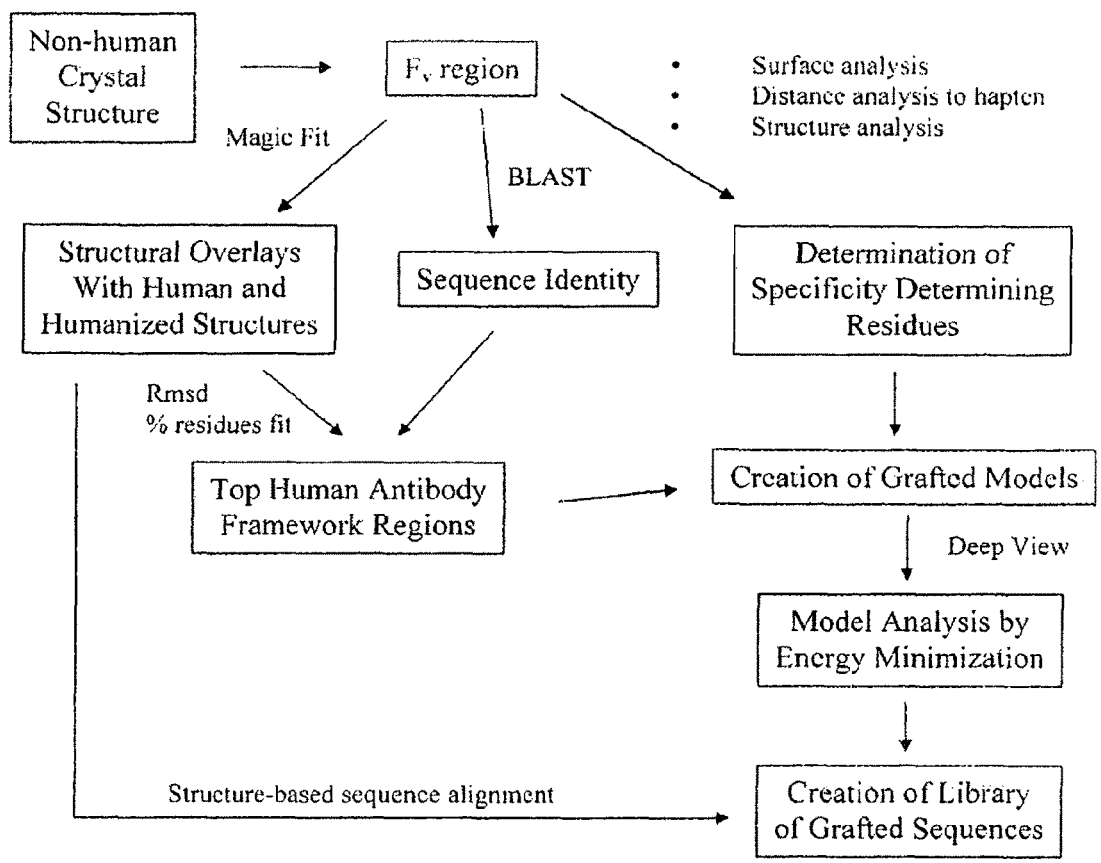
FIG. 1 is a flow chart of an embodiment of the present invention.

A brief description of the IMF approach is delineated as follows. IMF aligns two structures by first aligning the amino acid sequences of the proteins to be superposed, and then making an initial fit by least squares superposition of identical residues from the two protein molecules. This initial fit is then refined by iterative cycles where the overall root mean square deviation (rmsd) of the fit is minimized while keeping the number of residues in the fit maximized. As will be obvious to one skilled in the art, rmsd is a scoring term that describes increasing similarity between two protein structures represented by their atomic coordinates, and for segments of these overall structures. Unlike other available methods for aligning multiple structures (VAST, DALI, CE), the IMF used here allows the determination of the fit to both the heavy and light chains simultaneously, thus incorporating information from the protein quaternary structure into the analysis. One skilled in the art will appreciate that protein quaternary structure is an important feature of protein function. Since the antibody-binding site is comprised of residues from both protein chains, the quaternary structure is important to maintain the integrity of the binding site from the mouse antibody after grafting onto the human structure.

According to the method, the rmsd fit of each available member of the human antibody structure database to the mouse antibody structure is computationally processed and assembled. The results of the iterative computational processing of each overlay generate a numeric value for each entry that populates a tabular database. Subsequently, the best fit human structures are passed on to further analysis. Since the rmsd is a global term, this best fit human structure will most closely resemble the parent structure in the CDR regions, as well as the framework regions. Additionally, the best fit structure will display a spatial relationship between the heavy and light chains that is closest to the parent structure. The rmsd values fall into three categories: Highly similar structures with rmsd values<0.9 Å calculated using >95% of all alpha carbons, fairly similar structures with rmsd values<1.1 Å calculated using >90% of all alpha carbons, and non-similar structures with rmsd values>1.1 Å. Typically highly related human proteins having <0.9 Å rmsd calculated using >95% of all alpha carbons will be achieved. Also, less highly related human proteins having <1.2 Å rmsd calculated using >95% of all alpha carbons will be achieved. Also, even less related human proteins having <1.5 Å rmsd calculated using >95% of all alpha carbons will be achieved. In addition, even less related human proteins having <2 Å rmsd calculated using >95% of all alpha carbons will be achieved. Human antibody proteins are assembled in the database with even less similarity as is indicated by <2 Å, <3 Å, <4 Å, <5 Å rmsd calculated using of >95% of the alpha carbons, as is dictated by the method. Similarly human antibody proteins will be determined by the method have <0.9 Å rmsd calculated using of >90% of all alpha carbons and even less highly related proteins having <1.2 Å rmsd calculated using of >90% of all alpha carbons, and so on.

According to the method as implemented, the term 'acceptor structure' here refers to one or more of the most favorable human antibodies of the invention, qualified by the ranking parameters disclosed. Typically, there will be a gap in the rmsd values of the best fit cluster of structures and the structures that are not as structurally equivalent. This gap can vary from 0.04-0.2 Å and represents a cutoff point between structures that are considered for grafting and those that are not considered. According to the method, the acceptor structures of best fit clustering defined by the lower rmsd values will be preferred. Whereas the clustering of these acceptor structures of greatest similarity is commonly utilized, the method also allows for the computational exercise to be completed with acceptor structures of reduced fit, and having a greater disparity from the 'best fit' structures.

3. Determination of Amino Acid Similarity of Best-Fit Human Antibody Structures

The next step of the method comprises determining which of the best fitting human antibody structures (acceptor structures) are the closest in amino acid sequence similarity to the parent antibody, based on the combined inputs from both heavy and light chain variable region gene segments. A computational method, such as the BLAST program, is used to determine the amino acid sequence identity and similarity of the heavy and light chains, and each of these determinations is included as an Amino Acid Sequence Alignment database. Generally, the structures having better than 85% identity and 85% similarity in both chains will be achieved. Structure alignments having lower degrees of identity (80, %75%, 70%, 65%, 60%, 55%, 50%, 45%, 40%, 35%) and similarity (80%, 75%, 70%, 65%, 60%, 55%, 50%) will be determined by the method. According to the method, the identification of human antibodies possessing the combined greater percentage of amino acid identity and similarity will be ranked higher relative to human antibodies possessing combined lower percentage of amino acid identity and similarity. The human structures that are the best fit in both structure and sequence are then chosen as acceptors for grafting of CDR sequences from the parent structure.

Also according to the method, the plurality of tester protein sequences includes preferably antibody sequences, and more preferably human antibody sequences. Tester protein sequences may be from the human germline antibody sequences (such as is defined in V-database and an IGMT database; Ruis et al, 2000, Nuc. Acids Research Vol. 28, No, 1. pp 219-221) and these sequence databases especially contain the framework regions. Also according to any of the above methods, the plurality of tester protein sequences is retrieved from Genbank of the NIH or Swiss-Prot database or the Kabat database for CDRs of antibodies.

According to the method, antibody structure similarity and antibody sequence similarity are not matched. In other words, graphical representations of the two databases from the steps one and two are instructive. The outcome for computational processing of one example relating rmsd to sequence similarity is illustrated in FIG. 3. The method teaches that there is not an associated linear relationship between protein structure and sequence similarity for the highly related proteins of the antibody family. Instead, the method teaches that the determination of the three dimensional representation of the antibody and its quaternary structure, is the important parameter in dictating the most related two proteins, or the most similar in related groups of proteins. One skilled in the art will appreciate that the antigen binding pocket of an antibody is composed of the combined folding and three dimensional representation of both light and heavy variable region chains.

The best fit protein structures, based on the criteria of rmsd and sequence identity, can then be passed on to subsequent steps for grafting of parental structural information for the generation of new antibodies. Typically, between one and ten human structures are discovered with rmsd values within 0.1 Å of the top scoring human structure and sequence identity values of greater than 45%. These structures represent a library of antibody heavy and light chain framework residues onto which the parental antibody structural determinants of specificity can be grafted, as explained in the next section. It will be obvious that each structure in this library can be independently converted and modified in tandem by the latter steps of the method as described below.

4. Specificity Determining Residues (SDR)

The invention specifies the computational evaluation of the specificity determining residues (SDR) of the antibody Specificity determining residues are determinants essential for mediating binding interactions with haptens, small molecules, protein antigens and any other molecular structure identifiable as the epitope recognized by the antibody molecule. The SDR are not limited to the determinants of binding of a hapten but also include determinants of the catalytic activity of the antibody necessary for the chemical reaction of the hapten upon binding to the antibody. These functions include general acid/base catalysis, conformational catalysis, electrostatic catalysis, metal ion catalysis, and covalent catalysis. These SDR are typically in the CDR regions of the antibody, but are not limited to these regions and can include residues from the framework regions as dictated by the structure. Conversely, not all CDRs will contain SDRs.

According to the method, the third step comprises identification of residues in the parent structure that are essential for antigen binding, also called specificity determining residues (SDR). These residues are identified according to two methods, dependent upon whether or not the parent structure was crystallized with a hapten or not. In the case of where the hapten cocrystal structure is determined, the SDR are identified by proximity to the hapten. All residues within 5 Å of the hapten in the parent structure are identified. This distance is selected since most important molecular interactions involved in binding an antigen epitope (van der Waal's, hydrogen bonding, salt bridges, electrostatic interactions) are relevant at this distance or shorter distance. These selected residues are placed into the list of SDR. In the case where there is no cocrystal structure available, the SDR are determined by inspection of the binding site and determination of each residue's contribution to the binding site surface. First, a molecular surface is calculated using a program such as Deep View. Other programs can be used to create such a surface (GRASP, MSMS, QUANTA). The contribution to the surface of the Chothia defined CDR residues is then designated by coloration of the surface. Ale antigen binding site is delineated visually. This site resides in the cleft between the heavy and light chains created by the CDR residues. The surface is then colored according, to the contribution of each individual residue to the surface in each CDR. Residues that are visually determined to contribute to the antigen binding surface are added to the SDR list. These binding sites can also be determined using computational methods with programs such as VOIDOO and CASTp, however, these programs are better at determination of fully closed cavities in proteins and are not as robust in identification of binding site clefts, thus a visual inspection method may be superior given current levels of technology.

The list of SDR is then expanded to include other residues from the Chothia defined CDR residues. Each residue in the CDR regions is inspected in the structure for interactions or features that may be required for proper folding of the loop into the desired conformation for antigen binding. These interactions and features fall into many categories. The backbone atoms are inspected for each residue. Residues with cis peptide bonds or phi and psi torsion angles that are indicative of a turn structure or other rare conformation are added to the list of SDR, since these backbone conformations need to be retained in the modified antibody. Due to their restricted backbone torsion angles, proline residues in CDR loops are added to the SDR list to conserve the backbone conformation at these positions, The side chains are then inspected for interactions that may be important. These interactions include salt bridges, hydrogen bonds, and other electrostatic interactions. These interactions may occur with other residues in the same loop, residues in other loops, residues in the framework, or residues in the other protein chain. Maintenance of these interactions in the modified antibody will be essential for desired antigen binding, in particular, interactions with SDR determined from the first step. Small side chain amino acids such as alanine or glycine are inspected for crowding in the vicinity of the residue. Some structures will not tolerate larger side chains at these positions, and thus the smaller side chain must be retained in the modified construct. Lastly, any information from biochemical or mutagenesis experiments from the literature or in house data can be incorporated at this step to include residues that have been shown experimentally to be critical for antibody binding and efficacy. These residues are also added to the list of SDR prior to the grafting step.

5. Energy Minimization of the Initial Model

According to the method, the fourth step is a computational process whereby an initial model of the modified antibody is created by replacing the atomic coordinates of the human CDRs in the acceptor structures with the atomic coordinates of the parent antibody CDRs. First, the parent CDR amino acid residues are located as characterized by the standard definitions according to Clothia's canonical definitions, and based on amino acid sequence determinations for each of the evaluated heavy chain and light chain protein segments. According to the method, the step of identifying the amino sequences in the CDRs is carried out by using Kabat criteria or Chothia criteria. One who is skilled in the art will be knowledgeable of the 3 CDR from light chain variable region gene segments and of the 3 CDR from heavy chain variable region gene segments. The 12 residues at the boundaries of each CDR are defined as initial graft junctions. The structures of the parent and acceptor structure are then superposed. Each residue defined as a graft junction is then inspected and a new graft junction defined according to the following method. If the superposed structures are divergent at the residue in question (rmsd for residue backbone atoms greater than 0.5 Å), the junction is moved one residue away from the center of the loop. If the superposed structures are well overlaid (rmsd for residue backbone atoms less than or equal to 0.5 Å), the residue is checked against the list of SDR. If the residue is a SDR, the junction is defined as that residue and no further inspection steps are taken for this junction. If the residue is not a SDR, the junction is then redefined one residue toward the center of the loop. These steps are applied in an iterative fashion for each junction residue until all residues are defined such that the coordinates to be grafted both superposed well with the parent and acceptor structures and contain all SDR on the list. The coordinates defined by the junction residues in the acceptor structure are then replaced with corresponding coordinates from the parent structure.

The following step in the computational method is energy minimization of the initial model, as a mechanism to define similarity between the parental and modified human antibody(s) as described in the previous steps. Energy calculations may be achieved by a variety of methods using programs such as CHARMm, CNS, CNX, and DeepView/Swiss-PDBViewer. An energy calculation using the GROMOS96 force field is first performed in DeepView/Swiss-PDBViewer to determine residues making good or poor steric and good or poor electronic contacts. The evaluation of appropriate contacts will be obvious to one skilled in the art. Residue-by-residue inspection is provided in the execution of the method. An outcome consisting of poor energy values will precipitate change to the residue such that the calculated energy value for the residue will be negative (favorable). These residues are inspected and changed if making particularly poor contacts. These changes to the model can include rotation of side chains to favored rotamers without bad contacts or replacement of one or many residues in areas contacting the grafted CDR sequences (including neighboring loops and Vernier residues). At this stage, potential problems in the folding of the modified antibody due to differences in either the backbone or side chain structures of the acceptor structure incompatible with the structures of the parent antibody can be addressed. Typically, this requires replacement of key residues in the acceptor framework regions with the corresponding residues from the parent antibody. The choice of structures to change is also guided by consultation of the alignment of multiple structures generated in the first step. The structure is then subjected to 200 cycles of conjugate gradient minimization which will regularize the peptide bonds in the junction sites and also alleviate any small energetic violations in the model. The maintenance of the integrity of antigen binding site structure is determined by calculation of the rmsd of all atoms in the grafted structures before and after minimization. These values should be small (less than 0.3 Å) in the case of a successful grafting.

This procedure of grafting and minimization of the initial model is iteratively performed for all top scoring human structures from the first step. This results in the generation of a small library, between one and ten antibodies, of heavy and light chain sequences that can be constructed and tested for desired properties. Each model may be analyzed and ranked at this point in terms of the number of residues grafted, bad contacts found in the initial model, number of mutations to the framework or grafted regions needed to alleviate poor contacts in the initial model and rmsd of the grafted regions calculated using all non-hydrogen atoms before and after minimization. The best models will have a minimum value for all of these criteria, showing a minimal amount of non-human sequence that fits well into the new framework with few changes and potential folding problems and the smallest perturbation of the parental structure upon minimization. These best models can then be prioritized in the list relative to other models with less confidence.

6. Elimination of Parental Antibody Residues by Iterative Energy Minimization and Substitution The final step comprises a further reduction in the amount of parental amino acids in the grafted regions of the structure. The best model from step four is superposed into the structures of the parent antibody as well as the top scoring human and humanized antibodies from the first step. Residues in the graft regions that are not on the SDR list are then considered one by one for potential modifications. For each residue, the superposition is consulted to find residues in the CDR loops of human and humanized structures that overlay well (rmsd<1.0 Å calculated using backbone atoms) with the parent residue. These residues are tabulated in the structure based sequence alignment generated in the first step. Each potential substitution is then tested for goodness of fit in the model. First, the parent residue is changed to the human or humanized amino acid side chain by substitution of the parent side chain coordinates with coordinates from a rotamer library of low energy conformations. Some residues will not have a rotamer in the library that does not have severe steric clashes with the model. These potential substitutions are removed from consideration at this point. If the parent structure contains a hapten, the potential substitution is additionally analyzed for its potential contribution to antigen binding. Substitutions making poor contacts to the antigen are removed from consideration. The modified model is then subjected to 200 cycles of conjugate gradient minimization. The calculated energy of the modified residue is tabulated and then compared to the calculated energy of the parent residue. Successful substitutions will have energy values less than zero and preferably close to the parent residue. Some substitutions will score better than the parent. These are added to the list of potential substitutions for the parent residue under consideration. Substitutions that score positive energy are not added to the list of potential substitutions. In this manner, each potential residue is considered in turn and a list comprising a library of mutations to the grafted regions is generated.

7. The EPU Method Overview

The parent antibody structure is first divided into seven parts, the six CDR loops and the framework region comprising both heavy and light chains. The invention then provides a computational approach to superpose the three dimensional structures of these regions of the parent antibody onto a defined database of corresponding three dimensional CDR loop and framework structures of other antibodies. The invention delineates the antibodies of the database, and a method to evaluate the database. The antibody database is evaluated in the invention by means of inspection of the closest structural neighbors of the parent antibody. The evaluation includes a means for ranking and prioritization of the structurally related proteins. The method utilizes a numeric convention for the comparison of protein structures that is in practice for one skilled in the art. The invention pertains to the use of computational tools, such as the root mean square deviation (rmsd) of structurally equivalent atoms. The invention specifies the atoms for the comparison in the database generation and in the execution of the invention.

8. Specificity Determining Residues (SDR)

The invention specifies the computational evaluation of the specificity determining residues (SDR) of the antibody. Specificity determining residues are determinants essential for mediating binding interactions with haptens, small molecules, protein antigens, and any other molecular structure identifiable as the epitope recognized by the antibody molecule. The SDR are not limited to the determinants of binding of a hapten but also include determinants of the catalytic activity of the antibody necessary for the chemical reaction of the hapten upon binding to the antibody. These functions include general acid/base catalysis, conformational catalysis, electrostatic catalysis, metal ion catalysis, and covalent catalysis. These SDR are typically in the CDR regions or the antibody, but are not limited to these regions and can include residues from the framework regions as dictated by the structure. Conversely, not all CDRs will contain SDRs.

According to the method, the first step comprises identification of residues in the parent structure that are essential for antigen binding, also called specificity determining residues (SDR). These residues are identified according to two methods, dependent upon the availability of a co-crystal structure of the parent antibody with its hapten. In the case of where the hapten co-crystal structure is determined, the SDR are identified by proximity to the hapten. All residues within 5 Å of the hapten in the parent structure are identified. This distance is selected since most important molecular interactions involved in binding an antigen epitope (van der Waal's, hydrogen bonding, salt bridges, electrostatic interactions) are relevant at this distance or shorter distance. Residues will interact with the hapten through their side chain atoms as well as their main chain atoms. Residues interacting with the hapten exclusively through backbone contacts are excluded from the list of SDR. These selected residues are placed into the list of SDR.

In the case where there is no co-crystal structure available, the SDR are determined by inspection of the binding site and determination of each residue's contribution to the binding site surface. First, a molecular surface is calculated using a program such as Deep View. Other programs can be used to create such a surface (GRASP, MSMS, QUANTA). The contribution to the surface of the Chothia defined CDR residues is then designated by, e.g., coloration of the surface. The antigen binding site is delineated (visually in the case that e.g., color is employed). This site resides in the cleft between the heavy and light chains created by the CDR residues. The surface is then indicated using, e.g., color, according to the contribution of each individual residue to the surface in each CDR. Residues that are visually determined to contribute to the antigen binding surface are added to the SDR list. Additionally, residues not in CDR loops that by visual inspection are contributing to the antigen binding site surface are added to the SDR list. These binding sites can also be determined using computational methods with programs such as VOIDOO and CASTp, however, these programs are better at determination of fully closed cavities in proteins and are not as robust in identification of binding site clefts, thus a visual inspection method may be superior given current levels of technology.

The list of SDR is then expanded to include other residues from the Chothia defined CDR residues and framework residues. Each residue in the CDR regions is inspected in the structure for interactions or features that may be required for proper folding of the loop into the desired conformation for antigen binding. These interactions and features fall into many categories. The side chains are inspected for interactions that may be important. These interactions include salt bridges, hydrogen bonds, and other electrostatic interactions. These interactions may occur with other residues in the same loop, residues in other loops, residues in the framework, or residues in the other protein chain. Maintenance of these interactions in the modified antibody will be essential for desired antigen binding, in particular, interactions with SDR determined from the first step. Thus, both amino acid partners involved in such interactions will be included in the SDR list. Small side chain amino acids such as alanine or glycine are inspected for crowding in the vicinity of the residue. Some structures will not tolerate larger side chains at these positions, and thus the smaller side chain must be retained in the modified construct. Additional interactions include van der Waal's interactions that appear in the structure to be critical for positioning of a particular protein side chain or loop. Lastly, any information from biochemical or mutagenesis experiments from the literature or in house data can be incorporated at this step to include residues that have been shown experimentally to be critical for antibody binding and efficacy. These residues are also added to the list of SDR prior to the grafting step.

9. Determination of Best-Fitting Human Antibody Structures ('Acceptor Structures')

In essence, the methodological step of the invention uses, the three dimensional representation of the Fv mouse antibody structure as elucidated from its atomic coordinates. These coordinates are then separated into the six CDR loops and the framework region using a text editor. These seven separate regions are then superposed onto the corresponding database of the human antibody structures that have been similarly separated into their component units. Such an approach is exemplified by the usage of a computational method, the Iterative Magic Fit command (IMF), as implemented in DeepView/Swiss-PDBViewer, as will be apparent according to one skilled in the art.

A brief description of the IMF approach is delineated as follows. IMF aligns two structures by first aligning the amino acid sequences of the proteins to be superposed, and then making an initial fit by least squares superposition of identical residues from the two protein molecules. This initial fit is then refined by iterative cycles where the overall root mean square deviation (rmsd) of the fit is minimized while keeping the number of residues in the fit maximized. As will be obvious to one skilled in the art, rmsd is a scoring term that describes increasing similarity between two protein structures represented by their atomic coordinates, and for segments of these overall structures. Unlike other available methods for aligning multiple structures (VAST, DALI, CE), the IMF used here allows the determination of the fit to both the heavy and light chains simultaneously, thus incorporating information from the protein quaternary structure into the analysis. One skilled in the art will appreciate that protein quaternary structure is an important feature of protein function. Since the antibody-binding site is comprised of residues from both protein chains, the quaternary structure is important to maintain the integrity of the binding site from the mouse antibody after grafting onto the human structure.

According to the method, the rmsd fit of each available member of the human antibody structure database to the mouse antibody structure is computationally processed and assembled. The results of the iterative computational processing of each overlay generate a numeric value for each entry that populates a tabular database. Subsequently, the best fit human structures are passed on to further analysis. The best fit structure for the framework regions will display a spatial relationship between the heavy and light chains that is closest to the parent structure. For the CDR loops, the best fit structure will display a backbone structural class most similar to the parent structure. The rmsd values for the framework fall into three categories: Highly similar structures with rmsd values around <0.9 Å calculated using about >95% of all alpha carbons, fairly similar structures with rmsd values around <1.1 Å calculated using about >90% of all alpha carbons, and non-similar structures with rmsd values around >1.1 Å. Typically highly related human proteins having around <0.9 Å rmsd calculated using about >95% of all alpha carbons will be achieved. Also, less highly related human proteins having around <1.2 Å rmsd calculated using about >95% of all alpha carbons will be achieved. Also, even less related human proteins having around <1.5 Å rmsd calculated using about >95% of all alpha carbons will be achieved. In addition, even less related human proteins having around <2 Å rmsd calculated using about >95% of all alpha carbons will be achieved. Human antibody proteins are assembled in the database with even less similarity as is indicated by around <2 Å, <3 Å, <4 Å, <5 Å rmsd calculated using about >95% of the alpha carbons, as is dictated by the method. Similarly human antibody proteins will be determined by the method have around <0.9 Å rmsd calculated using about >90% of all alpha carbons, and even less highly related proteins having around <1.2 Å rmsd calculated using about >90% of all alpha carbons, and so on. For the CDR loops, there will be several categories the values will fall into: Highly related loops with rmsd values around <0.3 Å calculated using about >90% of backbone atoms, very related loops with rmsd values around <0.6 Å calculated using about >80% of backbone atoms, somewhat related loops with rmsd values around <1.0 Å calculated using about >60% of backbone atoms, and unrelated loops with rmsd values around >1.0 Å calculated using about <50% of backbone atoms.

According to the method as implemented, the term "acceptor structure" herein refers to one or more of the most favorable human antibodies of the invention, qualified by the ranking parameters disclosed. Typically, there will be a gap in the rmsd values of the best fit cluster of structures and the structures that are not as structurally equivalent. This gap can vary from about 0.04 to about 0.2 Å and represents a cutoff point between structures that are considered for grafting and those that are not considered. According to the method, the acceptor structures of best fit clustering defined by the lower rmsd values will be suitable. Whereas, the clustering of these acceptor structures of greatest similarity is commonly utilized, the method also allows for the computational exercise to be completed with acceptor structures of reduced fit, and having a greater disparity from the 'best fit' structures.

10. Grafting of Parental SDR into Selected Human Structures

To select the final structure for assembly of the complete modified antibody, the CDR structures from the database search that are within 0.15 Å rmsd of the top scoring solution with the highest number of backbone atoms aligned for the group are considered for selection. In some cases, the top scoring solution has a far lower rmsd score than the second best scoring loop, in these cases, only the top scoring loop is considered. The selection is preformed by superposing the parent loop with the human loops with IMF in Deep View. A structure based sequence alignment results from this analysis. The loops are then compared in sequence with the parent loop to determine the number of amino acids in the loop will need to be changed such that all the SDR for that loop are represented in the final structure. The number of changes that need to be introduced can vary from zero (if the database loop is identical to the parent) to the entire loop (in cases where a suitable structural analog to the parent loop cannot be found in the database). The changes that are introduced are either point mutations, where a single residue side chain in the database loop is altered to match the side chain of the parent in regions where the loop structures overlay well (rmsd<0.4), or crafts, where one or more residues from the parent structure are introduced. Loops that both fit well and have a minimum number of residues that need to be introduced are selected for the final assembly. There may be more that one suitable choice from the database at this point for a particular loop. These multiple choices can be incorporated into a small library of potential antibodies for testing. A last step to the process is to inspect the SDR that are conserved in the new loop to insure that the conformation of the side chain of these residues is conserved as well. If the side chain is different between the parent and database structure, the database structure side chain is altered through rotation of torsional bonds to match the structure of the parent. Since the loops both belong to the same folding class of CDR and the number of changes to the database loop is kept to a minimum, the structural integrity of the loop is likely to be maintained in the new construct. At the end of this analysis, at least six CDR loops are created that contain the parental SDR in the context of a human database loop that is known to fold in a similar way to the parent.

Selection of the frameworks for grafting is preformed differently than for the loops. The framework regions are all ranked by rmsd. Structures that have less than about 90% of the alpha carbons overlaid in the fitting are eliminated. The remaining structures are then analyzed for suitability to accept the grafted CDR structures by rmsd analysis of the backbone atoms of the residues at the Chothia-defined ends of the CDR loops. These residues should overlay well if the framework is suitable for accepting the CDR loops generated in the previous step. The parent and database structures are superposed, and the rmsd of the N-terminal and C-terminal residues of each CDR loop of the parent and database structure are tabulated for each framework under consideration. The average rmsd should be lower than about 0.5 for highly similar frameworks, between about 0.5 and about 0.75 for less related frameworks, between about 0.75 and about 1.0 for partially unrelated frameworks, and greater than about 1.0 for unrelated frameworks. In cases where the top scoring structure from the initial fitting is significantly better than the next best structure (the rmsd difference between the first and second structures on the sorted list is greater than about 0.15), this step can be eliminated. In some cases, this analysis will provide more than one good framework, with average rmsd values for the ends of the CDR loops will be within about 0.1 of each other. In these cases, each framework is selected for grafting. In combination with multiple selections for the individual CDR loops, this can create a small, combinatorial library of structures that can be analyzed.

To assemble the entire model, the selected frameworks and CDR's are overlaid with their corresponding portions of the parent structure. These transformed coordinates are then assembled into a single structure file using a text editor by insertion of the CDR coordinates into the proper places in the framework coordinate files, followed by removal of any duplicated residues from the CDR and framework coordinates. This results in the creation of new coordinate files containing a full antibody variable domain ready for analysis by energy minimization.

11. Energy Minimization of the Initial Model

According to the method, the fifth step is a computational process whereby an initial model of the modified antibody is created by replacing the atomic coordinates of the human CDRs in the acceptor structures with the atomic coordinates of the parent antibody CDRs. First, the parent CDR amino acid residues are located as characterized by the standard definitions according to Chothia's canonical definitions, and based on amino acid sequence determinations for each of the evaluated heavy chain and light chain protein segments. According to the method, the step of identifying the amino acid sequences in the CDRs is carried out by using Kabat criteria or Chothia criteria. One who is skilled in the art will be knowledgeable of the 3 CDR from light chain variable region gene segments and of the 3 CDR from heavy chain variable region gene segments. The 12 residues at the boundaries of each CDR are defined as graft junctions. These junctions represent the positions in the structure where the modified CDR loops from the previous steps are combined into the selected human framework regions. Prior to minimization, these positions may require the creation of a peptide bond if the ends of the residues in the structures are too far apart for automatic bond generation.

The following step in the computational method is energy minimization of the initial model, as a mechanism to define similarity between the parental and modified human antibody(s) as described in the previous steps. Energy calculations may be achieved by a variety of methods using programs such as CHARMm, CNS, CNX, and DeepView/Swiss-PDBViewer. An energy calculation using the GROMOS96 force field is first performed in DeepView/Swiss-PDBViewer to determine residues making good or poor steric and good or poor electronic contacts. The evaluation of appropriate contacts will be obvious to one skilled in the art. Residue-by-residue inspection is provided in the execution of the method. An outcome consisting of poor energy values will precipitate change to the residue such that the calculated energy value for the residue will be negative (favorable). These residues are inspected and changed if making particularly poor contacts. These changes to the model can include rotation of side chains to favored rotamers without bad contacts or replacement of one or many residues in areas contacting the grafted CDR sequences (including neighboring loops and Vernier residues). At this stage, potential problems in the folding of the modified antibody due to differences in either the backbone or side chain structures of the acceptor structure incompatible with the structures of the parent antibody can be addressed. Typically, this requires replacement of key residues in the acceptor framework regions with the corresponding residues from the parent antibody. The choice of structures to change is also guided by consultation of the alignment of multiple structures generated in the first step. The structure is then subjected to approximately 200 cycles of conjugate gradient minimization which will regularize the peptide bonds in the junction sites and also alleviate any small energetic violations in the model. The maintenance of the integrity of antigen binding site structure is determined by calculation of the rmsd of all atoms in the grafted structures before and after minimization. These values should be small (less than approximately 0.3 Å) in the case of a successful grafting.

This procedure of grafting and minimization of the initial model is iteratively performed for all top scoring human structures from the first step. This results in the generation of a small library, between one and ten antibodies, of heavy and light chain sequences that can be constructed and tested for desired properties. Each model may be analyzed and ranked at this point in terms of the number of residues grafted, bad contacts found in the initial model, number of mutations to the framework or grafted regions needed to alleviate poor contacts in the initial model, and rmsd of the grafted regions calculated using all non-hydrogen atoms before and after minimization. The best models will have a minimum value for all of these criteria, showing a minimal amount of non-human sequence that fits well into the new framework with few changes and potential folding problems and the smallest perturbation of the parental structure upon minimization. These best models can then be prioritized in the list relative to other models with less confidence.

12. Capability of Antibody Compositions to Recognize Features of the Parental Antibody The invention further defines the amino acids, and teaches the amino acid substitutions of template complementarity determining regions (CDR). The invention also delineates the amino acids from non-CDR framework regions and their corresponding atomic coordinates that are critical for antibody activity.

The invention improves the model created from the above steps in an iterative fashion using energy minimization calculations to guide further refinements. The execution of these computational steps leads to the delineation of an improved folding environment in the modified antibody providing the determination of critical residues and groups of residues that allow the maintenance of the parental antibody CDR structures. These critical residues may be from CDR of the parent structure or framework regions of the acceptor structure.

It is apparent that additional features of the method are of value. Several of the special circumstances are elaborated here and are necessarily covered by the method of the invention. The invention provides for the delineation of the exact structural determinants of the parental protein critical for hapten binding and antibody activity. These determinants can include residues from the six CDR from the heavy and light chains of the antibody. These determinants can include residues from only five, four, three, two, or one CDR from the heavy and light chains of the antibody. These determinants may be exclusive to only one antibody chain, the light or the heavy chain, and not include contributions from the other chain to hapten binding. These determinants can also include residues from the framework regions, including the core beta sheets and the associated loop structures connecting them as well as the N-terminal residues of the heavy or light chains of the parent antibody. The invention includes the capability of assessing important quaternary structures from the parent antibody that can be used to develop human antibody compositions with similar properties. Additionally, the invention includes the capability to determine the residues critical for proper quaternary structure and association of the heavy and light chains to maintain the properties of the parental antibody. As will be apparent to one that is skilled in the art, the invention allows for the determination of human antibody composition from protein structural criteria that will not be evident from DNA sequence-based strategies for humanizing antibodies. For example, the invention also delineates structurally relevant interactions that influence the hapten binding site, and/or binding surface where the residue is not itself involved in direct atomic interaction with the hapten, or target, but exerts its influence by association with other residues in the antibody. The influence of the residue may be local, affecting only one or two key residue positions, or it may be global, affecting the overall fold of loop and beta sheet structures in the molecule and thereby affecting the position of several key residues in the structure.

The invention directs the formation of antibody compositions where properties of specific interest for the function of the antibody are conserved. The properties can be identification of antigen epitopes that are complex, being contributed by conformational specific determinants of the target. The properties may also be formed by three-dimensional configurations of epitopes that are sequence non-contiguous, in addition to the simpler examples of sequence contiguous epitopes of importance for the target. Applications of the invention are therefore highly relevant for complex epitopes, conformation specific antibodies, minor epitopes of important proteins, temperature- and condition-dependent epitopes, catalytic antibodies, and other examples of biomodulatory functions. Where immunization has been conducted without direct knowledge of the target antigen for raising a monoclonal antibody, the invention is particularly valuable. For example, antibodies may be generated in rodents by immunization with important cells or cell populations. The hybridomas and monoclonal antibodies isolated may be characterized based on important physiologic properties of the isolated antibody, but without direct knowledge of the target protein or specific epitope recognized by the antibody. The method allows for the humanization of an antibody without knowledge of the target antigen, and therefore, is an invention of distinctive advantage with regard to second phase humanization procedures necessary for clinical development.

13. Involvement of Immunogenicity Epitopes in the Invention

The invention utilizes a series of computational steps to identify residues and groups of residues in antibody chains that are capable of triggering immune responses. In this case, immune responses are defined by the cell-mediated change in the immune repertoire such that the therapeutic antibodies are recognized as a ‘foreign’ substance. According to one skilled in the art, it is evident that epitopes of all proteins may be revealed to the immune system in the body by the presentation of metabolized protein fragments via different classes of antigen presenting cells. Antibodies, like other proteins, are metabolized to peptide fragments in cell-mediated processing events. It will be evident that Major Histocompatibility Antigens (MHC I and II) are determinants of peptide binding, and computational methods are in practice for ranking peptides with regard to binding affinities and selectivities for Class I and Class II receptors.

The method of this invention utilizes the combinatorial aspects of ranking peptide epitopes in a co-variant analysis with the invention of antibody humanization residues. The method therefore directs the identification of residues that are immunogenic and using structure-based parameters and weighting terms, selects appropriate substitution residues that negate or diminish the highly immunogenic ranking without adversely affecting the therapeutic properties of the antibody. According to the method, the additional criteria that are retained in these substitutions are the ranking based on iterative cycles of model-based energy minimization as described above. The sequence of the immunogenic peptide is analyzed to first determine key positions for mutation that will abolish or reduce MHC binding. These positions are then analyzed to determine the set of residues that will reduce the predicted MHC binding to acceptable levels. These potential substitutions are then tested in the model of the modified antibody. First, the side chain of the position to be tested is replaced with a low energy rotamer from the library of side chains in Deep View/Swiss PDBViewer of the new residue type. Some side chains will not have a low energy rotamer that does not show significant steric clashes with the surrounding structure. These substitutions are eliminated from consideration at this point. The single mutation is then subjected to approximately 200 cycles of conjugate gradient minimization in the GROMOS96 force field as implemented in Deep View/Swiss PDBViewer. The final energy of the residue is calculated and compared to the calculated energy of the parent residue type. Successful substitutions will have energy values less than zero, preferably close to the energy of the parental residue, and possibly lower than the parental residue. Substitutions that have positive energy values in this analysis have bad contacts (steric or electronic) and are eliminated from consideration at this point. The method creates a library of single mutations at key positions along the antibody sequence that can then be tested for desired binding, efficacy, and immunogenicity.

14. Definition of Antibody Compositions Created from the Invention Methodology

The invention consists of the series of computational steps described above where the output of these steps provides the creation of antibody amino acid compositions. The method defines a group of antibody amino acid sequences consisting of light chain variable domain and heavy chain variable domain components that are presented in pairwise combinations. The method creates antibody compositions of related structure to the parent antibody. The invention forms a library of antibody light chain and heavy chain amino acid sequences, referred to as a "combinatorial library". The combinatorial library of amino acid sequences relates to the method and benefits from the computational ranking of relatedness based on protein three-dimensional structure considerations. The combinatorial library further relates to the method by the ability of the invention to identify single residues, or groups of residues for refinement. The refinement criteria as part of the method include the features of structural integrity, high binding affinity to the hapten, specificity considerations, and immunogenicity.

The invention provides for the determination of a new antibody comprising a human antibody composed of a variable region light chain and a variable region heavy chain. The invention delineates the composition of each chain of the antibody comprising a linear display of amino acids from N-terminal to C-terminal residues per chain. The invention further delineates the epitopes in each chain that compose the CDR, and further, the SDR composition. The method further describes the variations in the CDR and/or SDR residues of the composition that identify additional antibodies in the structurally related antibody family of the invention. The invention determines the antibody compositions in groupings of related subfamilies, and the method specifies the per residue variation preferred according to the residues delineated in each of the subgroupings. The subgroupings may be defined by the CDR criteria of CDRL1, CDRL2, and CDRL3 for the light chain component, and by CDRH1, CDRH2, and CDRH3 for the heavy chain component. The compositions may be identified by CDR position in either of the light or heavy chain or both. As will be clear to one who is skilled in the art, the invention delineates certain CDR components for each antibody that may be of greater significance regarding binding properties of the hapten. The size of the structurally related antibody cluster may be between about 1 to about 10 antibodies, or according to the method, it may be between about 10 to about 1000 defined antibody compositions, or further according to the method, the composition of the structurally-related antibody family may be greater than approximately 1000 members. In addition to the compositional variation that is defined, the invention describes the rule for ranking and prioritization of structurally-related compositions with regard to antigen binding and specificity, and further with regard to immunogenicity.

According to the invention, it is clear that as many antibody families may be defined as there are parent antibody entries. Therefore, the implementation of the method leads to independent groupings of antibody compositions based on the defined parent antibody. The method also provides for antibody compositions to be formed from multiple parent antibodies that are related. Further, the invention relates to a single parent antibody where groups of key human antibody subtypes may be identified. According to the invention, the human antibody subtypes are delineated by the method, and are available for cross-comparison, either by computational strategies, or by the formation of antibody products for the testing of binding affinity, specificity, and immunogenicity.

The method first allows for testing of single amino acid changes in the antibody sequence from the library of sequences. This is followed by testing of these single mutation changes for desired binding and efficacy. Successful substitutions will have better binding and/or efficacy values than the original construct. These successful substitutions can then be combined in a combinatorial fashion to create double, triple, quadruple, etc. mutations to further enhance binding and efficacy properties. The method allows for testing of these potential constructs in the model to prioritize the library. The amino acid substitutions to be tested are first tabulated and grouped into potential double, triple, quadruple, etc. mutations. Each potential construct is then considered in turn. The side chains of the positions to be tested in the model are changed to a low energy rotamer from the library of side chains in Deep View/Swiss PDBViewer of the new side chain. Some sets of mutations will be structurally incompatible at this point, as there will not be found a low energy rotamer in the library that does not have significant steric clashes with the surrounding structures or other altered positions. These sets of mutations can be eliminated from consideration at this point. The modified model is then subjected to 200 cycles of conjugate gradient minimization in a GROMOS96 force field as implemented in Deep View:/SwissPDBViewer. The final energy of all modified residues is then compared to the calculated energy of the initial residues. Successful sets of mutations will show energy values less than zero for all mutation sites tested. Substitutions with calculated final energy values greater than zero are incompatible with the other potential substitutions, and these sets of mutations are eliminated from consideration at this point. The method generates a list of favorable mutation sets that can be constructed and tested for improved binding and efficacy.

15. Antibody Forms of the Invention

The invention creates a second antibody, and/or structurally related antibody family where the structural variation is primarily in the variable domain of the antibody. The method of the invention applies to parent antibodies that are from a non-human source, such as a rodent, e.g., the mouse or the rat. The method also applies to parent antibodies that are from non-rodent but mammalian sources, e.g., camel or llama. The invention also applies to the use of non-mammalian antibodies as a source of the parent antibody. The method also applies where the parent antibody is of synthetic origin, and may be synthetically derived, such as may be formed from DNA sequence libraries. According to the invention, the parent antibody may be a humanized antibody. Alternatively, the parent antibody may be a human antibody.

The invention is directed to the formation of a human antibody, namely the creation of a human antibody variable region domain, comprising a light and heavy chains in their entirety. The light and heavy chains, comprising full length antibody chains, are as well-defined and known to those skilled in the art. The antibody of the invention may be as considered a full length antibody, a fully human antibody, an antibody comprising variable and constant region domains, as are well described and of common understanding to one skilled in the art.

The invention pertains to the heterodimeric form of this variable domain, comprising a single light chain and a single heavy chain. The invention also pertains to multimeric forms of heterodimeric combinations such as tetrameric. The chimeric antibodies of the invention may therefore be formed as a full length antibody, Fab, $(Fab)_2$, $(Fab)_3$ or by additional forms as a diabody, triabody, tetrabody, minibody, a nanobody, or other form of antibody fragments preserving antigen recognition properties, as defined and described and reviewed (Holliger and Hudson; Nature Biotechnology, 2005; 23:1126-1136, the entire teaching of which is incorporated herein by reference).

According to the invention, the antibody variable region domains identified may be put into practice in a variety of additional forms, according to the practicality of the use of the form in therapy of human diseases, as will be obvious to one skilled in the art. The invention creates a second antibody, and/or structurally related antibody family where the structural variation is primarily in the variable domain of the antibody. As such, the identified structural variation the second antibody may be concentrated to one chain of the antibody, $V_l$ or $V_h$. Therefore, the single chain form of the antibody of the invention may be from either the light chain or the heavy chain, may also be referred to as ScFv, bis-ScFv, and so forth (Holliger and Hudson, 2005). Further, recombinant proteins that include a portion of the protein as an antibody domain, heterodimer, or fragment are considered as part of the invention. Fusion proteins of antibody variable domains derived from single-chain antibody configurations, and those domains in proximity to other means of heterodimerization, epitope tags, or toxin conjugations are considered as part of the invention when there is a use of the antibody variable domain properties of the fusion protein. The utility of the invention is to guide the selection of an antibody compositions for protein expression, purification, and therapeutic use.

16. Expression of Antibody Chains and Formation of Antibody Variable Domains

According to the method, the computational output forms an amino acid sequence comprising a light chain polypeptide, and a corresponding heavy chain amino acid sequence. The method may further comprise the step of constructing a nucleic acid library comprising DNA segments encoding the amino acid sequences of the selected members of the designated antibody variable region gene segment library. According to the method this library may be composed of one or more variants with one or more variations in residue selections for either light and/or heavy chain gene segments. As such, it is defined a degenerate library whereas the level of degeneracy may be severely restricted.

Accordingly, the method comprises the steps of introducing the DNA segments in the degenerate nucleic acid library into cells of a host organism; expressing the DNA segments in the host cells such that recombinant antibodies comprising the amino acid sequences are produced in the cells of the host organism; and screening the recombinant antibody that binds to a target antigen with affinity higher than $10^{-5}$ M. Under some circumstances, antibodies with lower affinity may be desirable. Additional modifications based on the determination of the affinity of the modified antibody to the target antigen may be warranted.

The recombinant antibodies may be fully assembled antibodies, Fab fragments, Fv fragments, or single chain antibodies.

The host organism includes any organism or its cell line that is capable of expressing transferred foreign genetic sequence, including but not limited to bacteria, yeast, plant, insect, and mammals.

The recombinant antibodies may be fully assembled antibodies, Fab fragments, Fv fragments, or single chain antibodies. For example, the recombinant antibodies may be expressed in bacterial cells and displayed on the surface of phage particles. Alternatively, Fv may be secreted from bacterial cells. Many cell lines from a variety of species are applicable for protein expression of antibody chains and fusion proteins. Of note, some of the particular types of cells include, but are not limited to *E. coli, Bacillus subtilis*, SF9 cells, *Drosophila melanogaster* cells, *Saccharomyces cerevisiae* and other yeasts, C129 cells, 293 cells, Neurospora, BHK, CHO, COS, and HeLa cells, fibroblasts, Schwanoma cell lines, immortalized mammalian myeloid and lymphoid cell lines, Jurkat cells, mast cells and other endocrine and exocrine cells, and neuronal cells. Examples of mammalian cells include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells, osteoclasts, chondrocytes and other connective tissue cells, keratinocytes, melanocytes, liver cells, kidney cells, and adipocytes.

Alternatively, the recombinant antibodies displayed on phage particles may be a single-chain antibody (scFv) containing $V_H$ and $V_L$ linked by a peptide linker.

The target antigen to be screened against includes small molecules and macromolecules such as proteins, peptides, nucleic acids, lipids, glycoprotein conjugates, and polycarbohydrates.

The above methods may further comprise the following steps: introducing the modified antibody DNA segments in the form of nucleic acid or degenerate nucleic acids into cells of a host organism; expressing the DNA segments in the host cells such that recombinant antibodies containing the amino acid sequences of the modified antibody library are produced in the cells of the host organism; and selecting the recombinant antibody that binds to a target antigen with affinity higher than about $10^{-4}$M. The binding affinity of the modified antibody to the target antigen is optionally higher than about $10^{-7}$ M, optionally higher than about $10^{-8}$ M, optionally higher than about $10^{-9}$ M, optionally higher than about $2 \times 10^{-9}$ M, optionally higher than about $5 \times 10^{-9}$M, optionally higher than about $8 \times 10^{-9}$ M, optionally higher than about $1 \times 10^{-10}$ M, optionally higher than about $2 \times 10^{-10}$ M, optionally higher than about $5 \times 10^{-10}$ M, optionally higher than about $8 \times 10^{-10}$ M, or optionally higher than about $1 \times 10^{-11}$ M.

17. Determination of Antibody Activity

The binding affinity of the modified antibody to its antigen may vary, depending the form of antibody being tested. The modified antibody being tested may be in the form of a single-chain antibody (scFv) comprising $V_H$ and $V_L$ designed by using the methodology of the present invention. Optionally, the selected antibody being tested may be in the form of a Fab comprising $V_H$ and $V_L$ designed by using the methodology of the present invention. Presumably due to its higher conformational flexibility and instability, the binding affinity of the selected antibody in the form of scFv may be 1-2 magnitude lower than that in the form of Fab.

The designed protein is purified or isolated after expression according to methods known to those skilled in the art. Examples of purification methods include electrophoretic, molecular (tagging methodologies leading to new epitopes), immunological and chromatographic techniques, including ion exchange, hydrophobic, affinity, size exclusion, and reverse-phase HPLC chromatography, and chromatofocusing. The degree of purification necessary will vary depending on the use of the designed protein. In some instances no purification will be necessary.

Also according to any of the embodiments described above, the designed proteins can be screened for a desired function, e.g., a biological function such as their binding to a known binding antigen partner or some fragment of that antigen representing an epitope of significance for antibody recognition, physiological activity, stability profile (pH, thermal, buffer conditions), substrate specificity, immunogenicity, toxicity, etc.

In the screening using a cell-based assay, the designed antibody may be selected based on an altered phenotype of the cell, e.g., in some detectable and/or measurable way. Examples of phenotypic changes include, but are not limited to gross physical changes such as changes in cell morphology, growth, viability, adhesion to substrates or other cells, and cellular density; changes in the expression of one or more RNAs, proteins, lipids, hormones, cytokines, or other molecules; changes in the equilibrium state (i.e., half-life) or one or more mRNAs, microRNAs, proteins, lipids, hormones, cytokines, or other molecules; changes in the localization or processing of one or more RNAs, proteins, lipids hormones, cytokines, or other molecules: changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptibility, latency, adhesion, and uptake of viruses and bacterial pathogens.

According to any of the above embodiments, the designed antibodies may be synthesized, or expressed as fusion proteins with a tag protein or peptide. The tag protein or peptide may be used to identify, isolate, signal, stabilize, increase flexibility of, increase degradation of, increase secretion, translocation or intracellular retention or enhance expression of the designed proteins.

The invention further provides: isolated nucleic acid encoding the antibody; a vector comprising that nucleic acid, optionally operably linked to control sequences recognized by a host cell transformed with the vector; a host cell comprising that vector; a process for producing the antibody comprising culturing the host cell so that the nucleic acid is expressed and, optionally, recovering the antibody from the host cell culture. Each of these methodologies is standard in the field of protein expression and will be obvious to one skilled in the art.

18. Therapeutic and Diagnostic Utility of Human Antibodies of the Invention

The method applies to the formation of a therapeutically useful antibody for human disease intervention. Because the invention consists of the derivation of new antibodies, the utility of the newly created antibody can be directed by the role of the antigen, hapten, protein, or other macromolecule in human disease. The antibodies of the present invention will typically find use individually in treating any disease susceptible to monoclonal antibody-based therapy. The therapeutic antibody can be used for passive immunization or the removal of unwanted cells or antigens, such as by complement mediated lysis, all without substantial immune reactions (e.g., anaphylactic shock) associated with many prior antibodies that develop antibody-based immunogenicity.

The invention generally relates to the formation of therapeutic antibodies having sufficient binding affinity and specificity to target molecules associated with disease states in the human. The invention pertains to the therapeutic antibodies that have limited and restricted immunogenicity in the human such that the therapeutic antibody has a preferred property as a therapeutic agent for use in humans.

The invention applies to antibodies that can be a therapeutic. Each antibody of the invention is an important therapeutic for one or more human diseases. Collectively, antibodies created by the invention are useful for a wide variety of human diseases and human disorders of many different types. The application of the invention has utility from the ability to create therapeutic antibodies that recognize their target molecules with high specificity, as is known to be the properties of antibody molecules generally. The invention pertains to the ability to treat disease by providing a human antibody that is able to bind, neutralize, cause the aggregation, degradation or elimination of the target in a human body. The invention also relates to classes of antibodies that may be beneficial to human health, and for treatment of human disease, where the antibody therapeutically has an agonist property. In other words, the effect of such a therapeutic antibody is in the stimulation of the effect of the target protein. The invention relates to the ability of the antibody to stimulate cell-mediated and/or humoral immune responses that contribute to the therapeutic activity of the antibody. The invention relates to the formation of therapeutic antibodies that may promote utility of other agents, such as may be applied in a therapeutically useful way, such as in the formation of vaccine function in the human body. As such therapeutic antibodies of the invention may promote better vaccine formation.

The diseases pertinent to the invention include, but are not limited to, diseases of cancer, immune and inflammatory disorders, cardiovascular and metabolic diseases, neurological and neurodegenerative diseases. The application of therapeutic antibodies of the invention includes treatment of chronic diseases and disorders, such as diabetes, obesity, Alzheimer's disease, rheumatoid arthritis, Crohns disease, inflammatory bowel disease, transplantation, graft versus host disease, multiple sclerosis, polycystic kidney disease, end-stage kidney disease, thrombosis, and chronic obstructive pulmonary disease. Other applications include the invention relates to the development of therapeutically useful antibodies for muscle wasting, cachexia, stem cell regulation and cell replacement therapies, anti-viral and anti-infective strategies such as multidrug resistant tuberculosis. The invention is important to the development of antibodies targeting diseases and disease states such as bone marrow transplantation, asthma, osteoporosis, allergy, macular degeneration, deep vein thrombosis, stroke, nephritis, sepsis, pain, acute chronic pain, lupus, platelet adhesion disorders, muscular dystrophy, psoriasis, HIV-related disorders, HIV neutralization, ulcerative colitis, pulmonary fibrosis, hemorrahagic shock, congestive heart failure, hypertension, type I or type II diabetes, neuropathic pain. Lou Gehrigs disease, schizophrenia, lipid dyslipidemia diseases, cholesterol metabolism diseases, diseases of aberrant cholesterol transport and loading, atherosclerosis, and disorders of carbohydrate metabolism.

The invention relates to disease of cancer and cancer therapeutics applied to conditions such as colorectal, breast, pancreatic, prostate, ovarian, renal, lung, stomach, bladder, skin, lymphomas, Hodgkins disease, non Hodgkins lymphoma, leukemias, acute myeloid leukemia, melanomas, and a variety of solid tumor cancers. The invention is pertinent to metastasis, since therapeutic antibodies are able to target cell interactions in cancer. The therapeutic antibody of the invention may target the angiogenesis pathway and act by means of neutralizing angiogenesis. The antibody may be useful to interfere with tumor cell growth, adaptation to hypoxia, cell-cell adhesion changes, and influence the stability of the tumor microenvironment in a therapeutically efficacious manner. The antibody of the invention may be directed to targets relevant to cancer that may be glycoproteins, lipids, complex carbohydrate structures, to cell signaling receptors, cytokines, growth factors, secreted proteins, or other classes of proteins important to tumor formation change and perpetuation.

The invention pertains to antibodies that recognize targets in disease that are available to the vascular bed or available to lung mucosal surfaces, or by administration topically to skin surfaces. Since the invention primarily is a method for building new antibody compositions for therapeutic utility it is also relevant to applications where antibody chains can be expressed in a therapeutically relevant manner inside the cells Therefore, additional applications to the invention are revealed for intracellular protein targets of disease.

The invention has an important application to the development of therapeutic antibodies that may be used in the treatment of drug abuse, addiction, and overdose. Examples include the neutralization and/or metabolism of cocaine, morphine, nicotine, PCP, MDMA, caffeine, methampihetamine, and other agents of drug abuse. Applications include the development of therapeutic antibodies that have high binding affinity to the hapten and thereby have utility by the ability to neutralize the effects of the hapten, or metabolites thereof, in the human body. The therapeutic antibodies may also be of the invention by including antibodies that are catalytic, and cause the metabolism, neutralization, deactivation, hydrolysis, or other modification of the target molecule such that the target molecule is rendered ineffective as an agent of abuse.

The invention also pertains to the creation of an antibody therapeutic that would neutralize the effects of pathologic bacterial, protozoa, and/or viral-induced disease states in the human body. The application of the invention includes pathogens of bacterial origin, with antibody compositions useful as a therapeutic against the bacterial pathogens relevant to bacteria infections by *Bacillus anthracis* and other zoonotic infections (plague, tularemia, brucellosis, leptospirosis, glanders, melliodosis), from actinomycete infections, entercoccal infections, from legionellosis, Lyme disease, nosocomial infections, rickettsial and related diseases (ehrlichiosis, anaplasmosis, bartonellosis), typhus, Q fever, tickborne spotted fevers, spepsis, staphylococcal infections, urinary tract infections vector-borne bacterial infections. Also, the therapeutic antibodies will apply where the targets are directed from epitopes of fungi and fungal diseases, such as aspergillosis, blastomycosis, candidiasis, coccidioidomycosis, cryptococcosis, histoplasmosis, *Pneumocystis carinii*, and other primary and opportunistic infections. It will also apply to circumstances of antibacterial and antifungal drug resistance. The invention is relevant to targeting *Clostridium botulinum*, *Brucella* species, *Yersinia pestis*, *Rickettsia prowazekii*, *Salmonella* species, *Francisella tularensis*, *Salmonella Typhi*, *Vibrio cholerae*, and *Neisseria meningitidis*. The antibodies may be directed against the pathologic organism such that the effect of the therapeutic antibody is to neutralize the absorption, growth, replication, or pathologic impact of that organism in the human body. The invention relates to the composition of therapeutic antibodies that may be created against epitopes of parasites such as *Shigella*, schistosomiasis, lymphatic filariasis, Helminth infections, leishmaniassis, malaria, camebiasis cryptosporidiosis, cyclosporiasis, giardiasis, roundworms, tapeworm infections, and other parasites.

The therapeutic antibodies of the invention may be directed against toxins from these pathogens, such as Anthrax toxin, ricin, botulinum toxin, Staphylococcal enterotoxin Bf, Episilon toxin, where neutralization of the toxin has important therapeutic benefit as an emergency therapy in bioterrorism.

The invention pertains to the development of therapeutic antibodies against viruses such as influenza, avian influenza, Dengue fever, ebola, Marburg, hepatitis, smallpox, filoviruses, arenaviruses, Nipah viruses, Hantaviruses, Lassa fever viruses, and viruses causing viral encephalitis (alphaviruses [e.g., Venezuelan equine encephalitis, eastern equine encephalitis, western equine encephalitis]). Norwalk noravirus infections, rotaviruses, and flaviviruses (West Nile virus).

The invention pertains to the use of antibodies in general as a therapeutic applied to any human diseases. The invention may be applied to the development of human antibodies used therapeutically and by differing routes of administration, such as by injection, topical application, nasal, emulsion, and nebulized administrations. The application of this technology will include the production of a pharmaceutical composition comprising formulating the human antibody or antibody fragment with or without a carrier for drug administration. The antibodies of the present invention can also be used as separately administered compositions given in conjunction with chemotherapeutic or immunosuppressive agents. A pharmaceutical composition of the invention comprises the use of the subject antibodies in immunotoxins. A pharmaceutical composition of the present invention comprises the use of antibodies of the invention as in immunotoxins. Immunotoxins are two component biomolecules that have utility by killing targeted cells. One component is a cytotoxic agent causing cell death when attached or absorbed. The second component, the "delivery vehicle," is an antibody fragment in this invention that provides a means for delivering the associated toxic agent to the target cell type. The two components may be chemically bonded together by any of a variety of well-known chemical procedures, or genetically engineered as a fusion protein. Production of various immunotoxins is well known with the art. Single or multiple administrations of the compositions can be carried out with dose levels and pattern being selected by the treating physician. In any event, the pharmaceutical formulations should provide a quantity of the antibody(ies) of this invention sufficient to effectively treat the patient.

In addition to therapeutic applications, humanized antibodies of the invention will find utility as diagnostic agents for disease. Relevant applications for diagnostic antibodies will be evident from cancer, inflammatory disease, and cardiovascular applications where the validated antibody is in clinical use. Human antibodies have the added advantage of reduced interference with immune components that may influence diagnostic testing results. A range of clinical laboratory testing applications are evident for all antibody products including those of human origin, including rapid response detection of pathogens, toxins, tumor antigens, and biomarkers of human disease. In addition to clinical diagnostic applications, it is projected that newly developed human antibodies of the invention will be pertinent to imaging and diagnostic applications for biomedical research purposes. For diagnostic purposes, the antibodies may either be labeled or unlabeled. Unlabeled antibodies can be used in combination with other labeled antibodies (second antibodies) that are reactive with the humanized antibody, such as antibodies specific for human immunoglobulin constant regions.

EXAMPLE 1

Formation of a Humanized Antibody by Derivation of a murine Monoclonal Antibody, Anti-Lewis X Antibody The Structure Grafting method (FIG. 1) of the invention was used to modify the murine anti-Lewis X antibody. This example is included to demonstrate the utility of structural information in the modification of antibodies while conserving structural elements essential for antigen binding. In particular, there is a specific residue in the framework of the parent antibody that appears to be critical for positioning of the CDRs in the structure. These interactions are maintained in the modified antibody formed by the method. The parent antibody has a solved crystal structure at a resolution of 1.8 Å was obtained from the Protein Data Bank (code 1UZ8). This structure contains two antibody molecules in the asymmetric unit. The rmsd for the two molecules is 0.59 Å calculated using 430 alpha carbon atoms. Since the two chains are ver similar in the structure, the first chain was used for all subsequent steps in the modification.

The variable region of the parent antibody was defined as residues 1-108 for the light chain and residues 1-113 for the heavy chain. This variable region was then superposed onto published human and humanized antibody structures using the Iterative Magic Fit command in Deep View/Swiss-PDB-Viewer. Three structures fit very well onto the parent structure—1DEE, 1NL0, and 8FAB. These are highlighted in red in the distribution of rmsd values obtained in the database search outlined in FIG. 2A. This example displays the importance of quaternary structure in the search for a human scaffold to modify. The majority of the structures in the search were observed to fit very well in the heavy chain, however, the light chain regions did not fit well. This appeared to be a consequence of misalignment of the two chains in a global fitting. For instance, for structure 1AD0, the overall rmsd of the fitting to the parent structure was 1.03, however, for the individual heavy and light chains the rmsd values are 0.67 Å and 0.94 Å respectively. Thus, the chains fit well to one another, but the relationship of the chains to each other is not optimal for modification and this structure can be removed from further consideration. Note in the distribution of rmsd values for the fitting of 1UZ8 to the database that there is a clear gap between the best three structures and the next best structure in the database, suggesting that the three highlighted structures are the best starting points for further modification.

Figure 2:
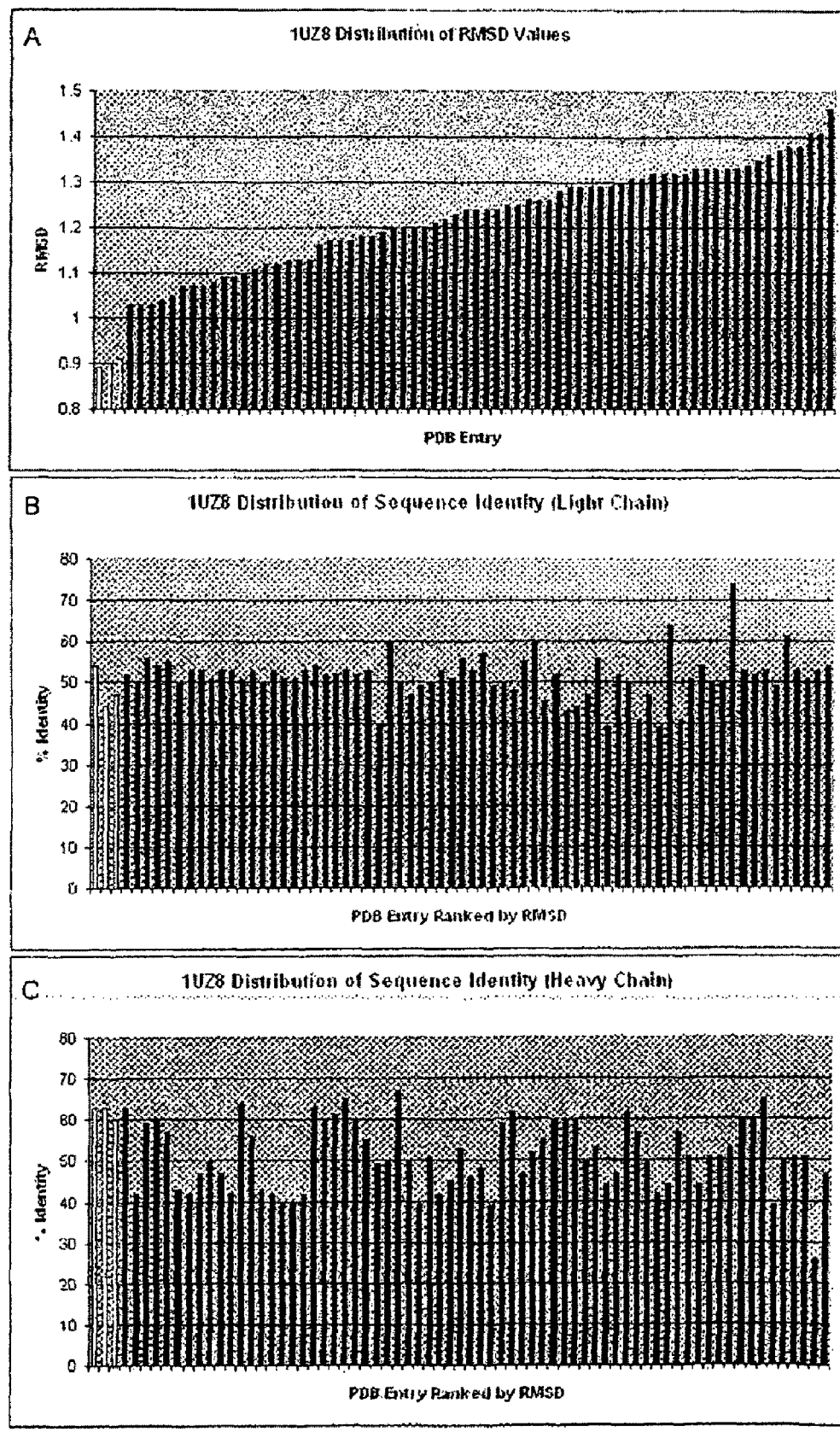
FIG. 2 depicts bar graphs where (a) depicts the distribution of rmsd values obtained by alignment of a parental antibody 1UZ8 fv region to the database of human fv structures available in the Protein Data Bank. Highlighted are the three best scoring acceptor structures—1DEE, 1NL0, and 8FAB; (b) represents the sequence identity of the light chain variable regions of 1UZ8 and human structures in the database as ranked by rmsd score and shaded as in (a); and (c) represents the sequence identity of the heavy chain variable regions of 1UZ8 and human structures in the database as ranked by rmsd score and shaded as in (a)

Furthermore, examination of the database shows a lack of correlation between structural similarity as determined by rmsd and sequence identity. In FIGS. 2B and 2C, the sequence identity between 1UZ8 and each human structure in the database is displayed ranking the human structures by rmsd as in FIG. 2A. The three best fit structures in terms of rmsd are highlighted in red. As is clear from the figures, use of the most similar human framework in terms of sequence identity will not result in the best framework in terms of structure. Thus, a sequence based approach may not select the most appropriate framework, since the structures may well be divergent in key positions in the top scoring frameworks based on sequence identity. The method outlined here should provide a superior alternative to sequence based methods.

Before creation of the model, the specificity determining residues of the parent antibody were determined. First, all residues within 5 Å of the hapten in the cocrystal structure of 1UZ8 were identified. These residues were Tyr27D, Tyr32, Tyr34, Gln50, Asn91, Leu92, Glu93, Val94, and Trp96 from the light chain and Trp33, Trp47, Glu50, Asn58, Glu95, Thr96, Gly97, and Thr98 from the heavy chain. The CDR sequences were then defined according to Chothia canonical sequences. Each residue in the CDR regions were then inspected for addition to the SDR list. In the light chain, residues making key electrostatic interactions to stabilize loop structure included Lys27 and Glu93, whose side chains make a salt bridge, Ser27A, whose side chain makes a hydrogen bond to the main chain nitrogen of Leu27C and Asn28, whose side chain makes a hydrogen bond with the side chain oxygen of Tyr32. In the heavy chains these residues included Asp53 and Ser55, whose side chains make a hydrogen bond, Thr60, whose side chain makes a hydrogen bond to the main chain oxygen of Trp47, Pro61 and Leu63, whose main chain atoms are making a hydrogen bond, and Asp 10 1, whose side chain makes a hydrogen bond to the side chain oxygen of Tyr36. Additionally, Gly29, Met51, and Pro95 of the light chain and Pro53 of the heavy chain have main chain conformations that suggest these residues are key or loop structure and were included in the SDR list. Lastly, Ala89 and Ala55 of the light chain and Ser35 of the heavy chain were added to the list. These residues occupy positions in the structure where a small side chain appears to be needed to accommodate the ligand or various loop structures. These SDR residues are highlighted in FIG. 3 in boldface and italics.

Figure 4:
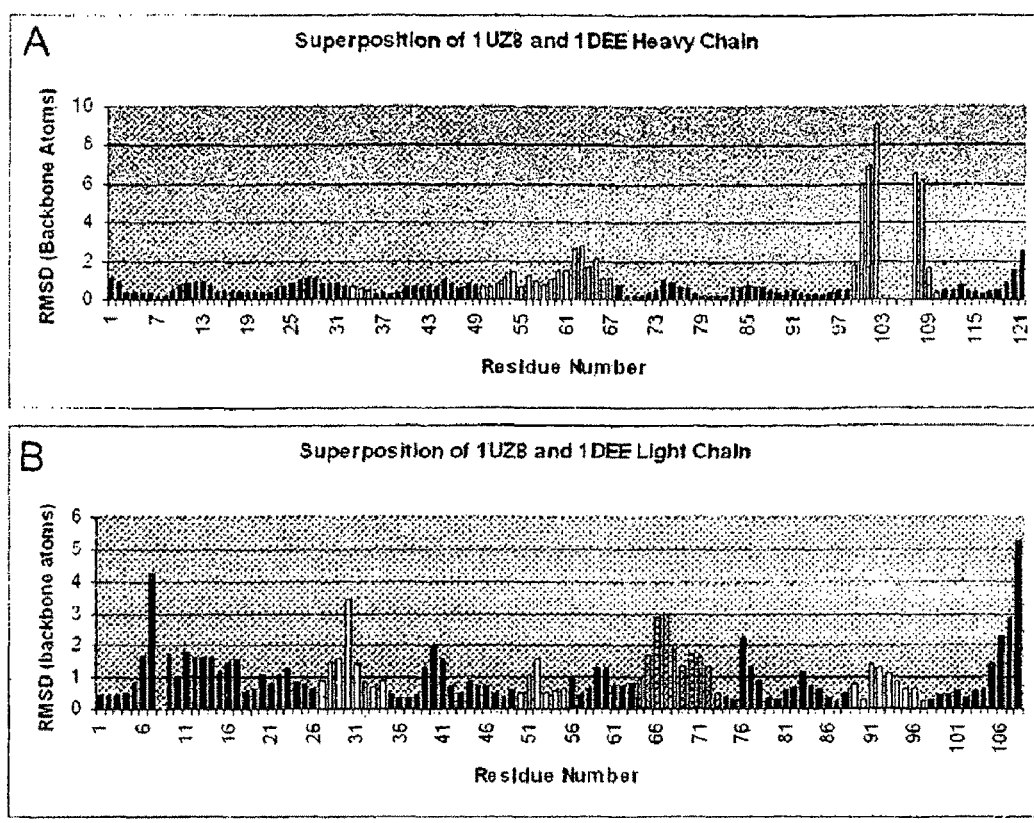
FIG. 4 depicts residue by residue display of rmsd for structurally related residues calculated using the backbone atoms for the superposition of the variable regions of structures 1UZ8 and 1DEE for the heavy (A) and light (B) chains. Bars highlighted in white are the residues used for grafting. The residues in gray (64-73) are suggested to be in an altered conformation from the method.

The structure of 1DEE was first used for replacement of the coordinates of the CDR structures with coordinates from the parent antibody structure 1UZ8. The structures of 1UZ8 and 1DEE variable regions were then superposed. Graft sites were then determined starting at the ends of the CDR regions as defined by Chothia. The site was then moved toward the center of the loop until either the structures diverged significantly in the overlay or an SDR residue was reached. The exception to this was Trp47 of the heavy chain, which is conserved in structure and sequence in both the parent and the acceptor antibody structures. In the structure-based sequence alignment in FIG. 3, the final sequences chosen for exchange are highlighted in italics. In FIG. 4, the rmsd for backbone atoms of structurally equivalent residues is displayed.

The coordinates of the italicized sequences in FIG. 3 from the 1DEE structure were replaced by the equivalent coordinates from the structure-based alignment from 1UZ8. An initial energy calculation of the resultant model was preformed in Deep View/Swiss-PDBViewer. The calculation showed several residues making poor contacts in the model. One of these, Cys23 of the light chain, is located at the junction of the two structures, and was not changed prior to minimization. More interesting was a severe clash between the side chains of Leu27, Thr31, Leu33, and Met51 and the backbone atoms of Gly66, Gly68, and Phe71 of the light chain (FIG. 3). Upon further inspection, the source of this clash was determined to be a difference in the conformation the loop formed by residues 64-73 (dark grey bars in FIG. 4). This structural difference exists despite good sequence conservation between the parent and human antibodies in this region. The key difference in the sequences appears to be at position 64, where the human structure has a glycine and the parent structure has a serine. The longer side chain of the serine in the parent structure makes a steric interaction with the side chain of Trp35. This side chain interaction may be the source of the conformational difference in the loops between the two structures. In fact, the equivalent residue in the 8FAB structure is also a serine, and this loop has an altered conformation compared to the 1DEE structure as well. Thus, this loop has a flexible conformation despite the sequence conservation. The Gly64 was changed to serine, and the coordinates of the loop from 1DEE were substituted with the coordinates from 1UZ8 (residues 64-73 in FIG. 3). This single replacement is easily discovered using the structural overlays as a guide. While sequence based methods may arrive at this same conclusion, many constructs would be required to be synthesized and tested, showing an advantage of use of structural models in the process. After 200 cycles of conjugate gradient minimization of this model in Deep View/Swiss-PDBViewer the model was free of poor contacts. The integrity of the binding site was maintained as evidenced by the low rmsd of 0.21 Å calculated for all atoms (524 atoms total) in the grafted regions before and after minimization. The sequence of the final model is shown in SEQ ID-7 and SEQ ID-8.

Next, the other two top scoring human structures were used for replacement of coordinates of the CDR structures with coordinates from the parent structure, 1UZ8, and initial models were generated for each. Graft sites were initially defined and then redefined in the same manner as before. In the structure-based sequence alignment in FIG. 3, the final sequences chosen for exchange are highlighted in orange for 1NL0 and in green for 8FAB.

The initial energy calculation of the model derived from 1NL0 as an acceptor structure showed nine bad contacts in the light chain and none in the heavy chain. The contacts between residues in CDR-L1 (Ser27A, Thr31, and Leu33), Met51, and the loop formed by residues 64-73 (Lys66, Asn69, and Ala71) were similar to the bad contacts encountered in the grafting above. Therefore, the same section of loop structure was grafted (residues 63-73) as in the case where 1DEE was the acceptor molecule. This alleviated many of these contacts and once again can be attributed to the presence of a larger serine side chain at position 64 in the parent molecule as opposed to a glycine in the acceptor molecule. The other pair of poorly contacting side chains in the initial model, from Tyr34 and Tyr49, were minimized without further modification, After 200 cycles conjugate gradient minimization as implemented in Deep View/Swiss Prot PDBViewer, all bad contacts were alleviated. The final structure of the model shows good conservation of the parental structure. The rmsd calculated using the 569 non-hydrogen atoms grafted onto the acceptor structure was 0.2 Å comparing the structures before and after minimization. The sequence of the final model is shown in SEQ ID-9 and SEQ ID-10.

The initial energy calculation of the model derived from 8FAB as an acceptor structure showed eight bad contacts in the light chain and two bad contacts in the heavy chain. In the heavy chain, the side chains of Arg98 and Phe100 were making small clashes and were minimized without further modification. The light chain showed four pairs of poorly interacting residues. The side chain of Glu3 was altered to a different low energy rotamer from a library in Deep View/Swiss Prot PDBViewer to alleviate a bad contact with the backbone of Ser26. The side chains of Leu33 and Val70 were in close contact in the initial model. To remove this contact, the side chain of Leu33 was mutated back to the alanine side chain from the acceptor structure. Even though this residue is in the grafted section of the structure. Leu33 is not a SDR and therefore changes to this position are likely not to affect activity of the modified construct, The side chain of Met51 was observed packing close to the side chain of Thr65. This is the only poor contact observed using this framework between the CDR regions and the loop formed by residues 63-73. 8FAB, like the parental antibody, has a serine at position 63 and thus this loop adopts a conformation more like the parental antibody. In this case, a mutation of the Thr65 side chain to the glycine present at this position in the parental antibody was sufficient to alleviate any bad contacts in this region. Lastly, a small clash between the side chains of Gln90 and Ile96 was alleviated by alteration of the rotamer of the side chain of Ile96 prior to minimization. After 200 cycles of conjugate gradient minimization, there were no bad contacts in the model. The final model shows good conservation of the parental antibody structures, since the rmsd calculated using the 505 non-hydrogen atoms from the grafted structures is 0.18 Å comparing the structures before and after minimization. The sequence of the final model is shown in SEQ ID-11 and SEQ ID-12. The fact that less parental sequence was needed to be grafted into this structure and the limited number of changes to the model guided by the initial energy calculation suggest that this model is the most promising for a modified antibody with desired properties. However, the first two models generated are valid for testing as well.

Finally, the grafted sequences were inspected to determine if the amount of parent sequence could be further reduced. Each residue in the red sections of FIG. 3 was inspected (omitting the SDR residues, which were not considered for changes). The structures of the top scoring human antibody structures 1DEE, 1NL0, and 8FAB were superposed onto the 1UZ8 structure and the model created from the grafting. This superposition was consulted for each position in the CDR regions to suggest possible substitutions at that position if the structures overlaid well. Each residue was replaced in the model with a low energy, favored rotamer of the mutated side chain and the model subjected to 200 cycles conjugate gradient minimization. The final energy of the mutated residue was then tabulated to determine if the mutation was compatible with the modified antibody structure. The results of these calculations are tabulated in FIG. 5. The successful substitutions were then incorporated into a combinatorial library of CDR sequences for further analysis. The final library consists of 14 possible sites of mutation with 20 possible single mutations that could be constructed and tested for improved binding properties and efficacy. Additional double, triple, etc. mutations could be constructed after further analysis to continue to tune the properties of the modified antibody.

EXAMPLE 2

Formation of a Humanized Version of a Murine Monoclonal Antibody to uPAR Using the Structure Grafting Method (FIG. 1)

The present methods were used to generate humanized versions of a murine monoclonal antibody that binds to uPAR and inhibits the downstream signaling of the receptor. Urokinase-type plasminogen activator (uPA) binds to uPAR after activation by proteolytic cleavage. The activated uPAR then associates with a number of effector molecules, including several integrins and vitronectin (Wei et al., 1996; Science 273: 1551-5; Xue et al., 1997; Cancer Res. 57: 1682-9; Carriero et at, 1999; Cancer Res. 59: 5307, the entire teachings of which are incorporated herein by reference). These downstream effectors then lead to cell proliferation, migration, and invasion. Since proliferation, migration, and invasion are integral processes for the progression and metastasis of cancers, inhibition of the association of uPA and uPAR or inhibition of the activity of uPAR has been proposed as a potential therapy in cancer, uPA and uPAR are overexpressed in many cancer types including breast, colon, pancreatic, and prostate and high levels of uPA and uPAR correlate with a poor prognosis in some cancers (Mizukami et al., 1994; Clin Immunol Immunopathol 71. 96-104; Hsu et at, 1995; Am J Pathol 147:114-23; de Witte et al. 1999; Br J Cancer 79:190-8; Stephens et al. 1999; J Natl Cancer Inst 91:86974; Ganesh et al., 1994; Lancet 344:401-2; Pedersen et al., 1994; Cancer Res 54.4671-5; Andreasen et al., 1997; Int J Cancer 72:1-22; Duffy 2002; Clin Chem 48:1194-7; Look et al., 2002; J Natl Cancer Inst 94:116-28; Takeuchi et alt, 1993; Am J Gastroenterol 88:1928-33; Cantero et al, 1997; Br J Cancer 75: 388-95, the entire teachings of which are incorporated herein by reference).

The uPAR signaling pathway can be targeted for inhibition in several ways. There are a number of linear and cyclic peptides that have been discovered for the inhibition of uPA/uPAR binding (U.S. Pat. Nos. 7,045,504; 7,026,282; 6,906,032; 6,872,702; 6,514,710; 6,030,940; 5,942,492; and 5,656,726, the entire teachings of which are incorporated herein by reference). Peptides that can inhibit the association of uPAR with downstream effector molecules (U.S. Pat. No. 6,794,358, the entire teaching of which is incorporated herein by reference) have also been discovered. Lastly, uPAR expression can be inhibited by either an antimessenger oligonucleotide (U.S. Pat. No. 5,872,106, the entire teaching of which is incorporated herein by reference) or specific peptides (US Application 20050048045, the entire teaching of which is incorporated herein by reference).

An antibody that binds to uPAR and inhibits the downstream activities of uPAR may be a pathway to recognizing the potential therapeutic value of uPAR as an anti-cancer target. An antibody that binds to uPAR without affecting uPA/uPAR association was recently shown to have beneficial effects in a mouse model (Bauer et al., 2005: Cancer Res. 65:7775-81, the entire teaching of which is incorporated herein by reference). Mice were injected with human pancreatic cancer cells and 4 days later were treated with the anti-uPAR antibody, ATN-658. The antibody completely inhibited retroperitoneal tumor invasion as well as inhibiting tumor size. These studies strongly suggest that an anti-uPAR antibody can have significant therapeutic value by reducing tumor growth and metastasis. Since the crystal structure of an anti-uPAR antibody raised against the same antigen as ATN-658 recently became available (Huai et al., 2006 Science 311:656-9, the entire teaching of which is incorporated herein by reference) a structure-based method of humanization was used to create versions of the antibody that can be used as therapies in human patients.

The Structure Grafting method outlined above was used to modify the murine monoclonal antibody ATN-615 to create antibodies with potential therapeutic value against cancer. The solved crystal structure of antibody ATN-615 in complex with soluble uPAR and a N-terminal fragment of uPA at a resolution of 1.9 Å was obtained from the Protein Databank (code 2FD6). The variable region of the parent antibody was defined as residues 1-107 from the light chain and residues 1-113 from the heavy chain. This variable region was then superposed onto published human and humanized antibody structures using the Iterative Magic Fit command in Deep View/Swiss-PDBViewer. Four structures fit well onto the parent structure named as HuFR1, HuFR2, HuFR3, and HuFR4 (white bars, FIG. 6A). Note in the distribution of rmsd values for the fitting of 2FD6 to the database that there is a clear gap between the best four structures and the next best structure in the database, suggesting that the four highlighted structures are the best starting points for further modification.

Figure 6:
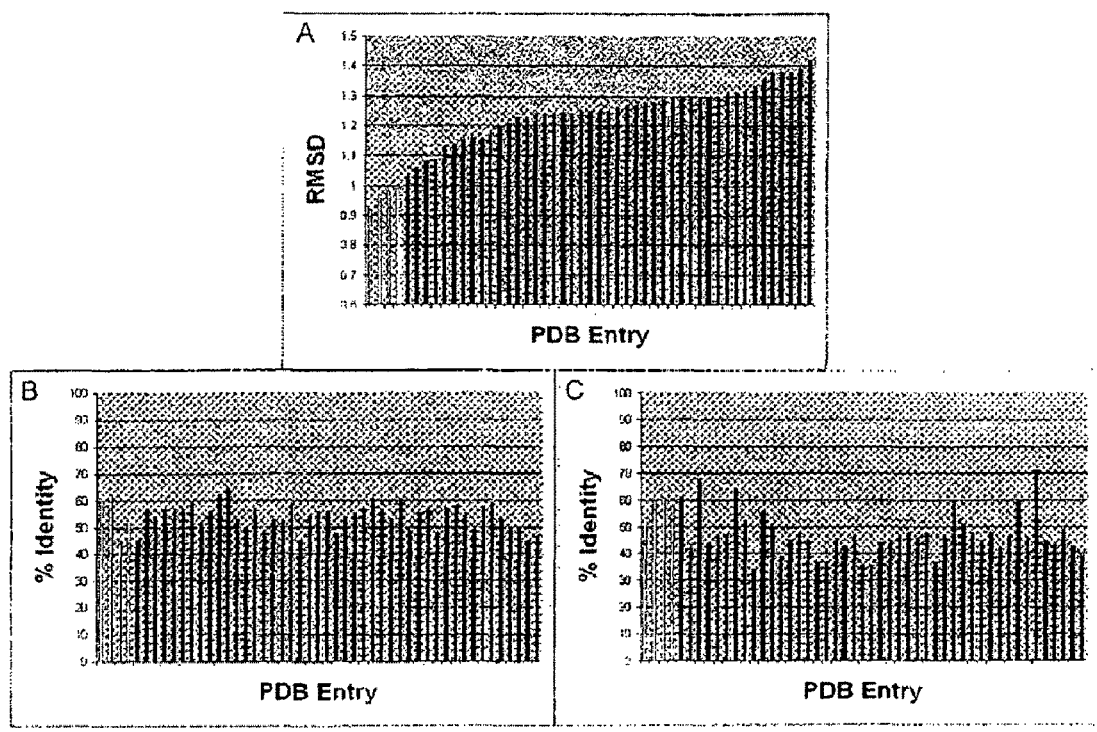
FIG. 6. A. Results of structural overlay of antibody ATN-615 structure against the database of human structures. The top scoring structures are highlighted in white bars. B. and C. Sequence identity of the light (B) and heavy (C) chains of antibody ATN-615 compared to the human structures in the database, sorted by structural similarity.

Furthermore, examination of the database shows a lack of correlation between structural similarity as determined by rmsd and sequence identity. In FIGS. 6B and 6C, the sequence identity between 2FD6 and each human structure in the database is displayed ranking the human structures by rmsd as in FIG. 6A. The four best fit structures in terms of rmsd are highlighted in white. As is clear from the figures, use of the most similar human framework in terms of sequence identity will not result in the best framework in terms of structure. Thus, a sequence based approach may not select the most appropriate framework, since the structures may well be divergent in key positions in the top scoring frameworks based on sequence identity. The method outlined here should provide a superior alternative to sequence based methods.

Before creation of the model, the specificity determining residues of the parent antibody were determined. First, all residues within 5 Å of the soluble uPAR molecule in the complex structure were identified. These residues included Ser31, Tyr32, Trp91, Asn92, Tyr93, and Phe96 from the light chain and Tyr33, Trp50, Phe52, Asp55, Asn56, Thr57, Glu58, Trp95, and Trp99 from the heavy chain. Each SDR residue and other Chothia-defined CDR residues were then inspected individually for inclusion on the list of SDR if the residue was observed to have structural features key to proper folding and positioning of the SDR residues. Pro94 of the light chain and Pro97 of the heavy chain were added to the list to maintain the backbone conformation of these positions in the modified constructs. An interchain salt bridge was noted between the side chains of Glu50 of the light chain and His98 of the heavy chain so these residues were included. Another salt bridge key to the conformation of the CDR-H3 loop was observed formed between the side chains of Arg94 and Asp101 of the heavy chain. Gln89 of the light chain and Asn60 were added to the list of SDR due to the side chain hydrogen bonds to the backbone atoms of these residues in loops CDR-L3 and CDR-H2, respectively. The framework residue Tyr71 of the light chain was added to the list since the side chain at this position makes key hydrogen bonds with backbone atoms in CDR-L1 defining the conformation of that loop. Lastly, the side chain of His35 from the heavy chain appears to make key packing interactions with the side chain of Trp95, and thus was included in the list of SDR.

Figure 7:
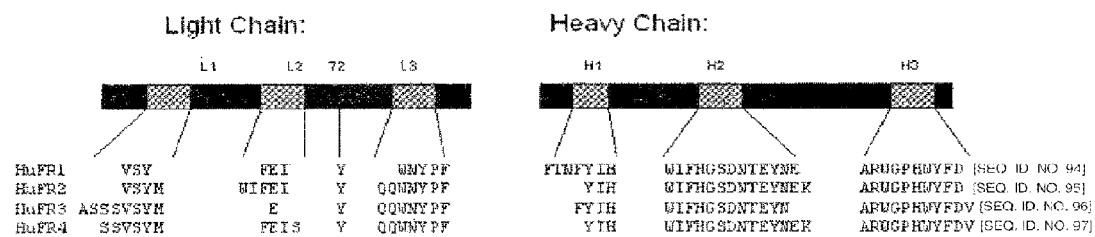
FIG. 7. Primary sequence analysis of the grafting of antibody ATN-615 onto the top scoring human antibodies from the structural analysis. The specific sequences to be grafted were determined utilizing structural information.

The key structural coordinates outlined above from the parent antibody structure 2FD6 were then used to replace coordinates from the four human antibodies from the structural analysis to form modified antibodies. First, the parent and human structure were superposed. Graft sites were then determined by structural inspection of the overlaid structures. Starting from the Chothia-defined ends of the CDR loops ad moving toward the center of the loop, each graft site was defined at the residue where either the structures diverged in the overlay or a SDR was positioned. Additionally, the framework residue at position 71 of the light chain was changed to the tyrosine residue present in the parental structure. In FIG. 7, the final parental structures selected for grafting are shown for each of the four human antibodies used. Note that the exact selection of residues varies from framework to framework.

Figure 8A:
FIG. 8. A. The critical antigen binding structures of antibody ATN-615 light and heavy chains (top, black) were grafted onto the top four scoring human framework regions. The resultant models are shown as ribbon diagrams at the bottom colored according to the source of the structure (human sequences are in gray shades). B. Stick diagram of the grafted regions of the parent (black) and the final, minimized models of HuFR1, HuFR2, HuFR3, and HuFR4 (gray) shows the conservation of the antigen binding site structure.
Figure 8B:
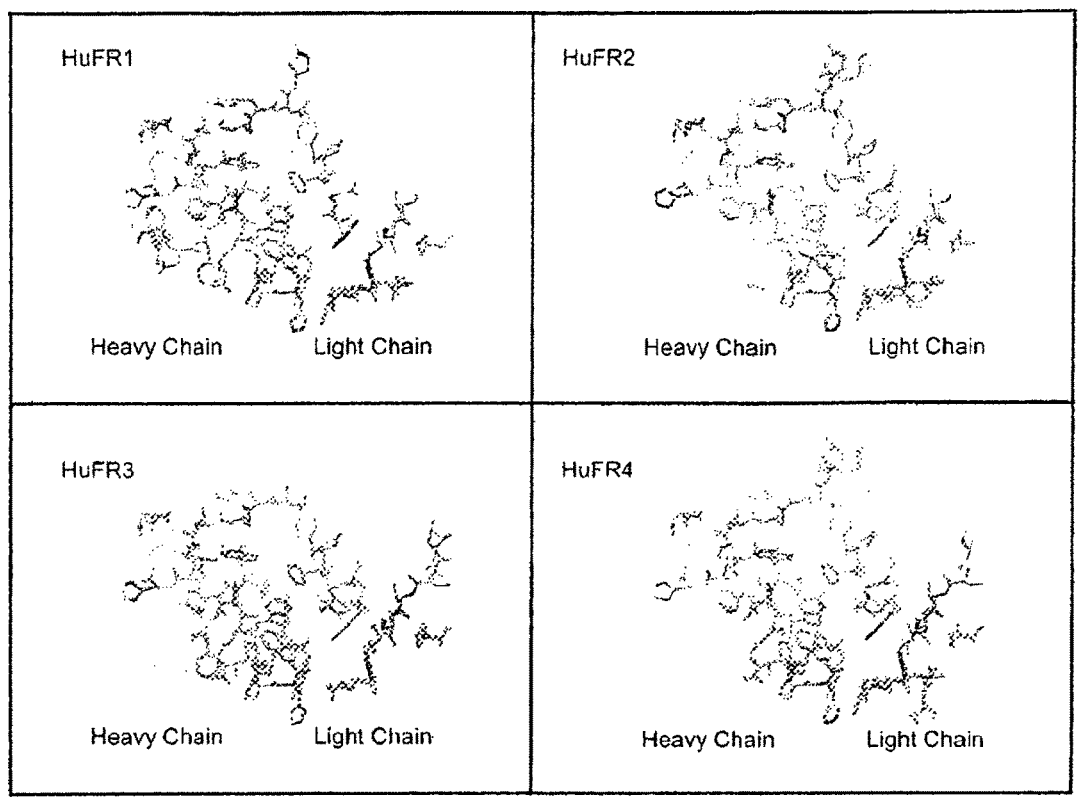

Initial energy calculations of the resultant models were performed in Deep View/Swiss-PDBViewer. Each residue showing poor energy values was then inspected in the model for alterations to the structure. Most of the poor contacts were small steric clashes that were minimized without manual intervention. There were some residues that were poor that required changes to the model to alleviate potential folding issues in the final constructs. The human antibodies all contain a leucine at position 46. This leucine makes poor steric contacts in the initial models with the side chain of Y100 of the heavy chain. The structures overlay well around position 46 of the light chain, but not well around position Y100 of the heavy chain, thus position 46 was considered for mutation. The parent has a smaller proline at this position that can accommodate the conformation of the Y100 side chain, and so the mutation of Leu46Pro was introduced into the models constructed from HuFR1, HuFR2, and HuFR3. The Leu46 side chain conformation in HuFR4 is different than the other three and showed no clashes with the Y100 side chain and thus was unmodified. HuFR3 has an asparagine residue at position 66 that was showing poor steric interactions. The other human framework antibodies and the parent antibody have a glycine at this position, so the mutation Asn66Gly was introduced to the model derived from HuFR3 prior to minimization. These mutations are easily designed using the structural information available in this method. Other methods may arrive at this same conclusion, however, many constructs would be required to be synthesized and tested, showing an advantage of use of structural models in the process. After 200 cycles of conjugate gradient minimization of these models in Deep View/Swiss-PDBViewer the models were free of poor contacts. The integrity of the binding site was maintained in each case as evidenced by the low rmsd values of 0.18-0.21 Å calculated for all atoms in the grafted regions before and after minimization. FIG. 8A shows a ribbon diagram of the final, minimized structures generated by this method colored by parental and human residues. FIG. 8B shows the conservation of the antigen binding site features using the structure-based method.

Finally, the grafted sequences were inspected to determine if the amount of parent sequence could be further reduced. Each residue in the sequences in FIG. 7 was inspected (omitting the SDR residues, which were not considered for changes). The structures of the four top scoring human antibody structures were superposed onto the 2FD6 structure and the model created from the grafting. This superposition was consulted for each position in the CDR regions to suggest possible substitutions at that position if the structures overlaid well. Each residue was replaced in the model with a low energy, favored rotamer of the mutated side chain and the model subjected to 200 cycles conjugate gradient minimization. The final energy of the mutated residue was then tabulated to determine if the mutation was compatible with the modified antibody structure. The results of these calculations are tabulated in FIG. 9. The successful substitutions were then incorporated into a combinatorial library of CDR sequences for further analysis. The final library consists of 10 possible sites of mutation with 12 possible single mutations that could be constructed and tested for improved binding properties and efficacy. Additional double, triple, etc. mutations could be constructed after further analysis to continue to tune the properties of the modified antibody.

EXAMPLE 3

Formation of a Humanized Version of a Murine Monoclonal Antibody to uPAR Using the EPU Method The EPU method outlined above (FIGS. 10 and 11) was used to modify the murine monoclonal antibody ATN-615 to create antibodies with potential therapeutic value against cancer. The solved crystal structure of antibody ATN-615 in complex with soluble uPAR and a N-terminal fragment of uPA at a resolution of 1.9 Å was obtained from the Protein Databank (code 2FD6).

Before creation of the model, the specificity determining residues of the parent antibody were determined. First, all residues within 5 Å of the soluble uPAR molecule in the complex structure were identified. These residues included Ser3 1, Tyr32, Trp91, Asn92, Tyr93, and Phe96 from the light chain and Tyr33, Trp50, Phe52, Asp55, Asn56, Thr57, Glu58, Trp95, and Trp99 from the heavy chain. The antibody binding site on uPAR comprised two amino acid segments of uPAR, residues 185-193 which interact primarily with the light chain, and residues 216-221 and Thr267, which interact exclusively with the heavy chain. Specific interactions of the antibody with uPAR include a hydrogen bond between the side chains of light chain residue Tyr32 and uPAR residue Asn186. The side chain of Leu187 makes hydrophobic interactions with the side chain of Trp99 of the heavy chain. Trp99 also forms a small pocket with the side chains of Trp95 of the heavy chain and Trp91 of the light chain in which Pro188 of uPAR resides in the structure. The backbone oxygen of Gln189 of uPAR makes a hydrogen bond to the backbone nitrogen of Tyr93 of the light chain. Additionally, the uPAR chain in this region makes van der Waal's interactions with residues Asn92, Tyr93, and Phe96 of the light chain, forming two interacting, complementary surfaces. The side chains of Trp50 from the heavy chain and Tyr93 from the light chain also make van der Waal's interactions with Gly 191 from uPAR, forming a recognition site for the backbone conformation of these residues. The side chain of Arg192 of uPAR is bound in a pocket formed by the side chains of Trp50, Asn56, and Glu58 of the heavy chain as well as the backbone of residue Thr57 of the heavy chain. The arginine side chain makes several hydrogen bond interactions with the side chains of Asn56, Glu58, and the backbone oxygen of Thr57. For the second binding segment of uPAR, Gly2 17 forms van der Waal's contacts with the side chain of Trp99 of the heavy chain. The backbone oxygen of Gly217 is also making a hydrogen bond to the side chain of Tyr33 of the heavy chain. The side chain of Asn220 of uPAR resides in a small pocket formed by the side chains of Tyr33, Trp50, Phe52, and Asn56 of the heavy chain. This asparagine side chain makes two hydrogen bonds in the pocket with the side chains of Asn56 and Tyr33. Lastly, the side chain of Thr267 of uPAR makes a hydrogen bond to the backbone oxygen of Asn56 of the heavy chain. The interactions outlined above are critical for antibody recognition of uPAR with both high affinity and high selectivity. The binding site of the parent recognizes a complex epitope comprising three protein segments on uPAR, and the interactions with uPAR are modulated by combination of amino acids from several CDR from the heavy and light chains. In order to successfully reproduce the parental binding properties in a humanized version of the parent, the spatial relationship of the residues from the parent antibody that interact with uPAR in the structure must be maintained as closely as possible. Using the next steps of the method, a humanized antibody chain will be constructed into which these residues above will be incorporated in such a way that the new antibody will fold to place these residues in the desired conformation to completely recreate the parental binding site in a humanized context.

Each SDR residue and other Chothia-defined CDR residues were then inspected individually for inclusion on the list of SDR if the residue was observed to have structural features key to proper folding and positioning of the SDR residues. Pro94 of the light chain and Pro97 of the heavy chain were added to the list to maintain the backbone conformation of these positions in the modified constructs. An interchain salt bridge was noted between the side chains of Glu50 of the light chain and His98 of the heavy chain so these residues were included. Another salt bridge key to the conformation of the CDR-H3 loop was observed formed between the side chains of Arg94 and Asp101 of the heavy chain. Gln89 of the light chain and Asn60 were added to the list of SDR due to the side chain hydrogen bonds to the backbone atoms of these residues in loops CDR-L3 and CDR-H2, respectively. The framework residue Tyr71 of the light chain was added to the list since the side chain at this position makes key hydrogen bonds with backbone atoms in CDR-L1 defining the conformation of that loop. Lastly, the side chains of His35 and Trp47 from the heavy chain appear to make key packing interactions with the side chains of Trp95 of the heavy chain and Phe96 of the light chain, respectively, and thus were included in the list of SDR.

For alignment against the human antibody structure database, the parent structure was divided into seven parts CDRL1 (light chain residues 23-35), CDRL2 (light chain residues 49-57), CDRL3 (light chain residues 88-98), CDRH3 (heavy chain residues 26-36), CDRH2 (heavy chain residues 50-68), CDRH1 (heavy chain residues 92-104), and FR (light chain residues 1-23, 35-49, 57-88, and 98-107 and heavy chain residues 1-25, 36-49, 69-94, and 103-113). Each of these structure segments was then superposed onto the corresponding database of human structure antibody segments using IMF in Deep View. For the CDR loops, the rmsd was calculated using all backbone atoms whereas only the alpha carbons were used for the FR. The alignments of the CDR loops were ranked by the total number of backbone atoms aligned and then rmsd. In this way, the closest structural relatives in the database to the parent were identified. The alignments of the FR were ranked by rmsd, and solutions using less than 90% of the alpha carbons in the alignment were discarded.

Next, the top scoring solutions for each structural segment were analyzed for alteration and inclusion in the final model, For CDRL1, the fitting showed one CDR loop that was clearly better than any other from human structure 41 of the database. Only a single change was needed to the human #1 CDRL1 loop, a mutation of a serine to a threonine, to introduce all the parent SDR from the CDRL1 loop (FIG. 12A). Four human loops from structures #1, #5, #7, and #15 fit well to the parent CDRL2 loop. A glutamic acid was needed to be introduced to incorporate the parental SDR into the CDRL2 loop, and the CDRL2 from human #7 was selected for this since the mutation was a relatively conservative change of aspartic acid for glutamic, as well as the best fit loop in terms of rmsd from human #1 (FIG. 12B). The alignment of the CDRL3 loop with the database did not successfully identify a human CDRL3 loop with good structural similarity. The entire CDRL3 loop from the parent was therefore used in the subsequent grafting steps. For the CDRH1 loop, there were six potential solutions. These were loops from human database structures #18, #16, #2, #26, #1, and #36. Several of the loops required only a single change to incorporate all the parent SDR into the human structure, and #2 was chosen for use in the model after a single substitution of an asparagine for a histidine and #18 was chosen after substitution of a valine with a tyrosine as guided by the structural overlays (FIG. 12C). The alignment of the parental CDRH2 loop showed four human loops with good rmsd scores from human database structures #33, #8, #14, and #16. A portion of the parental structure did not fit well to any of these structures, and since this piece contained several SDR, the coordinates of residues 52a-58 of the parental structure replaced the corresponding residues in the human #14 CDRH2 structure (FIG. 12D)). The final CDRH12 loop was created by mutation of two other residues, a glycine to tryptophan and an alanine to asparagine. The CDRH3 loop presented a similar case upon inspection of the overlay of the parental structure with the top scoring CDRH3 loops from human database structures #26, #23, #43, #6, and #20. The beta turn of the parent structure had no structural equivalent in the database, thus to create the final CDRH3 for the model, the coordinates of residues 95-100 of the parent structure replaced the corresponding coordinates from the CDRH3 of human structure #20 (FIG. 12E). At this point, all six CDR comprising one each for CDRL1, CDRL3, and CDRH3 as well as two choices for CDRL2. CDRH1, and CDRH2 for the modified construct were assembled in a combinatorial fashion resulting in eight potential constructs that maintain the identity of the SDR from the parent while otherwise consisting of primarily human derived amino acids.

A framework was selected from the alignment of the parent framework structure against the database of human antibody frameworks. The structure of human structure #29 fits significantly better than any other framework (FIG. 12F), so this framework was selected for the model. Before grafting, the SDR previously noted in the framework region of the parent were introduced into the framework of human structure #29. Residue 71 of the light chain was mutated from phenylalanine to tyrosine. Residue 47 of the heavy chain was conserved in both structures and was not altered in the model. To create the model, the CDR loops above were overlaid with the corresponding CDR of the parent structure. Then, the mutated framework was overlaid on the parent structure as well. These seven coordinate sets were then combined to form a complete antibody variable region comprising two single amino acid chains using a text editor and removing any overlapping residues present in the structures (FIG. 13).

Figure 14:
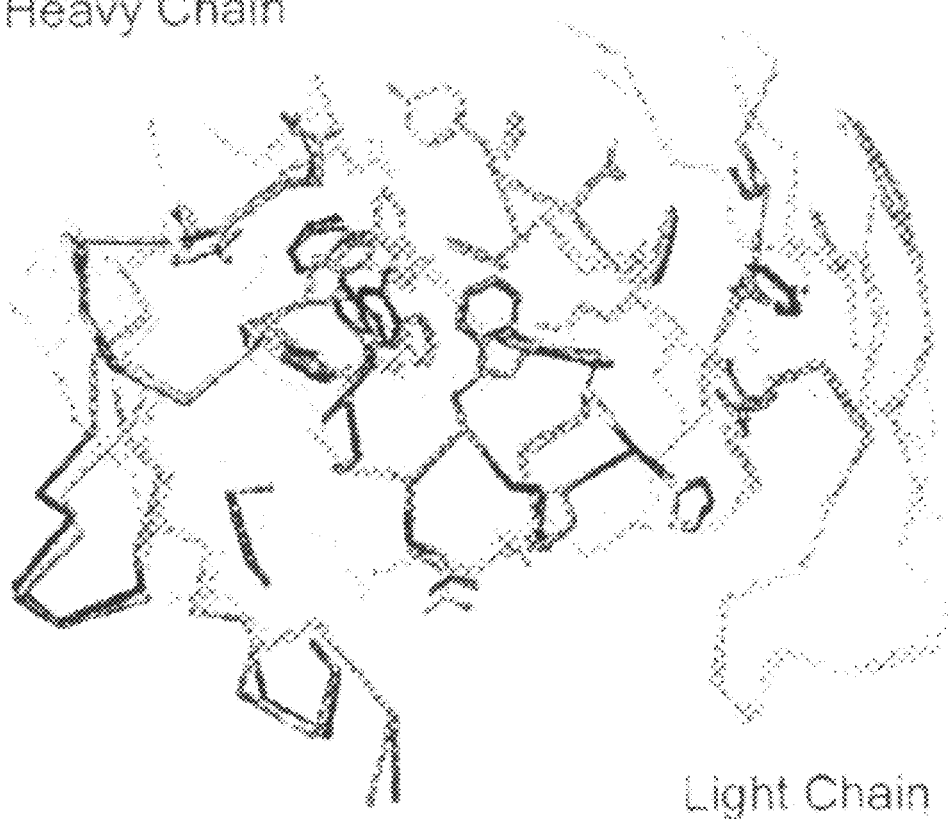

Initial energy calculations of the resultant model was performed in Deep View/Swiss-PDBViewer. Each residue showing poor energy values was then inspected in the model for alterations to the structure. Most of the poor contacts were small steric clashes that were minimized without manual intervention. There were some residues that were poor that required changes to the model to alleviate potential folding issues in the final constructs. The framework contains a leucine at position 46. This leucine makes poor steric contacts in the initial model with the side chain of Y100 of the heavy chain. The parent has a smaller proline at this position that can accommodate the conformation of the Y100 side chain and so the mutation of Leu46Pro was introduced into the model. Met48 in the heavy chain of the framework was also in bad contact with the side chain of Phe68 from the grafted CDRH2 loop. This clash was alleviated by mutation of the methionine to the parental isoleucine in the model. These mutations are easily designed using the structural information available in this method. Other methods may arrive at this same conclusion, however, many constructs would be required to be synthesized and tested, showing an advantage of use of structural models in the process. After 200 cycles of conjugate gradient minimization of these models in Deep View/Swiss-PDB-Viewer the models were free of poor contacts. The integrity of the binding site was maintained as shown in FIG. 14, showing constructs number 1 and 7 out of the eight that can be generated in a combinatorial fashion from the CDR loops generated in the previous steps. These constructs are therefore predicted to be able to make the same interactions with the uPAR protein as the parent antibody. The final sequences of the constructs outlined here are shown in FIG. 15.

Although the invention has been described with respect to various embodiments, it should be realized that this invention also encompasses a wide variety of further and other embodiments.

---

What is claimed is:

1. A purified humanized immunoglobulin comprising a light chain variable region having an amino acid sequence selected from the group consisting of SEQ ID NO: 1 and SEQ ID NO: 5; and a heavy chain variable region having an amino acid sequence selected from the group consisting of SEQ ID NO: 2, SEQ ID NO: 3, SEQ ID NO: 4, and SEQ ID NO: 6.

2. The purified humanized immunoglobulin of claim 1, wherein said light chain variable region amino acid sequence is SEQ ID NO: 1 and said heavy chain variable region amino acid sequence is SEQ ID NO: 2.

3. The purified humanized immunoglobulin of claim 1, wherein said light chain variable region amino acid sequence is SEQ ID NO: 1 and said heavy chain variable region amino acid sequence is SEQ ID NO: 3.

4. The purified humanized immunoglobulin of claim 1, wherein said light chain variable region amino acid sequence is SEQ ID NO: 1 and said heavy chain variable region amino acid sequence is SEQ ID NO: 4.

5. The purified humanized immunoglobulin of claim 1, wherein said light chain variable region amino acid sequence is SEQ ID NO: 1 and said heavy chain variable region amino acid sequence is SEQ ID NO: 6.

6. The purified humanized immunoglobulin of claim 1, wherein said light chain variable region amino acid sequence is SEQ ID NO: 5 and said heavy chain variable region amino acid sequence is SEQ ID NO, 2.

7. The purified humanized immunoglobulin of claim 1, wherein said light chain variable region amino acid sequence is SEQ ID NO: 5 and said heavy chain variable region amino acid sequence is SEQ ID NO: 3.

8. The purified humanized immunoglobulin of claim 1, wherein said light chain variable region amino acid sequence is SEQ ID NO: 5 and said heavy chain variable region amino acid sequence is SEQ ID NO: 4.

9. The purified humanized immunoglobulin of claim 1, wherein said light chain variable region amino acid sequence is SEQ ID NO: 5 and said heavy chain variable region amino acid sequence is SEQ ID NO: 6.

10. The purified humanized immunoglobulin of claim 1, wherein said humanized immunoglobulin is an antibody tetramer, Fab or (Fab)$_2$.

11. A pharmaceutical composition comprising the purified humanized immunoglobulin according to claim 10 in a pharmaceutically acceptable carrier.

12. A purified humanized immunoglobulin comprising a light chain variable region having an amino acid sequence selected from the group consisting of SEQ ID NO: 13, SEQ ID NO. 15, SEQ ID NO: 17 and SEQ ID NO: 19; and a heavy chain variable region having an amino acid sequence selected from the group consisting of SEQ ID NO: 14, SEQ ID NO: 16, SEQ ID NO: 18 and SEQ ID NO: 14.

13. The purified humanized immunoglobulin of claim 12, wherein said light chain variable region amino acid sequence is SEQ ID NO: 13 and said heavy chain variable region amino acid sequence is SEQ ID NO: 14.

14. The purified humanized immunoglobulin of claim 12, wherein said light chain variable region amino acid sequence is SEQ ID NO: 15 and said heavy chain variable region amino acid sequence is SEQ ID NO: 16.

15. The purified humanized immunoglobulin of claim 12, wherein said light chain variable region amino acid sequence is SEQ ID NO: 17 and said heavy chain variable region amino acid purified sequence is SEQ ID NO: 18.

16. The humanized immunoglobulin of claim 12, wherein said light chain variable region amino acid sequence is SEQ ID NO: 19 and said heavy chain variable region amino acid sequence is SEQ ID NO: 20.

17. The purified humanized immunoglobulin of claim 12, wherein said humanized immunoglobulin is an antibody tetramer, Fab or (Fab)$_2$.

18. A pharmaceutical composition comprising purified the humanized immunoglobulin according to claim 17 in a pharmaceutically acceptable carrier.

\* \* \* \* \*